(12) United States Patent
Wiltberger et al.

(10) Patent No.: US 12,251,341 B2
(45) Date of Patent: Mar. 18, 2025

(54) METHODS FOR INCISING TISSUE

(71) Applicant: INSIGHTFUL INSTRUMENTS, INC., Santa Clara, CA (US)

(72) Inventors: Michael Wiltberger, Santa Clara, CA (US); Phillip Gooding, Mountain View, CA (US); Dan Andersen, Menlo Park, CA (US)

(73) Assignee: INSIGHTFUL INSTRUMENTS, INC., Santa Clara, CA (US)

( * ) Notice: Subject to any disclaimer, the term of this patent is extended or adjusted under 35 U.S.C. 154(b) by 0 days.

(21) Appl. No.: 17/997,015

(22) PCT Filed: May 27, 2022

(86) PCT No.: PCT/US2022/072626
§ 371 (c)(1),
(2) Date: Oct. 24, 2022

(87) PCT Pub. No.: WO2022/251877
PCT Pub. Date: Dec. 1, 2022

(65) Prior Publication Data
US 2024/0091066 A1    Mar. 21, 2024

Related U.S. Application Data

(60) Provisional application No. 63/193,977, filed on May 27, 2021.

(51) Int. Cl.
*A61B 18/14* (2006.01)
*A61F 9/013* (2006.01)
*A61B 18/00* (2006.01)

(52) U.S. Cl.
CPC ...... *A61F 9/013* (2013.01); *A61B 2018/0016* (2013.01); *A61B 2018/00601* (2013.01); *A61B 18/1402* (2013.01)

(58) Field of Classification Search
CPC ............... A61F 9/013; A61B 18/1402; A61B 2018/0016; A61B 2018/00601
See application file for complete search history.

(56) References Cited

U.S. PATENT DOCUMENTS

| 4,542,742 A | 9/1985 | Winkelman |
|---|---|---|
| 5,215,104 A | 6/1993 | Steinert |

(Continued)

FOREIGN PATENT DOCUMENTS

| CN | 208426205 | 1/2019 |
|---|---|---|
| WO | 0009055 | 2/2000 |
| WO | 2021092628 | 5/2021 |

OTHER PUBLICATIONS

Ağca, Alper, et al. "Comparison of Visual Acuity and Higher-Order Aberrations after Femtosecond Lenticule Extraction and Small-Incision Lenticule Extraction." Contact Lens and Anterior Eye, vol. 37, No. 4, Aug. 2014, pp. 292-296, doi:10/gh2btw.

(Continued)

*Primary Examiner* — Eun Hwa Kim
*Assistant Examiner* — Catherine Premraj
(74) *Attorney, Agent, or Firm* — FisherBroyles, LLP; John K. Shimmick

(57) ABSTRACT

A system for incising tissue with a plasma comprises an elongate electrode configured to incise the tissue along a tissue incision profile and a tissue contact element configured to shape the tissue, which comprises one or more of a channel or a protrusion to form one or more of a corresponding protrusion or indentation in a tissue surface while the tissue is incised with the electrode along the incision profile. The tissue contact element shapes the tissue sufficiently to allow the tissue to form one or more complimentary features along the incision profile when the tissue relaxes to a free-standing configuration with removal of the tissue contact element. The complementary features may be (Continued)

US 12,251,341 B2

Page 2 incised into the tissue to provide increased mechanical stability between the separated tissue regions, such as with nominally interlocking protrusion(s) and indentation(s).

19 Claims, 38 Drawing Sheets

(56) References Cited

U.S. PATENT DOCUMENTS

| | | | |
|---|---|---|---|
| 5,556,406 | A | 9/1996 | Gordon |
| 5,683,366 | A | 11/1997 | Eggers |
| 5,833,701 | A | 11/1998 | Gordon |
| 6,312,440 | B1 | 11/2001 | Hood |
| 6,358,260 | B1 * | 3/2002 | Ross ............... A61F 9/0133 606/166 |
| 6,730,075 | B2 | 5/2004 | Palanker |
| 6,780,178 | B2 | 8/2004 | Palanker |
| 7,238,185 | B2 | 7/2007 | Palanker |
| 7,357,802 | B2 | 4/2008 | Palanker |
| 7,789,879 | B2 | 9/2010 | Palanker |
| 7,922,735 | B2 | 4/2011 | Daxer |
| 8,043,286 | B2 | 10/2011 | Palanker |
| 8,088,126 | B2 | 1/2012 | Fugo |
| 8,177,783 | B2 | 5/2012 | Davison |
| 8,292,877 | B2 | 10/2012 | Raksi |
| 8,323,276 | B2 | 12/2012 | Palanker |
| 8,414,572 | B2 | 4/2013 | Davison |
| 8,870,864 | B2 | 10/2014 | Davison |
| 9,018,983 | B2 | 4/2015 | Vankov |
| 11,490,948 | B2 | 11/2022 | Wiltberger |
| 11,896,283 | B2 | 2/2024 | Wiltberger |
| 2001/0025177 | A1 | 9/2001 | Woloszko |
| 2003/0084907 | A1 | 5/2003 | Pacek |
| 2006/0064113 | A1 | 3/2006 | Nakao |
| 2007/0280994 | A1 * | 12/2007 | Cunanan ............... A61F 9/007 623/6.11 |
| 2007/0282328 | A1 | 12/2007 | Yahagi |
| 2008/0021444 | A1 | 1/2008 | Scoption |
| 2008/0039832 | A1 | 2/2008 | Palanker |
| 2008/0125774 | A1 | 5/2008 | Palanker |
| 2008/0281303 | A1 | 11/2008 | Culbertson |
| 2009/0187184 | A1 | 7/2009 | Muller |
| 2009/0301860 | A1 | 12/2009 | Iida |
| 2011/0190741 | A1 | 8/2011 | Deisinger |
| 2011/0276089 | A1 | 11/2011 | Straehnz |
| 2011/0301637 | A1 | 12/2011 | Kerr |
| 2011/0313344 | A1 | 12/2011 | Daxer |
| 2012/0245580 | A1 | 9/2012 | Germain |
| 2015/0282822 | A1 | 10/2015 | Trees |
| 2015/0297257 | A1 | 10/2015 | Galer |
| 2015/0297280 | A1 | 10/2015 | Li |
| 2016/0074226 | A1 * | 3/2016 | Spooner ............. A61F 9/00827 606/5 |
| 2017/0105797 | A1 | 4/2017 | Mikkaichi |
| 2017/0333114 | A1 * | 11/2017 | Atwell ............... A61B 18/1445 |
| 2019/0328377 | A1 | 10/2019 | Johnson |
| 2020/0254270 | A1 | 8/2020 | Wandke |

OTHER PUBLICATIONS

Ang, Marcus, et al. "Small Incision Lenticule Extraction (SMILE) versus Laser in-Situ Keratomileusis (LASIK): Study Protocol for a Randomized, Non-Inferiority Trial." Trials, vol. 13, May 2012, p. 75, doi:10/gbbgv5.

Ganesh, Sri, et al. "Refractive Lenticule Extraction Small Incision Lenticule Extraction: A New Refractive Surgery Paradigm." Indian Journal of Ophthalmology, vol. 66, No. 1, Jan. 2018, pp. 10-19, doi:10/gcrf6z.

Gyldenkerne, Anders, et al. "Comparison of Corneal Shape Changes and Aberrations Induced By FS-LASIK and SMILE for Myopia." Journal of Refractive Surgery, Mar. 2015, doi:10/f684jm.

Hammer, D. X., et al. "Experimental Investigation of Ultrashort Pulse Laser-Induced Breakdown Thresholds in Aqueous Media." IEEE Journal of Quantum Electronics, vol. 32, No. 4, Apr. 1996, pp. 670-678, doi:10.1109/3.488842.

International Search Report and Written Opinion for PCT/US2022/072626, 10 pages (Sep. 28, 2022).

Lombardo, Marco, and Giuseppe Lombardo. "Wave Aberration of Human Eyes and New Descriptors of Image Optical Quality and Visual Performance." Journal of Cataract & Refractive Surgery, vol. 36, No. 2, Feb. 2010, pp. 313-331, doi:10.1016/j.jcrs.2009.09.026.

Palanker, D. V., et al. "Pulsed Electron Avalanche Knife (PEAK) for Intraocular Surgery." Investigative Ophthalmology & Visual Science, vol. 42, No. 11, Oct. 2001, pp. 2673-2678.

Pallikaris, I. G., et al. "Laser in Situ Keratomileusis." Lasers in Surgery and Medicine, vol. 10, No. 5, 1990, pp. 463-468, doi:10/cpjdwq.

Peponis, Vasileios, et al. "The Use of the Fugo Blade in Corneal Surgery: A Preliminary Animal Study." Cornea, vol. 25, No. 2, Feb. 2006, pp. 206-208, doi:10.1097/01.ico.0000179927.12899.bb.

Reinstein, Dan Z., et al. "Small Incision Lenticule Extraction (SMILE) History, Fundamentals of a New Refractive Surgery Technique and Clinical Outcomes." Eye and Vision, vol. 1, No. 1, Dec. 2014, p. 3, doi:10/gh2btx.

Sekundo W., Chapters 1, 6, 13, 15, and 19, from "Small Incision Lenticule Extraction (SMILE) Principles, Techniques, Complication Management, and Future Concepts," 65 pages (2015).

Shen, Yang, et al. "Comparison of Corneal Deformation Parameters After Smile, Lasek, and Femtosecond Laser- Assisted LASIK." Journal of Refractive Surgery, vol. 30, No. 5, May 2014, pp. 310-318, doi:10/f56ckn.

Shen, Zeren, et al. "Small Incision Lenticule Extraction (SMILE) versus Femtosecond Laser-Assisted In Situ Keratomileusis (FS-LASIK) for Myopia: A Systematic Review and Meta-Analysis." PloS One, vol. 11, No. 7, 2016, p. e0158176, doi:10/gbnfgj.

* cited by examiner

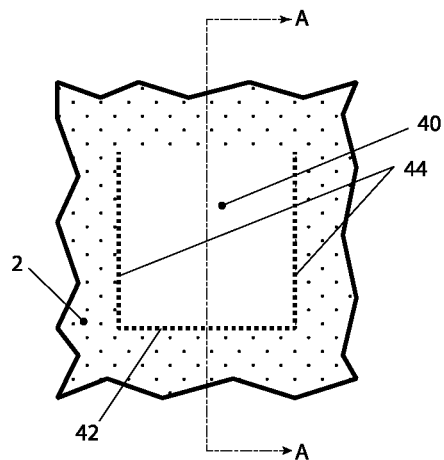 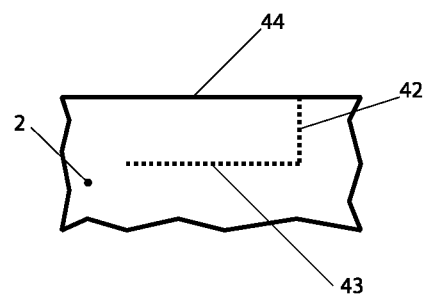
Figure 19A.  Figure 19B.
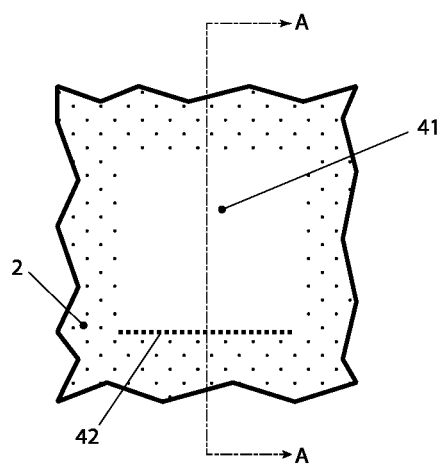 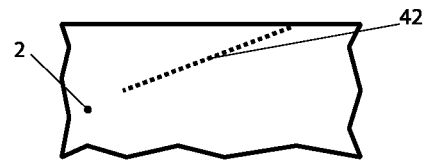
Figure 19C.  Figure 19D.

METHODS FOR INCISING TISSUE

CROSS REFERENCE TO RELATED APPLICATION

This application is a 371 national phase of PCT/US2022/072626, filed May 27, 2022, and claims the benefit under 35 U.S.C. § 119 (e) of U.S. Provisional Patent Application No. 63/193,977, filed May 27, 2021, the entire disclosure of which is incorporated herein by reference.

The subject matter of the present application is related to PCT/US2020/070757, filed on Nov. 6, 2020, entitled "Systems and methods for incising tissue", published as WO2021092628 on May 14, 2021, the entire disclosure of which is incorporated herein by reference.

BACKGROUND

Tissue ablation and incisions can be used to in many ways to perform procedures such as surgical procedures. For example, lasers can be used to correct refractive error such as myopia, to remove cataracts, and to treat glaucoma and retinal disease. Tissue ablation and incisions can also be used orthopedics and cardiology to perform surgical procedures, for example.

Work in relation to the present disclosure suggests that the efficacy and availability of surgical procedures may be related to limitations of the devices used to incise and ablate tissue in at least some instances. For example, lasers such as femtosecond lasers can be complex, and the treatments may take longer than would be ideal. Also, the tissue removal profile along a laser induced incision may not be as smooth as would be ideal in at least some instances. Also, with laser treatments tissue artifacts and debris such as a plume associated with the laser irradiation can affect the accuracy and effectiveness of ablations and incisions.

Although mechanical cutting with blades such as microkeratome blades can be used for some surgical procedures, work in relation to the present disclosure suggests that mechanical cutting with blades can be less accurate and may produce rougher surfaces than would be ideal in at least some instances. Although mechanical keratomes have been used to create corneal flaps for surgical procedures such as LASIK, work in relation to the present disclosure suggests that mechanical keratomes can take somewhat longer than would be ideal, and the resulting flaps may be some irregular and rougher than would be ideal in at least some instances. Although a scalpel or diamond knife may be used to manually resect two separate flaps within tissue, such as scleral and/or corneal tissue in traditional canaloplasty, this can be technique dependent and somewhat difficult for at least some practitioners, which may be related postoperative complications. It would be helpful to reduce technique dependency and postoperative complications.

Although, femtosecond lasers have been used to create corneal flaps and pockets, work in relation to the present disclosure suggests that the time to form the flaps and pockets may take longer than would be ideal in at least some instances. The Small Incision Lenticule Extraction ("SMILE") procedure is a more recent approach to reshaping the cornea that utilizes a femtosecond laser system to ablate tissue along the boundaries of a 3-dimensional lenticule within the corneal stroma, which may be removed through a corneal opening. However, work in relation to the present disclosure suggests that the 3-dimensional lenticule formed and removed with this procedure may be less than ideally shaped in at least some instances and may contain "tissue bridges" that must be severed from the lenticule before the lenticule may be excised. This additional step of separating the bridges between the lenticule and the corneal stroma is known to be traumatic and poses additional risk to the patient. Also, the amount of time to ablate tissue that defines the lenticule and opening can be somewhat longer than would be ideal.

Although electrodes have been proposed to treat tissue, the prior approaches can result in more tissue damage and less precise incisions than would be ideal. Although electrodes that generate plasma have been suggested, these prior approaches may not be well suited for cutting large volumes of tissue and the accuracy can be less than ideal in at least some instances.

Traditional nominally planar incisions, such as those produced by a microkeratome, may allow for dehiscence and cellular intrusion into the wound, and thus require additional post-operative medical care and/or monitoring than would be needed otherwise. Providing improved adherence of the flap to the underlying bed to decrease dehiscence and/or preclude cellular infiltration may be beneficial.

In light of the above, there is a need for improved approaches to treating tissue with incisions that ameliorate at least some of the aforementioned limitations. Ideally, such approaches would decrease complexity and treatment times and provide more accurate incisions with improved outcomes.

SUMMARY

Embodiments of the present disclosure provide improved methods and systems for incising tissue with improved stability of tissue between sides of an incision. In some embodiments, a system for incising tissue with a plasma comprises an elongate electrode configured to incise the tissue along a tissue incision profile and a tissue contact element configured to shape the tissue. The tissue contact element comprises one or more of a channel or a protrusion to form one or more of a corresponding protrusion or indentation in a tissue surface while the tissue is incised with the electrode along the incision profile. The tissue contact element shapes the tissue sufficiently to allow the tissue to form one or more complimentary features along the incision profile when the tissue relaxes to a free-standing configuration with removal of the tissue contact element. The complementary features may be incised into the tissue to provide increased mechanical stability between the separated tissue regions, such as with nominally interlocking protrusion(s) and indentation(s).

In some embodiments, an elongate electrode is configured to flex and generate plasma to incise tissue. An electrical energy source can be operatively coupled to the electrode and configured to provide electrical energy to the electrode to generate the plasma. In some embodiments, a tensioning element is operatively coupled to the elongate electrode. The tensioning element can be configured to provide tension to the elongate electrode to allow the elongate electrode to flex in response to the elongate electrode engaging the tissue and generating the plasma. In some embodiments, the tensioning element operatively coupled to the flexible elongate electrode allows the use of a small diameter electrode, such as a 5 µm to 20 µm diameter electrode, which can allow narrow incisions to be formed with decreased tissue damage. In some embodiments, the tensioning of the electrode allows the electrode to more accurately incise tissue by decreasing variations in the position of the electrode along the incision path.

In some embodiments, the elongate electrode is operatively coupled to one or more components to allow tissue resection along a path. The elongate electrode can be coupled to a support structure that moves with the electrode to provide an incision along a path. The support structure can be configured to support one or more arms, such as a plurality of arms, which arms support the electrode suspended between the arms. The support structure, one or more arms, and the elongate electrode may comprise components of an electrode assembly. The electrode assembly can be operatively coupled to a translation element to provide translational movement to the electrode in order to incise tissue. In some embodiments, a contact plate is configured to engage tissue to shape the tissue prior to incision with the elongate electrode, which can provide improved accuracy of the incision and the shape of tissue to be removed.

In some embodiments, a gap extends between the support structure and the electrode suspended between the arms, which can provide bidirectional tissue incisions and decrease treatment times. In some embodiments, the gap is sized to receive tissue and to incise tissue that extends into the gap when the support structure and electrode are drawn proximally. In some embodiments, the support structure and electrode are advanced to into the tissue to incise the tissue with a first incision on a first pass with a first configuration of one or more contact plates, and the support structure and electrode drawn proximally to incise tissue with a second configuration of the one or more contact plates. In some embodiments, the second configuration is different from the first configuration, and tissue incised with the first pass extends into the gap and is incised with the second pass to provide a resected volume of tissue for subsequent removal. In some embodiments, the resected volume of tissue comprises a thickness profile corresponding to a difference between a first profile of the first configuration and a second profile of the second configuration of the one or more contact plates. In some embodiments, a lenticule corresponding to a refractive correction of an eye is incised with the first pass and the second pass, and the lenticule can be subsequently removed to provide the refractive correction.

In some embodiments, an elongate electrode is configured to incise tissue such as corneal tissue. An electrical energy source is operatively coupled to the elongate electrode and configured to provide electrical energy to the electrode. A contact plate is configured to engage a portion of the tissue such as the cornea to shape the tissue prior to incising the cornea with the electrode. A support structure can be operatively coupled to the elongate electrode and the plate, the support configured to move the electrode relative to the plate and incise the corneal tissue with the electrode.

In some embodiments, a contact plate is configured to provide complementary features on a first surface and second surface of an incision in a tissue such as corneal tissue. Said first surface and said second surface may be the result of a single incision. Such complementary features may be configured to form nominally interlocking protrusion(s) and indentation(s) on such first and second surfaces of a tissue and be incised using contact elements and/or suction elements to deform tissue prior to an/or during an incision and may be equivalently referred to as "complementary features", "interlocking features", and "mating features" or any combination thereof. A protrusion may be configured to mate with an indentation and vice-versa. Likewise, a protrusion may be made to a first surface and/or a second surface, with its mating indentation made to a second surface and/or first surface.

In some embodiments, a suction element is configured to provide complementary features of a first surface and a second surface of an incision in a tissue such as corneal tissue and may be part of a flap or a pocket.

In some embodiments, a suction element and a contact element may be used to create complementary features.

INCORPORATION BY REFERENCE

All patents, applications, and publications referred to and identified herein are hereby incorporated by reference in their entirety and shall be considered fully incorporated by reference even though referred to elsewhere in the application. Specifically, International Patent Application No. PCT/US2020/070757, filed on 6 Nov. 2020 and titled "SYSTEMS AND METHODS FOR INCISING TISSUE" and U.S. Patent Application No. 63/193,977, filed on 27 May 2021 and titled "SYSTEMS AND METHODS FOR INCISING TISSUE" are identified herein.

BRIEF DESCRIPTION OF THE DRAWINGS

A better understanding of the features, advantages and principles of the present disclosure will be obtained by reference to the following detailed description that sets forth illustrative embodiments and the accompanying drawings listed below.

FIGS. 19A through 19D depict aspects of a tissue "flap" and aspects of a tissue "pocket", in accordance with embodiments of the present disclosure.

DETAILED DESCRIPTION

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The presently disclosed systems and methods are well suited for incorporation into prior devices and surgical procedures, such as microkeratomes, incising tissue to form one or more of flaps, pockets, or lenticles for removal from tissue, e.g., SMILE. The presently disclosed methods and systems are well suited for combination with lens removal and prosthesis, such as removal of the lens nucleus and cortex for placement of an intraocular lens. By way of non-limiting example, a plasma-induced incision may be created in the capsule to produce a capsulorrhexis. Incisions may be created in the to produce lens fragments or to simplify lens fragmentation and/or lens removal. The incisions may be formed in the retina to produce a pocket or flap. In some embodiments an incision is formed in the trabecular meshwork TM to improve drainage and/or to lower intraocular pressure ("IOP") for the treatment of glaucoma, or in the iris to produce an iridotomy for example.

Although reference is made to incisions in tissues of the eye, the presently disclosed systems and methods are well suited for forming incisions in non-ophthalmic surgeries such as orthopedic surgery, cardiovascular surgery, neurosurgery, robotic surgery, pulmonary surgery, urologic surgery, and soft tissue surgery. Although reference is made to cutting ocular tissue, the presently disclosed methods and systems are well suited to forming incisions in one or more of collagenous tissue, cartilage, stromal tissue, neural tissue, vascular tissue, muscle and soft tissue.

Figure 1A:
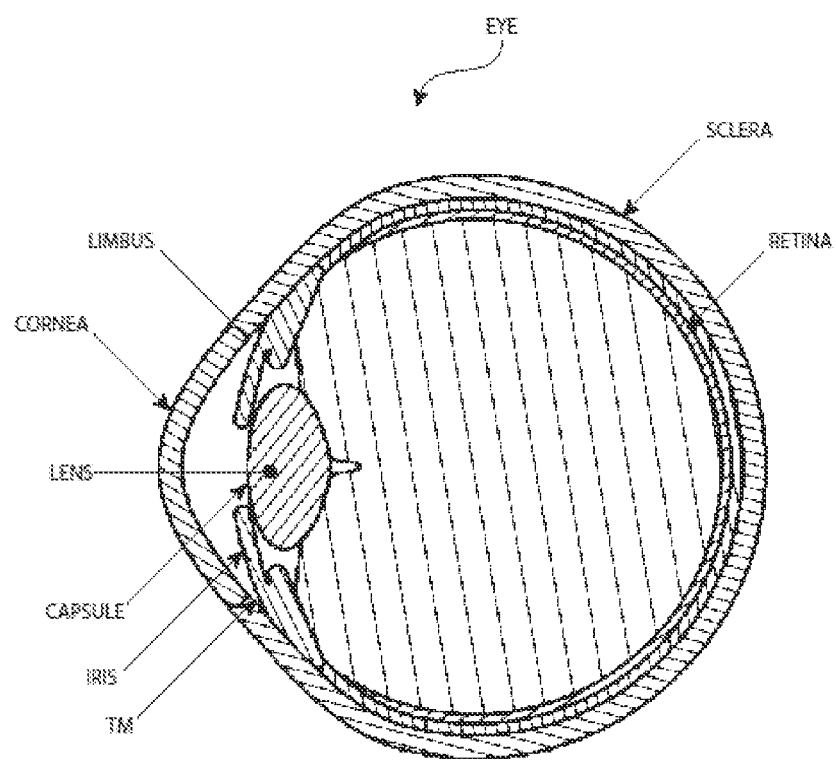
FIG. 1A is directed at a schematic image of an eye shown in cross section to show anatomical locations therein, in accordance with embodiments of the present disclosure.

By way of non-limiting example, FIG. 1A illustrates various anatomical locations in eye that may be suitable for practicing the present disclosure. The eye includes a cornea, a sclero-corneal limbus, a sclera, a lens capsule, a lens, a retina, an iris, and a TM. Although not shown for purposes of clarity, a Schlemm's canal may be located adjacent to TM. The presently disclosed systems can be used to treat any of these locations. In some embodiments, the cornea is shaped to provide refractive treatment of the eye. In some embodiments, the sclera is incised, for example to provide a filtering bleb to treat glaucoma. In some embodiments, at least a portion of the capsule is incised, for example to access the cortex and nucleus of the lens. In some embodiments, at least a portion of the lens is incised and resected. In some embodiments the retina is treated, for example with the electrode. In some embodiments, the IRIS is incised with the electrode. In some embodiments, tissues associated with TM and Schlemm's canal are incised, for example with reference to glaucoma surgery. A cornea may have an anterior corneal surface toward the exterior of the eye that includes the corneal epithelium underlain posteriorly by a Bowman's membrane, a posterior corneal surface toward the interior of the eye that includes the corneal endothelium underlain anteriorly by a Descemet's membrane of, and corneal stroma situated between the anterior and posterior corneal surfaces.

In some embodiments, the application of a sufficient voltage, including a periodic or pulsatile voltage, to an electrode in or around a biological tissue (i.e., a "target tissue structure") may result in the formation of a vapor in proximity to said electrode that derives from the initial current and/or the electric field established by heating at least a component of said tissue (e.g., water within a tissue) to about a vaporization temperature (or a "critical temperature", e.g., ~100° C. for pure water at standard pressure). The contents of such a vapor cavity may then be ionized by said electric field to disrupt (or equivalently, "ablate" or "remove") at least a portion of said target tissue structure, especially if the pulse duration of a pulsatile voltage waveform is sufficiently short when compared to the thermal relaxation time of the target tissue structure and thermal confinement is achieved and the amount remaining damaged tissue created thereby may be minimized. The creation of said vapor may be due to a phase change process and thus a concomitant temperature increase may cease once the vaporization temperature is reached via a latent heat process. The volume of said vapor cavity (or equivalently, "bubble") may increase as the amount of vapor is increased and may further scale directly with the electrode voltage and/or the current supplied by said electrode to the tissue as larger volumes of tissue are heated. Likewise, and/or pressure within said bubble may increase as the amount of vapor is increased and may further scale directly with the electrode voltage and/or the current supplied by said electrode to the tissue as larger volumes of tissue are heated. Subsequently, a plasma may be formed at least partially within said vapor cavity by ionizing the vapor should said electrode be operated with a voltage great enough such that the resultant electric field strength within the vapor cavity exceeds a discharge threshold to create a plasma-induced ablation, a combination of which when created along an electrode may create a plasm-induced incision. By way of non-limiting example, said discharge threshold may be selected from the group consisting of: an ionization threshold, an electrical breakdown threshold, a dielectric breakdown threshold, a glow discharge threshold, a plasma threshold, an ablation threshold, a disruption threshold, and combinations thereof. If the electrode voltage is great enough, the resultant electric field strength may allow for secondary discharge and produce an arc. Avoiding such arc discharge may be advantageous, as will be described elsewhere herein. Said plasma may allow electrical current to again flow through the electrode, the vapor, and the tissue, and my thus cause a further temperature increase. The bulk electrode temperature may be directly proportional to the amount of current flowing said electrode and/or to surface bombardment of ions and charged particles, chemical reactions, and radiation; which themselves may be functions of the amount of plasma generated. Energy may be efficiently delivered to a target tissue structure to achieve thermal confinement within at least a portion of a target tissue structure that is nearby the electrode and/or the vapor cavity to create and/or sustain said vapor cavity. Thermal confinement may be achieved if said energy is deposited in a target at an energy deposition rate that is greater than an energy dissipation rate; such as may be when a current only flows through a tissue nominally within a time that is less than or equal to about a thermal time constant of said tissue, such as may be achieved using a periodic or pulsatile voltage. Said thermal time constant may be a thermal relaxation time, as defined by the size or shape or geometry of the electrode, the size or shape or geometry of the vapor cavity, and combinations thereof. A time constant may alternately be defined as a mechanical response time, such as a displacement relaxation due to a transient deformation of tissue adjacent to a collapsing vapor cavity. For a semi-infinite slab of material, said thermal relaxation time τ may be approximated by $$\tau \approx \frac{d^2}{4\alpha},$$

where d is the distance into the tissue, and α is the thermal diffusivity of the tissue. For sclera and cornea is ~0.14 mm2·s⁻¹. For example, such a thermal relaxation time for a d=~2 μm damage extent is τ=~28 μs. Damage is defined herein as at least partially denatured tissue or at least partially denatured tissue components caused by the mechanism for creating the incision, such as plasma, heating, etc. Such mechanical response times may be dictated by the material's compressibility and density, which in turn may be related to the tissue hydration. For most species including humans, water may contribute ~76% of the weight of the corneal stroma.

In some embodiments, for example related to soft tissues, the following relations may be used to approximate the mechanical properties of said tissue;

$$M = K + \frac{4}{3}G,$$

where K and G are the bulk and shear moduli, respectively, and G<<K, $$M \approx K = \frac{1}{\beta},$$

where β is the tissue compressibility and the mean elastic modulus of corneal tissue may range between ~1 and ~3 MPa. Thus, a sufficiently intense and rapid increase in the temperature of a material (i.e., a tissue, or the constituents or components of a tissue) may cause an amount of said material to be vaporized. Said vaporization may be an explosive vaporization that disrupts the tissue; i.e., causes tissue "disruption," also known as "breakdown," "rupture," and "ablation." The extent of a vapor cavity may intrinsically mediate the plasma discharge process when operated as described in an at least partially compressive material, such as tissue, due to transient mechanical deformation and displacement of said material as an electric field strength may decrease as the square of the distance from an electrode (e.g. $\propto r^{-2}$) and a discharge may cease when the bubble grows to the extent that the distance from the electrode surface to the bubble surface is too large to continue to support said discharge throughout a vapor cavity with the operating voltage because the electric field strength may be commensurately diminished. Maintaining a glow-type of discharge or disallowing an arc-type of discharge may be beneficial to producing precise incisions with minimal collateral damage. Flashes of light may accompany the plasma. The rate of said flashes of light may be dependent upon a velocity. The intensity of said flashes of light may be dependent upon an energy per pulse, or the power to the electrode.

Figure 1B:
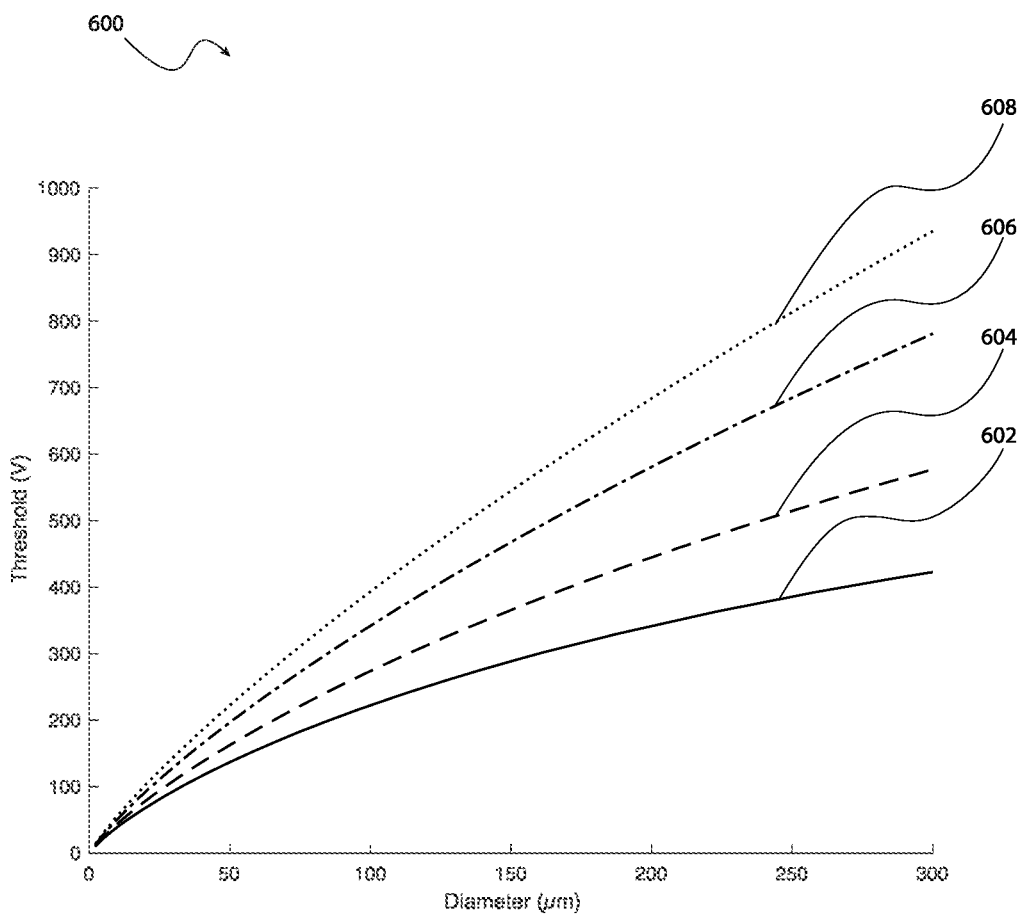
FIG. 1B is directed at a plot displaying a relationship between the measured threshold discharge voltage and pulse duration for negative and positive voltages for a single long, thin electrode, in accordance with embodiments of the present disclosure.

In some embodiments, the required voltage and associated energy deposition may be reduced by decreasing the width of the electrode, as shown in FIG. 1B, which contains plot 600; a relationship between the negative voltage threshold for tissue vaporization versus the diameter of a long cylindrical electrode for ~50 us pulses using electrode lengths of ~1 mm, ~2 mm, ~5 mm, and ~10 mm corresponding to curves 602, 604, 606, and 608, respectively.

Such electrodes may be deemed "elongate electrodes" due to the aspect ratio between a width and a length of said electrode. That is, an elongate electrode comprises a cross-sectional distance that is significantly smaller than its incisional length. This voltage may be made to be as low as possible and cutting with this voltage may be possible when the voltage exceeds the breakdown threshold without allowing for significant thermionic emission, where significant refers to an amount that noticeably contributes to tissue thermal damage beyond what would otherwise be present. An electric field around an electrode may scale with distance r is as follows, $$E = \frac{E_e r_e}{r},$$

where $E_e$ is the electric field at the surface of the electrode and $r_e$ is the radius of the electrode. Thus, the difference in electrical potential on the surface of the electrode to that at distance R from a nominally cylindrical elongate electrode may be $$\Delta U(R) = \int_R^{r_e} E(r) dr = E_e r_e \ln\left(\frac{R}{r_e}\right).$$

Thus, it may be that the electric field becomes nominally spherical at distances larger than the length of the electrode, L, and we may assume that at distances comparable to L the potential drops to zero; yielding $$E_e = \frac{U_e}{\ln\left(\frac{L}{r_e}\right)}.$$

The power density of the Joule heat generated by a current density j in a conductive material with resistivity $\gamma$ may be $$w = j^2 \gamma = \frac{U_e^2}{r_e^2 \gamma \ln\left(\frac{L}{r_e}\right)^2}.$$

The minimal energy density A required for vaporizing the surface layer of water within a tissue may be $A = w\tau = pC\Delta T$, where $\Delta T$ is the temperature rise of a liquid layer during a pulse of duration $\tau$, $p = \sim 1$ g/cm$^3$ is the density of water, and $C = \sim 4.2$ J·g$^{-1}$·K$^{-1}$ is its heat capacity. Thus, the voltage U required for vaporization may be $$U = r_e \sqrt{\frac{pC\Delta T \gamma}{\tau} \ln\left(\frac{L}{r_e}\right)}.$$

This voltage and associated energy deposition may be reduced by decreasing the thickness of the electrode; i.e., the radius of the aforementioned wire. Pulse durations $\tau$ may be kept shorter than a thermal relaxation time $\tau_r$ of a target tissue structure for a given electrode geometry. For example, the 1/e relaxation time for a long cylinder may be $$\tau_r \approx \frac{d^2}{9.32\alpha}, \text{ where } \alpha \equiv \frac{k}{\rho C}$$

is the thermal diffusivity of the material, and k being the thermal conductivity, which may yield a $\tau_r$ of ~65 us for a ~20 µm diameter pure tungsten wire electrode, or ~⅕th that of an equivalent cylinder of water or tissue, as $\alpha_{tungsten} = \sim 0.66$ mm$^2$·s$^{-1}$ and $\alpha_{tissue} = \sim 0.14$ mm$^2$·s$^{-1}$. It may be noted from these curves that for a wire electrode of length of ~10 mm and diameter of less than ~30 µm utilizing a negative voltage of ~—200V may be appropriate for incising a target tissue structure while maintaining a margin of ~200V between the positive going breakdown threshold, as will be described elsewhere herein.

In some embodiments, discharge may start from vaporization of tissue around electrode and may continue when voltage is high enough to bridge the ionized gas-filled vapor gap between the electrode and the tissue. If the voltage is not enough to maintain such a vapor cavity along the entire length of electrode, liquid may contact the electrode, and allow an electrical current through that interface. The depth of heating may be proportional to the length of the liquid-electrode interface. Thus, the extent of the damage zone may increase with decreasing voltage for an otherwise fixed system. Greater voltage may correct for this, but if the voltage exceeds both negative and positive plasma thresholds, the electrode may become too hot and the plasma discharge may be self-sustained, as will be described elsewhere with respect to FIG. 3. Thermionic emission may be avoided to limit collateral damage to tissue. Turbulence may break the vapor cavity and both electrode and tissue may be damaged. An electrode may be so thin that a small voltage can support the vapor cavity and said voltage may be slightly above plasma threshold. A small thickness of vapor cavity may be maintained around at least a portion of the electrode at voltages lower than any plasma threshold. Translating the electrode may allow for contact of a small region of tissue and may be conceptualized as a single point of contact, or point-like contact. Such point-like contact may cause sudden vaporization, ignite a plasma discharge in the commensurately confined volume and disrupt tissue thereby. After a section of tissue is disrupted in this manner, a different section of the tissue may be already touching the advancing electrode elsewhere, leading to a next vaporization, discharge, and subsequent disruption in this region. The amalgamation of such disruptions may be considered an incision. The heat distribution around a point-like discharge may be nominally spherical. The extent of heat deposition may be short and may scale as $r^{-4}$ where r is radius of discharge and the tissue damage zone may now depend more on the radius of electric discharge and less on length of electrode. If the radius of the point-like discharges is in the ~10 µm range, a sequence of such discharges may cut the tissue in a "punctuated" or "staccato" fashion by repeatedly breaking down different regions (i.e., at noncontiguous locations or, equivalently, non-overlapping regions) of tissue along the electrode length and may leave a damage zone of only about a few µm in thickness. These discontinuous breakdown regions may be thought of as constituting a nonuniform breakdown. Such discontinuous breakdown may be achieved if the electrode is allowed to flex (or equivalently to "deform" or to "vibrate" or to "bend" or to "stretch"), as is described elsewhere herein. A constant arc may be avoided, and plasma made to remain in the glow regime by repeatedly breaking down regions of tissue and thereby modulating the electrode voltage to minimize damage from thermionic and resultant thermal effects. The different regions of tissue within a target tissue structure that may be repeatedly broken down may be adjacent to each other but need not.

Figure 2A:
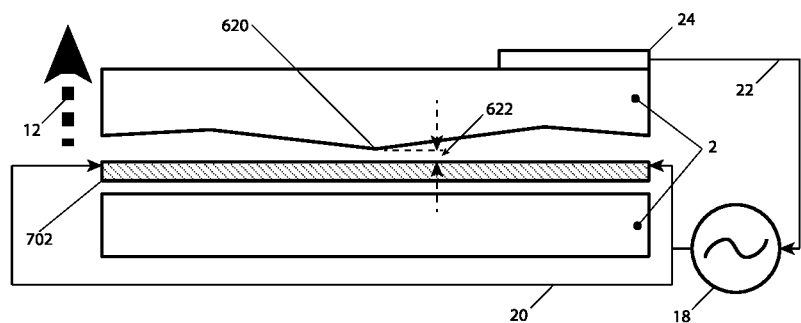
FIGS. 2A through 2F depict examples of different conditions encountered with varying electrode-to-tissue spacing and/or the electrode voltage, in accordance with embodiments of the present disclosure.

FIG. 2A illustrates electrode 702 approaching tissue 2 along direction 12, where gap 622 exists between electrode 702 and the closest region of tissue to the elongate electrode, tissue region 620. In this exemplary embodiment, both ends of electrode 702 are connected in parallel to driver 18 via connections 20 and the return path to driver 18 is via connection 22 from return electrode 24. Driver 18 may be considered to be an electrical energy source that provides electrical energy to the electrode in order to produce plasma within a target tissue structure.

Figure 2B:
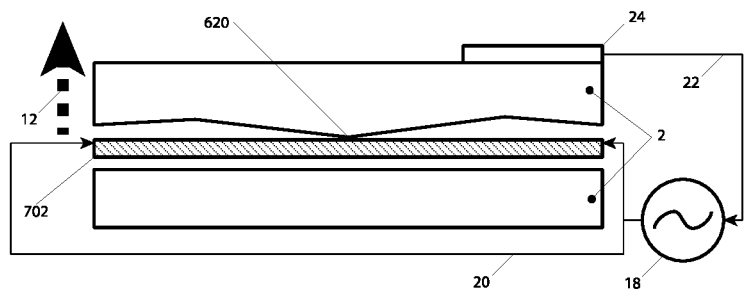

FIG. 2B illustrates the initial instantaneous connection of tissue 2 to electrode 702 at contact region 620, wherein gap 622 has decreased to ~0.

Figure 2C:
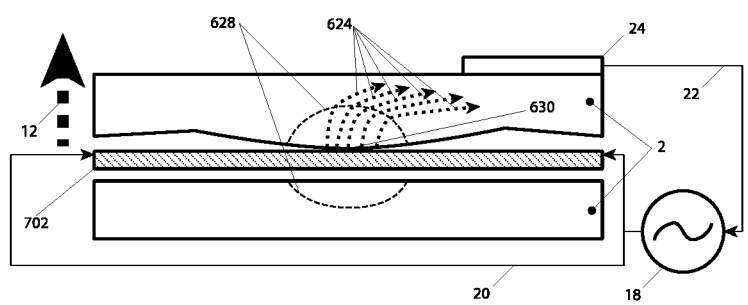

FIG. 2C illustrates a condition wherein the magnitude of the voltage on electrode 702 is above at least a negative voltage plasma threshold value in region 620 (not shown) which may cause vaporization of at least a component of tissue 2 within tissue region 626 to create a vapor cavity 635 and may allow current 624 to flow to return electrode 24 and may create damage zone 628. Such damage zone 628 in turn may be limited in extent to a volume of tissue directly adjacent to tissue region 620 and either of such tissue regions 625 & 627 may be the next portion of tissue 2 to instigate vaporization in the same manner as region 620 did previously to create a staccato process, as described elsewhere herein where noncontiguous portions of the electrode may contact associated noncontiguous portions of the target tissue during an incision. Discharge may start from the vaporization of tissue around electrode and may continue while voltage is high enough to bridge the vapor gap between the electrode and the tissue and ionize the vapor in the gap. If a portion of such an electrode has no contact with the tissue, for example, as may be the case when a vapor bubble has been formed about that region of the electrode, the electrode temperature may rise and increase in resistivity. For example, as may happen when a portion of a wire consumes more current than another portion of the wire when connected in series to a power source that is in "power-limiting-mode", as the average power may stay constant, but localized overheating in regions of increased resistivity may cause the portion of the wire to evaporate and break. However, this may be reduced (or avoided) if an electrode is placed at a common voltage, such as may occur if both ends of a wire are connected to the same location in a circuit (or "node"). In this exemplary configuration, when one portion of the electrode may become more resistive due to overheating and the current may go through another portion of the electrode, wherein the current through the heated region may decrease and preserve the wire from failing as described earlier with respect to the serial connection configuration. The velocity of a moving electrode may be chosen to satisfy the condition of constant tension below the rupture tension of the wire. Too little tension may reduce said velocity. If an electrode is not in contact with tissue, there may be no heat transfer from the electrode to the tissue and the electrode temperature may increase. An arc current may then increase due to the electrode temperature increase and may instigate a positive feedback loop, which may in turn cause an overheating of tissue and/or the electrode when the electrode is under slack and/or low tension conditions that reduce the likelihood of a small region tissue contacting the electrode to produce the aforementioned staccato discharge. Since the plasma threshold is polarity dependent, the discharge may work as a rectifier and a rectified current may be used as feedback for cutting at about a minimum negative voltage threshold for plasma discharge, including by way of non-limiting example operation in the glow discharge regime. In this configuration the damage zone may now depend on the radius of the electric discharge instead of the electrode length. A punctuated sequence of discharges whose extents are in the ~10 μm range may result in a damage zone thickness of between ~1 μm and ~3 μm. The duty cycle of the power supply (e.g., driver 18, or "electrical energy source") in this configuration may be kept at ~100% due to the punctuated discharge process.

Figure 2D:
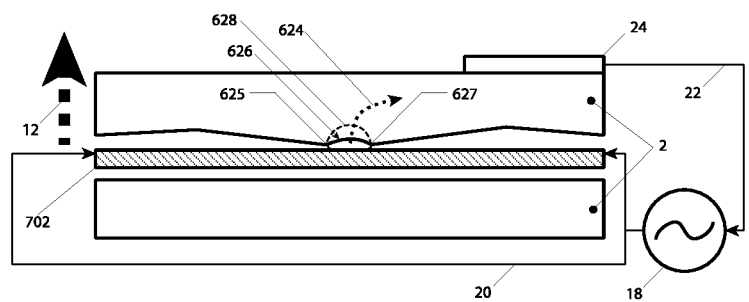

FIG. 2D illustrates a condition wherein the voltage on electrode 702 is below a plasma threshold value and may fail to maintain a vapor cavity 635 such as region 626 of the previous figure and may cause contact region 620 to expanded along electrode 702 to produce extended contact region 630, which is larger than contact region 620, and may allow for more current 624 to flow from electrode 702 through tissue 2 to return electrode 24, producing a larger damage zone 628 than that of FIG. 2C, which may extend to portion of tissue 2 behind direction 12 via thermal conduction. If the electrode voltage cannot maintain a vapor cavity 635 along the electrode, tissue and/or liquid may contact the electrode and allow a large current through the interface. The extent of the damage may be proportional to the length of the electrode-tissue interface; i.e., extended region 630. Thus, a damage zone extent may increase with a decrease of voltage. Similarly, large damage zone may occur if no voltage is supplied to the electrode prior to its contacting tissue, as a relatively large portion of said electrode may simultaneously contact tissue before a discharge process initiates. To avoid such damage, a suprathreshold voltage may be applied to the electrode before it contacts tissue and an incision be produced as described with respect to FIG. 2C. Another way to protect tissue from overheating may be by using nonconductive liquids like Electro Lube Surgical, or viscoelastic substances (e.g., Healon). Such nonconductive liquids may serve as both a cooling agent and protection against current-related tissue damage such as electroporation. For example, a nonconductive liquid may be injected into the cutting region to protect tissue nearby the target tissue which may be in the current return path. Nonconductive liquid may also be cooled before use.

Figure 2E:
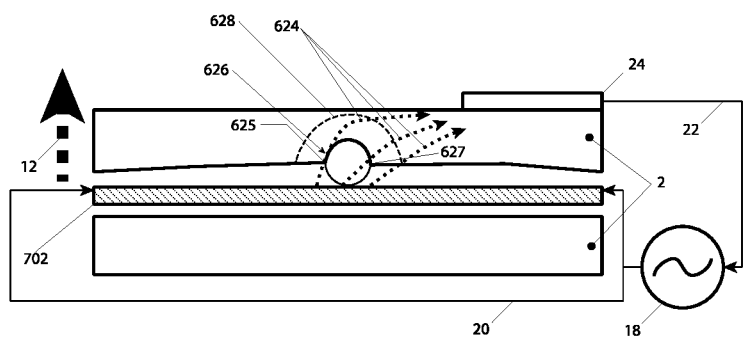

FIG. 2E illustrates a condition wherein the magnitude of the voltage on electrode 702 may be greater than both a negative plasma threshold value and a positive plasma threshold value and contact region 620 has expanded along electrode 702 to produce a vaporization region 626 that may be greater than that of the vaporization region 626 in FIG. 2C. Likewise, more current 624 may flow from electrode 702 through tissue 2 to return electrode 24 in this configuration than that of FIG. 2C, producing a larger damage zone 628 than that of FIG. 2C. An electrode voltage exceeding both negative and positive plasma thresholds may cause the electrode to become hot enough to provide self-sustained thermionic emission. Turbulence may interrupt vapor cavity 635 and may damage the electrode and/or the tissue.

An elongate electrode may comprise a nominally circular cross sectional (or "round") wire and decreasing the electrode width may be equivalent to reducing the diameter (or, equivalently, its "cross-sectional distance") of said wire. This voltage may be kept as low as possible while still rupturing tissue to avoid overheating of a target tissue. The electric field from a nominally cylindrical electrode may tend toward zero at distances on the order of the electrode length, which may in turn cause unnecessarily extended damage zones in tissue when using such an electrode with an aspect ratio >>1 (e.g., when the electrode comprises a long, thin wire). A staccato process of tissue breakdown as described herein may provide for a reduced damage zone due to the intrinsic interruption of current flow through tissue that may accompany said approach, as in the absence of tissue disruption electrical current may nominally only substantially flow through tissue when the tissue is contact with the electrode.

Although usually circular in cross-section, wire can be made in square, hexagonal, flattened rectangular, or other cross-sections. Thus, an electrode may be alternately configured using a nominally non-circular cross-sectional conductor, such as that of a rectangular cross-section. Such nominally non-circular cross-sectional wire may be available from Eagle Alloys (Talbott, TN). Rectangular cross-sectional electrodes may be created by stamping a foil sheet, such as those that also may be available from Eagle Alloys (Talbott, TN). A non-circular cross-section electrode may be further configured such that its thinnest dimension is nominally parallel to the translation direction to provide for electrode deformability along the translation direction and increased stiffness in the orthogonal direction. A conducting wire or thread with a high melting point, forming part of an electric circuit may be referred to as a filament as will be appreciated by one of ordinary skill in the art.

Figure 2F:
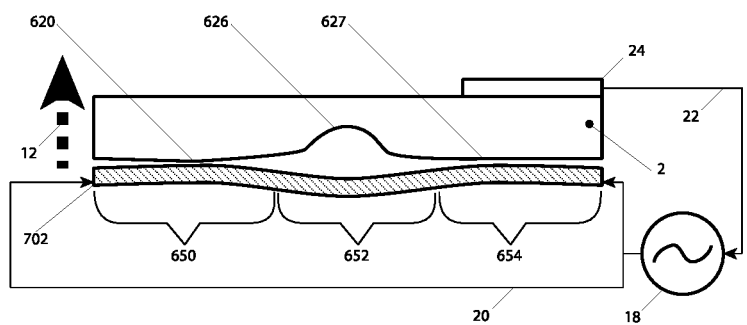

FIG. 2F illustrates a condition wherein electrode 702 may be comprised of electrode regions 650, 652, and 654, which need not represent the entire incisional length. The electrode as shown has deformed during an incision and electrode regions 652 and 654 are displaced in the direction of motion 12 while electrode region 650 is not, which may occur when at least one of the electrode regions 650 through 654 is flexible. By way of non-limiting example, configuring electrode 702 to be flexible, such as by using a thin wire, for at least a single region of an electrode regions 650 through 654 may provide said deformability. In the exemplary embodiment, a new closest region of tissue to the electrode, most proximal tissue region 620 is now approached by electrode region 652 and most proximal tissue region 620 is what was tissue region 625 of FIG. 2C and may be the next portion of tissue 2 to instigate vaporization in the same manner as region 620 did previously to create a piecewise incision. The shape of tissue 2 may be altered by the ablation of at least a single tissue region and thus cause a portion of tissue 2 to instigate vaporization in the same manner as region 620 did previously to create a piecewise incision where noncontiguous portions of the electrode may contact associated non-contiguous portions of the target tissue during an incision.

Figure 3:
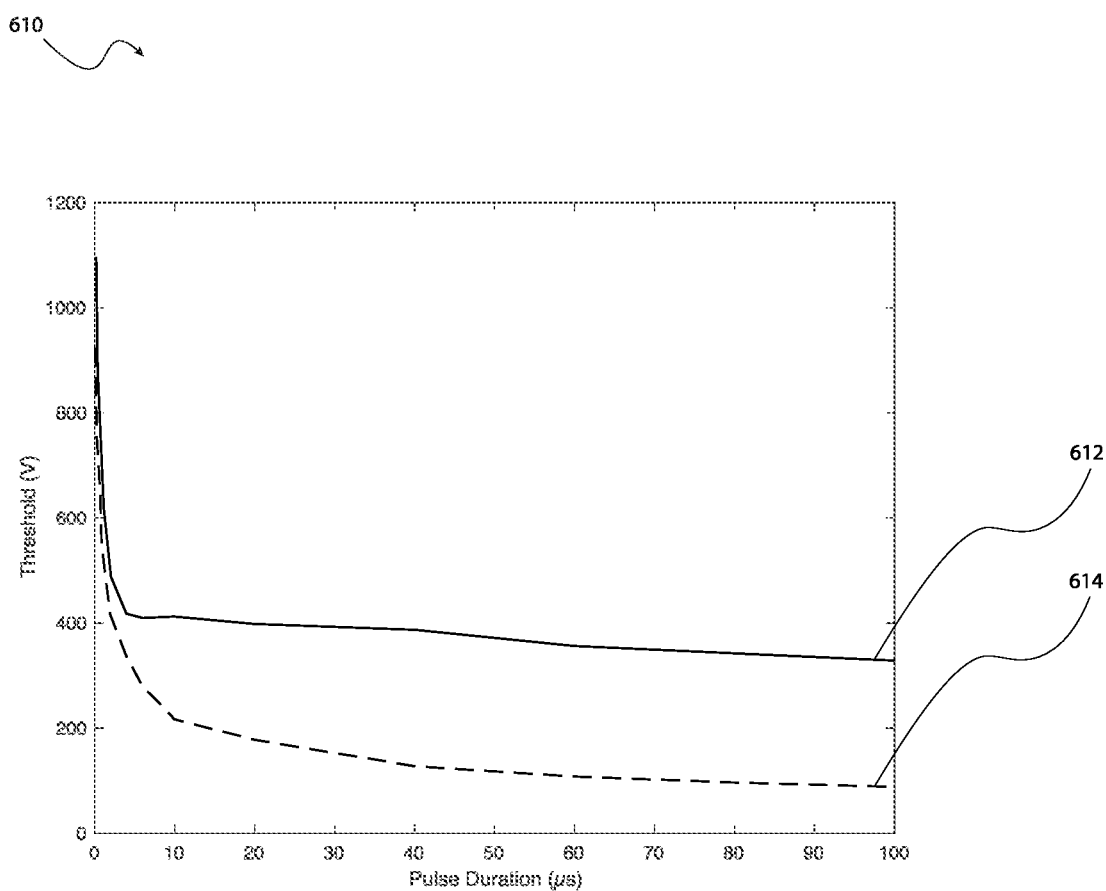
FIG. 3 is directed at a plot displaying a relationship between the measured negative threshold voltage and electrode diameter for a fixed pulse of varying duration, in accordance with embodiments of the present disclosure.

FIG. 3 shows plot 610; measured relationships between the polarity dependent voltage thresholds for vaporization versus pulse duration for a negative voltage discharge (curve 614) and a positive voltage discharge (curve 612) using a pulsatile voltage delivered with a ~8 mm long ~Ø50 μm tungsten wire electrode submerged in a bath of a physiologically balanced salt solution and observing such discharge using a camera. The lower threshold voltage for the negative discharge regime may lend itself to creating an incision with less damage than that of the positive discharge regime due to the concomitant lower currents. Thus, driver 18 may be configured to utilize a negative voltage bias.

A pulsatile voltage waveform may be used to create a plasma as described. In water, for example, a vapor cavity may expand at a mean velocity of ~0.5 m·s$^{-1}$, as averaged over a bubble lifetime of ~500 μs, away from a ~Ø20 μm thick electrode operating with a nominally sinusoidal waveform having a peak voltage of ~300V, causing discharge to cease due to a collapse of the vapor bubble (and possible subsequent cavitation), which may transfer momentum between the material and the electrode. In this configuration, the time required to reignite a plasma may be on the order of milliseconds, which may be long in comparison to the pulse period of the energizing waveform in the ~MHz regime and require considerably greater voltage to sustain discharge. However, if the distance between the tissue and the electrode surface is reduced, such as by moving the electrode, breakdown may be reinitiated sooner. The velocity of the resultant incision produced by the plasma may be referred to herein as the "tissue velocity." The frequency of a pulsatile electrode voltage may be configured in the ~MHz range and allow for a plurality of cycles during a tissue breakdown and/or a bubble lifetime. By way of non-limiting example, the nominal type of said waveform may be selected from the group consisting of: a sinusoidal waveform, a square-wave waveform, a triangle-wave waveform, a ramp waveform, a periodic waveform, a non-periodic waveform, and combinations thereof. The amount of time it takes for the electrode to move into tissue contact and the amount of time it takes for vaporization may be longer than the amount of time it takes to complete a discharge process. An electrode may be cooling when not disrupting tissue and the time an electrode is in contact with tissue and not disrupting tissue may cause tissue damage due to thermal diffusion from the electrode into the tissue, which may in turn require more energy to overcome a reduced electrode temperature. Thus, a lower incisional duty cycle may engender concomitantly greater thermal damage to tissue than a higher incisional duty cycle.

In some embodiments, the failure to achieve thermal confinement may result in collateral tissue damage. Such as may be the case for a rigid electrode, as the velocity at all locations along the electrode is constant, but the velocity of the tissue along the electrode may not be constant, i.e., there may be a distribution of tissue velocities in both time and space along the cutting edge of an electrode. A rigid electrode can only move as fast as the slowest cutting velocity it achieves. That is, a rigid electrode may need to incise a complete path along its cutting edge in order to advance and incise further, thus causing regions of tissue to compact onto the electrode prior to being incised and limit the instantaneous cutting velocity by allowing only an average cutting velocity. Hot spots along the cutting edge of a rigid electrode may provide for punctate vaporization, but those same locations may then linger in tissue awaiting similar breakdown at other locations, even with a rigid elongate electrode. The time spent lingering may be longer than a thermal or a mechanical response time of a tissue and result in collateral damage due to heat dissipation into tissue, especially in the presence of excessive liquid. A more efficient use of energy may be the desiccation of a next region of tissue to be incised. Actuating a rigid electrode at too fast a translation rate may not allow for a complete incision and cause "traction." Collateral damage may be thus reduced if the actuated velocity of an electrode nominally accommodates the discharge velocity within a vapor cavity 635.

In some embodiments, a deformable electrode may move within the material it is incising with a piecewise velocity profile. That is, unlike a traditional rigid electrode, a portion of a deformable electrode may advance into a cavity (or "bubble") created by a vaporization event to then vaporize a new region of tissue before other regions along the electrode have similarly advanced and thus allow for a velocity distribution of instantaneous cutting velocities along the electrode. Such a deformable electrode may be kept under tension along its length, which may in turn cause the deformable electrode to advance through tissue at a rate at least partially determined by an average cutting rate and at least partially determined by a local cutting rate, which may be itself at least partially determined by the tension force on the electrode. The mass (or a mass density) and/or the stiffness of a deformable electrode may at least partially dictate its ability to advance into a cavity created by a vaporization event. An average cutting rate may be affected by moving an electrode or electrode assembly using a translation element (or "translation device") and an actuator (e.g., along the x-axis, where +x may be defined as the direction of the intended incision). By way of non-limiting example, a translation element may be selected from the group consisting of: a translation stage, a linear stage, a rotary stage, a rail, a rod, a cylindrical sleeve, a screw, a roller screw, a travelling nut, a rack, pinion, a belt, a chain, a linear motion bearing, a rotary motion bearing, a cam, a flexure, a dovetail, and combinations thereof. As used herein, the terms "stage" and "slide" are considered equivalent when used to describe a translation element, device, or system. By way of non-limiting example, such actuators may be chosen from the group consisting of, a motor, a rotary motor, a squiggle motor, a linear motor, a solenoid, a rotary solenoid, a linear solenoid, a voice coil, a spring, a moving coil, a piezoelectric actuator, a pneumatic actuator, a hydraulic actuator, a fluidic actuator, and combinations thereof. Alternately, the electrode assembly may be manually actuated.

In some embodiments, a tension may be chosen to accommodate the stiffness of the material being used to form an electrode, such as may be represented by an elastic modulus. By way of non-limiting example, an elastic modulus may be chosen from the group consisting of: a flexural modulus, a Young's modulus, a bulk modulus, a section modulus, and a shear modulus. For a deformable electrode supported at least a single end by a support structure, a modulus E of the electrode material may be used to determine a tension force F for an allowed deflection distance $$d = \frac{FL^3}{48IE},$$

where L is the unsupported length of the electrode and I is the second moment of inertia for the cross-sectional shape of the electrode; and may be given by $$I = \frac{bh^3}{12}$$

for a rectangular electrode, where b is the thickness of the electrode in the direction orthogonal to the deflection, and h the thickness of the electrode in the direction of deflection, such as may be equal to $\sim 2\ r_e$ as described earlier herein. Similarly, second moment of a cylindrical electrode, such as a wire, may be given by $$I = \frac{\pi r^4}{2},$$

where r represents the radius of said cylinder.

In some embodiments, there may be a tradeoff between a characteristic extent (i.e. a "dimension" or a "thickness" or a "size") of an electrode (e.g., a diameter in the case of a wire or other such elongate electrode) and its corresponding mechanical stability, and therefore the strength and ruggedness of an instrument constructed thereby, especially in a system comprising a moving elongate electrode. Therefore, a thin wire electrode stretched taught may provide for increased mechanical stability over a slack thin wire electrode. Increased mechanical stability may manifest increased incisional precision (e.g., such an electrode may be less likely to drift transversely to the incision direction). An alternate embodiment may further comprise a tensioning element mechanically coupled to the electrode provide for a nominally more constant tension force on the electrode. A thin, deformable elongate electrode as described herein may be treated as the fundamental mode of a simple harmonic oscillator, with a fundamental frequency (or, equivalently, a mechanical resonance frequency)

$$f_0 = \frac{1}{2\pi}\sqrt{\frac{k}{m}},$$

with k being the material stiffness and m the mass. The collapse of a vapor cavity may cause said tensioned electrode to accelerate at least partially according to the tension provide and where the collapse of the cavity may be considered much like releasing a plucked string (i.e., the electrode). A force F on such a tensioned deformable elongate electrode adjacent to a cavity of extent z may then be understood as $$F = \frac{2Tz}{l},$$

where T is the tension on the electrode, l the unsupported length of the electrode, and extent z may be a diameter of a nominally spherical cavity, and z<<l. Similarly, $$f_0 = \frac{1}{\pi l}\sqrt{\frac{T}{2\mu}}$$

for a tensioned electrode with linear mass density μ, where $$\mu = \frac{\pi \rho \varphi^2}{4}$$

and p=~9*10³ kg·m⁻³ for pure tungsten.

For example, considering a ~Ø10 μm nominally pure tungsten wire of unsupported length l=~10 mm (i.e., a mass of ~7 μg, or a linear mass density μ (or, equivalently, a mass per unit length) of ~0.7 μg·mm⁻¹) that is tensioned at T=~200 mN the preceding relations may yield k=~40N·m⁻¹, f=~12 kHz and a period of τ=~83 μs. Alternately, a ~Ø5 μm nominally pure tungsten wire of unsupported length l~10 mm, μ~0.177 μg·mm⁻¹, and T~100 mN may yield f=~17 kHz. Alternately, a ~Ø19 μm nominally pure tungsten wire of unsupported length l~8 mm, μ~2.55 μg·mm⁻¹, and T~300 mN may yield f=~9.65 kHz. Alternately, a ~Ø12.5 μm nominally pure tungsten wire of unsupported length l~3 mm, μ~1.1 μg·mm⁻¹, and T~300 mN may yield f=~39.1 kHz.

Alternately, a ~Ø200 µm nominally pure tungsten wire of unsupported length 1~12 mm, µ~282 µg·mm$^{-1}$, and T~1N may yield f=~1 kHz. The force required to deform an elongate electrode may scale nonlinearly with a characteristic cross-sectional distance of said electrode.

In this configuration such an electrode may be translated in the x-direction, and may be displaced ("plucked") by x~20 µm to produce a local peak velocity, $$x' = \frac{20\mu m}{\frac{83\mu s}{4}} \rightarrow \sim 1 m \cdot s^{-1},$$

which may be constrained to motion predominantly along the incision direction, x-axis (i.e., parallel to the direction of electrode translation, or equivalently, transverse to an elongate direction) and thereby minimizing errors that are transverse to the intended incision direction. Such a configuration may provide for reduced thermal damage and/or reduced traction as compared to that of systems comprising of rigid electrodes as primary heat deposition and/or thermal diffusion may be relatively reduced by utilizing such a deformable electrode to better match the tissue velocity. Such a deformable (or "flexible") electrode may move faster than its associated plasma incises tissue, as a local velocity of said electrode may be inversely proportional to the sag on said electrode and said electrode may tend to follow the plasma to relieve an increased tension thereon and may move with velocities greater than ~1 m·s$^{-1}$. In doing such, said electrode may be said to "flex" or "deform" or "vibrate" or "stretch" or "bend." As such, an elongate electrode, as described herein, may vibrate transversely to the elongate axis of the electrode. By way of non-limiting example, the following table lists various configurations of electrode materials, sizes, and their corresponding mechanical resonance frequencies.

| Electrode Material | Electrode Diameter (µm) | Electrode Length (mm) | Electrode Tension (N) | $f_0$ (kHz) |
|---|---|---|---|---|
| 99% Pure Tungsten | 10 | 10 | 0.2 | 11.97 |
| 99% Pure Tungsten | 5 | 10 | 0.1 | 16.93 |
| 99% Pure Tungsten | 19 | 8 | 0.3 | 9.65 |
| 99% Pure Tungsten | 20 | 12 | 1.0 | 11.15 |

In some embodiments, thermal confinement may be achieved if a discharge is produced within a single cycle of a pulsatile voltage waveform, such as within a nanosecond timeframe. From the field of laser-tissue interaction we know that explosive vaporization by nanosecond pulses may produce a peak temperature of ~200° C. and that the volume of the resultant void (or "crater" or "cavity") may be ~50% greater than the substantially heated volume. For example, photodisruption is known to produce such damage volumes. The ejection of vapor and/or water and/or debris from an incised region may preclude the formation of an arc discharge between the electrode and its environment, even at high temperatures; something which a thin deformable electrode may intrinsically provide, especially should said deformable electrode contact tissue along a region that is less than its circumference and produce a void that is larger than the interaction volume, as was described regarding certain effects of photodisruptive nanosecond laser pulses. This extended damage volume may assist in the ejection of debris and/or water and/or vapor. For example, the energy E required to raise a ~Ø10 µm sphere of water from ~20° C. to ~200° C. is E=ρcΔTV→396 nJ. However, a bubble that is smaller than the extent of the electrode may nonetheless provide for a resultant cavity of sufficient extent to allow passage of the entire electrode, such as may be the case with tissue contact along only ~½ to ~⅔ of the electrode circumference (or equivalently, only ~½ to ~⅔ of the electrode diameter, as geometrically projected onto said tissue) due to the increase in the resultant crater volume. The commensurate reduction in energy required to induce a plasma in this case may be $$E^* \sim \frac{2}{3}E \rightarrow 114 nJ$$

and the extent of the resultant crater may be sufficient to accommodate the entire ~Ø10 µm electrode, as may be especially the case for mechanically compliant tissues. By way of non-limiting example, a power of ~15 W may be delivered to an electrode at a pulse repetition frequency ("PRF") of ~1 MHz for an incision width of ~10 mm (or equivalently, an average linear average power density of ~1.5 W·mm$^{-1}$), providing ~15 µJ of energy per cycle (or per "pulse"), for $\tau_{pulse}$=~1 µs. For example, a ~10 mm long, ~Ø10 µm wire electrode operating as described with PRF=~1 MHz and $E_{pulse}$=~15 µJ, an active ablation length per pulse may observe the following relation, $$L_a = \phi \frac{E_{pulse}}{E^*},$$

and $L_\alpha$ may be ~1.32 mm. Furthermore, $L_\alpha$ need not comprise a single contiguous length but may be comprised of separate instances of discrete ablations or discrete ablation regions distributed along an entire electrode length such that the individual lengths of said discontinuous zones (or, equivalently, non-overlapping regions) may sum to about the value of $L_\alpha$ per pulse. Said electrode may also be translated through tissue at an active translation velocity (or "rate") $v_\alpha$ that is at least partially determined by $L_\alpha$, such as $$v_a \approx PRF \frac{\phi}{2} \frac{L_a}{L}.$$

Continuing with the previous exemplary configuration, a total active length of ~1.32 mm along a ~10 mm long, ~Ø10 µm electrode may be translated through tissue with an active translation velocity $v_\alpha$ of ~660 mm·s$^{-1}$ to incise tissue while the electrode may deform as it incises and an actual local peak velocity of at least a single portion of said electrode may be different than $v_\alpha$ due to the velocity of an underlying translation via an actuator, $v_t$, as well as the elasticity of and tension applied to the electrode, as described elsewhere herein. That is, $v_t$ need not be equal to $v_\alpha$. $v_t$ may be chosen to be between ~1 mm·s$^{-1}$ and ~5000 mm·s$^{-1}$. Optionally, $v_t$ may be chosen to be between ~10 mm·s$^{-1}$ and ~1000 mm·s$^{-1}$. Optionally, $v_t$ may be chosen to be between ~50 mm·s$^{-1}$ and ~500 mm·s$^{-1}$. By way of non-limiting example, a ~10 mm long, ~Ø13 µm tungsten wire under ~300 mN of tension operating with PRF=~1 MHz and $E_{pulse}$=~15 µJ may be translated with a peak $V_t$ of ~300 mm·s$^{-1}$ to incise corneal tissue with minimal collateral damage. Considering the foregoing, a system may be configured to allow the electrode velocity to nominally match the tissue velocity using a moving front of plasma-induced bubbles along the length of a deformable electrode that is translated through a tissue to be incised. A variable velocity may be used, as is discussed elsewhere herein.

Figure 4:
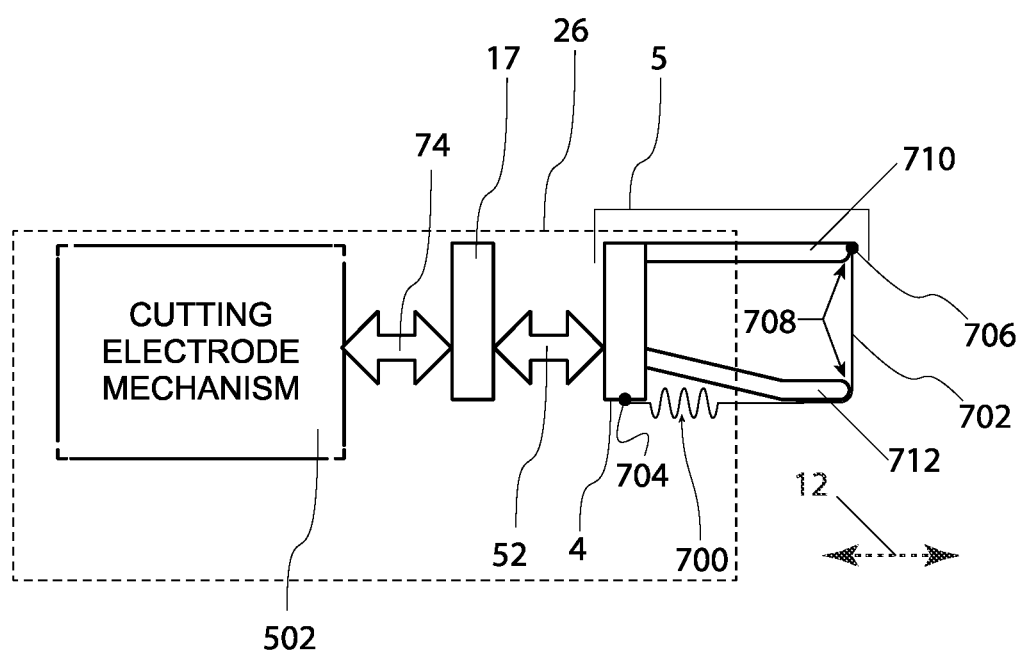
FIGS. 4 and 5 are directed at an electrode subsystem of a system to incise a target tissue structure, in accordance with embodiments of the present disclosure.

FIG. 4 shows a tensioned electrode assembly 5 may comprise tensioning element 700, which in turn may be operatively coupled to electrode 702 and affixed to electrode subassembly 4 via attachments 704 & 706 such that tensioning element 700 allows electrode 702 to flex while in contact with tissue 2 (not shown in the present figure). The incisional portion of electrode 702 may comprise only a portion of the conductive portion of electrode 702. Radii 708 located atop arms 710 & 712 may provide a smooth surface for electrode 702 while it stretches in order to avoid excessive strain as might be imparted at a sharper transition. Arms 710 & 712 may be considered to be at least a portion of a support structure intended to provide mechanical stability to at least a portion of electrode 702. A gap may exist between arms 710, 712, and may serve to receive tissue before and/or during and/or after creating an incision, such as is shown in the instant embodiment. In some embodiments, the tensioned electrode assembly 5 comprises a support structure as described herein.

In some embodiments, a processor, e.g. a controller, is operatively coupled to the elongate electrode to provide movement to the elongate electrode. For example, the processor can be configured with instructions provide to control the actuator and move one or components of the electrode assembly. In some embodiments, the processor is configured with instructions to advance the electrode distally and draw the electrode proximally, for example.

In some embodiments, the elongate electrode is sized for insertion into the tissue, and the processor is configured with instructions to incise the tissue with the electrode to define a volume of incised tissue within a pocket. While the volume can be configured in many ways, in some embodiments the volume comprises a shape profile, e.g., the shape profile of a lenticule. In some embodiments, the processor is configured with instructions to move the electrode with a first movement to define a first incised surface on a first side of the volume of tissue and moved with a second movement to define a second incised surface on a second side of the volume of tissue. In some embodiments, the processor is configured with instructions to advance the electrode distally to define a first surface on a first side of the volume of tissue and to draw the electrode proximally to define a second surface on a second side of the volume of tissue. In some embodiments, a gap extends between the elongate electrode and the support structure, and the gap is sized to receive tissue such that tissue extending into the gap is incised when the electrode is drawn proximally.

In some embodiments, the movement of the electrode is coordinated with the shape of one or more contact plates, in order to define the volume of incised tissue. In some embodiments, the contact plate comprises a first configuration to define a first surface on a first side of the volume of tissue and a second configuration to define a second surface on a second side of the volume of tissue. In some embodiments, a first contact plate comprises a first shape profile to define a first surface on a first side of the volume of tissue and a second shape profile to define a second surface on a second side of the volume of tissue, e.g., first and second surfaces of a lenticule comprising the volume of tissue. In some embodiments, the contact plate comprises a plurality of actuators operatively coupled to the processor, and the processor is configured with instructions to shape the contact plate with a first surface profile for a first incision, and to shape the contact plate with a second profile for a second incision. In some embodiments, processor is configured with instructions to shape the contact plate with the first profile, incise the first side with the first shape profile, shape the contact plate with the second profile, and incise the second side with the second profile, with a total time of no more than about 10 s, for example no more than 5 s, or no more than 2 s, for example.

A support structure may be fabricated, at least partially from a material that is selected from the group consisting of: tungsten, nitinol, steel, copper, brass, titanium, stainless steel, beryllium-copper alloy, cupronickel alloy, palladium, platinum, platinum-iridium, silver, aluminum, polyimide, PTFE, polyethylene, polypropylene, polycarbonate, poly (methyl methacrylate), acrylonitrile butadiene styrene, polyamide, polylactide, polyoxymethylene, polyether ether ketone, polyvinyl chloride, polylactic acid, glass, ceramic, and combinations thereof. Tensioning element 700 may be connected directly to at least a portion of electrode subassembly 4 as shown, or alternately to a at least a portion of a subsequent element to which electrode subassembly 4 is attached; such as coupler 52 or electrode assembly mount 17. By way of non-limiting example, tensioning element 700 may be a spring, a coil spring, a leaf spring, a torsion spring, an elastic mesh, a hinge, a living hinge, and combinations thereof. A deformable electrode may be supported by a support structure and allowed to deform while creating a plasma-induced incision within a target tissue or target tissue structure. An electrode (e.g. electrode 702, or portions thereof) may be at least partially composed of a material selected from the group consisting of: tungsten, nitinol, steel, copper, brass, titanium, stainless steel, berylliumcopper alloy, cupronickel alloy, palladium, platinum, platinum-iridium, silver, aluminum, and combinations thereof. Alternately, an electrode may comprise a wire composed of the same materials just listed. Alternately, an electrode may be coated in certain areas to preclude conduction and/or incision in said areas. Alternately, tubing may be used in lieu of a coating to insulate areas of an electrode. Such a coating or tubing may be selected from the group consisting of: polyimide, PTFE, polyethylene, polypropylene, polycarbonate, poly(methyl methacrylate), acrylonitrile butadiene styrene, polyamide, polylactide, polyoxymethylene, polyether ether ketone, polyvinyl chloride, polylactic acid, glass, ceramic, and combinations thereof. An electrode (e.g. electrode 702) may be a wire having a diameter between ~3 μm and ~300 μm. Alternately, said wire may have a diameter between ~10 μm and ~50 μm. Alternately, said wire may have a diameter between ~12 μm and ~17 μm. Tensioning element 700 may be configured to provide tension of such that the resultant force on an electrode is ~80% of a rated or measured yield strength of the electrode or its material; such as may be the case for a tungsten wire of ~Ø12.5 μm loaded with a tension of ~295 mN, which may also correspond to an elongation of ~0.5%. Optionally, a tensional force may be between ~50% and ~95% of a yield strength. Optionally, a tensional force may be between ~70% and ~85% of a yield strength. Other configurations may be scaled using the relationships relating to the second moment of inertia, as described earlier herein with respect to allowable deflection distances (e.g., ~80% of a rated yield tension force of ~4.7N, or ~3.8N, for a nominally pure tungsten wire with a diameter of ~Ø25 μm. Coupler 52 may be operatively coupled to cutting electrode mechanism 502 via coupler 74. By way of non-limiting example, coupler 74 may be a receptacle configured to accept a disposable module comprised of elements electrode 4, coupler 52, and electrode mount 17 and wherein electrode mount 17 comprises mating features compatible with those of coupler 74 such as threads, a clasp, a snap fitting, and combinations thereof. Cutting electrode mechanism 502 may further comprise mating features compatible with those of couplers 71 & 72, which are themselves mechanically coupled to actuators 50 & 504, respectively, and may provide axes of motion to move electrode subassembly 4 and/or at least a portion of tensioned electrode assembly 5 to create an incision in tissue 2 (not shown). Alternately, by way of non-limiting example, elements electrode subassembly 4, coupler 52, electrode mount 17, cutting electrode mechanism 502, and coupler 74 may be packaged into a probe body 26 as a disposable module configured to engage with a more complete incisional system to actuate said electrode or electrode assembly or probe assembly along axis of motion 12. Although not shown for reasons of clarity, at least portions of probe body 26, including tensioned electrode assembly 5, may be made to move using a translation element to ensure mechanical stability and accuracy along at least a single direction of motion.

Figure 5:
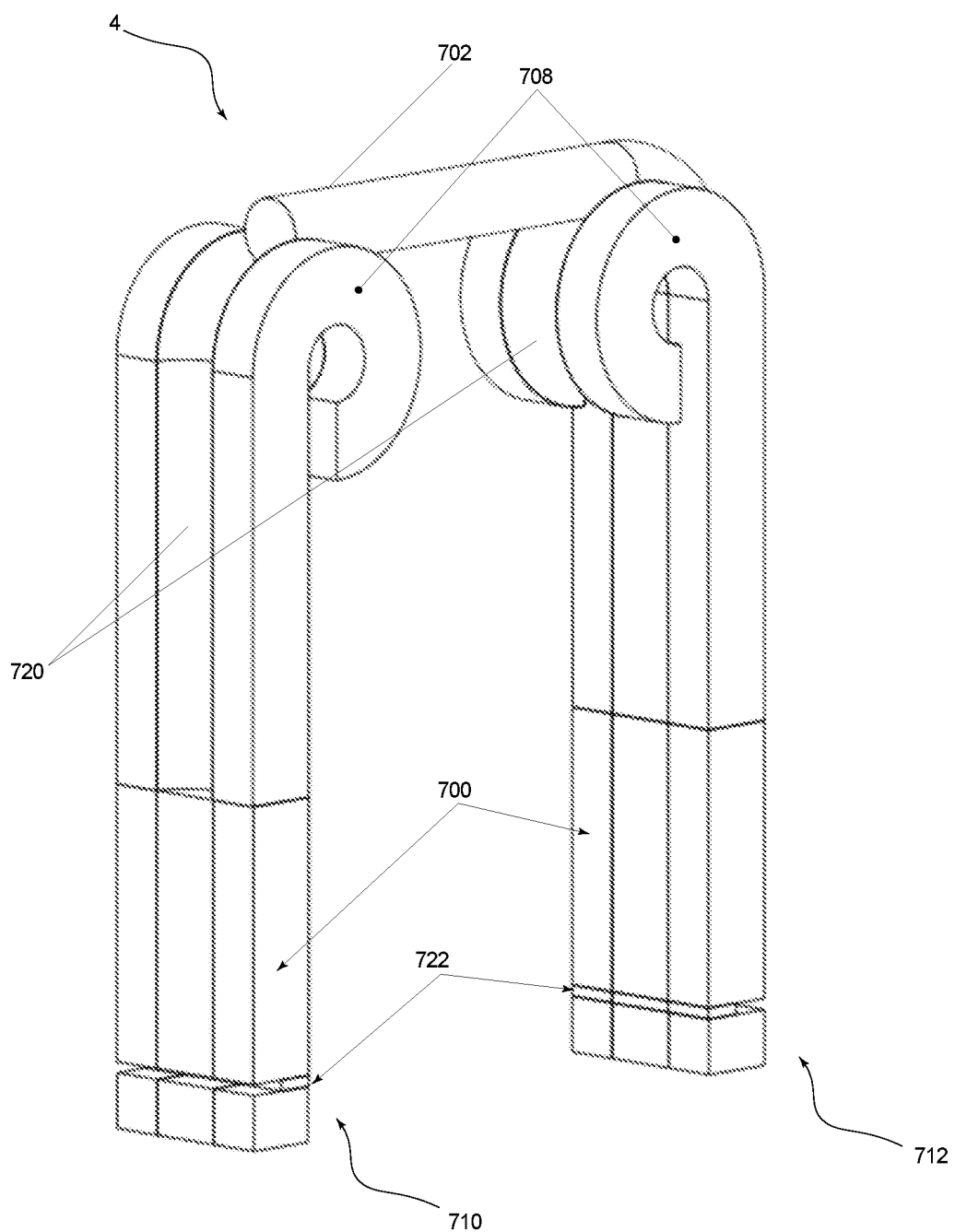

FIG. 5 shows a tensioned electrode assembly 5 similar to that of FIG. 4, wherein radii 708 may further comprise channels 720 into which electrode 702 may be placed to minimize positional errors due to unintentional electrode movement, especially that which is transverse to the intended incision direction. Tensioning element 700 may be configured as a living hinge (or hinges, as shown) within or along arms 710 & 712. Arms 710 & 712 may be comprised of a notched rigid material, as shown to provide living hinge 722. By way of non-limiting example, a suitable material for creating a living hinge may be selected from the group consisting of: polyethylene, polypropylene, polycarbonate, poly(methyl methacrylate), acrylonitrile butadiene styrene, polyamide, polylactide, polyoxymethylene, polyether ether ketone, polyvinyl chloride, copper beryllium, and combinations thereof. In the case where living hinge 722 is integral to an arm 710 or 712 and an electrically conductive material may be chosen and such cutting electrode may be soldered, brazed, adhered with an electrically conductive adhesive, and/or welded to the arm(s). In the case where a living hinge is integral to an arm 710 or 712 and an electrically insulating material is chosen, electrode 702 may be otherwise adhered to the arm, or be soldered, brazed, and/or welded to an adjacent conductive material.

Figure 6:
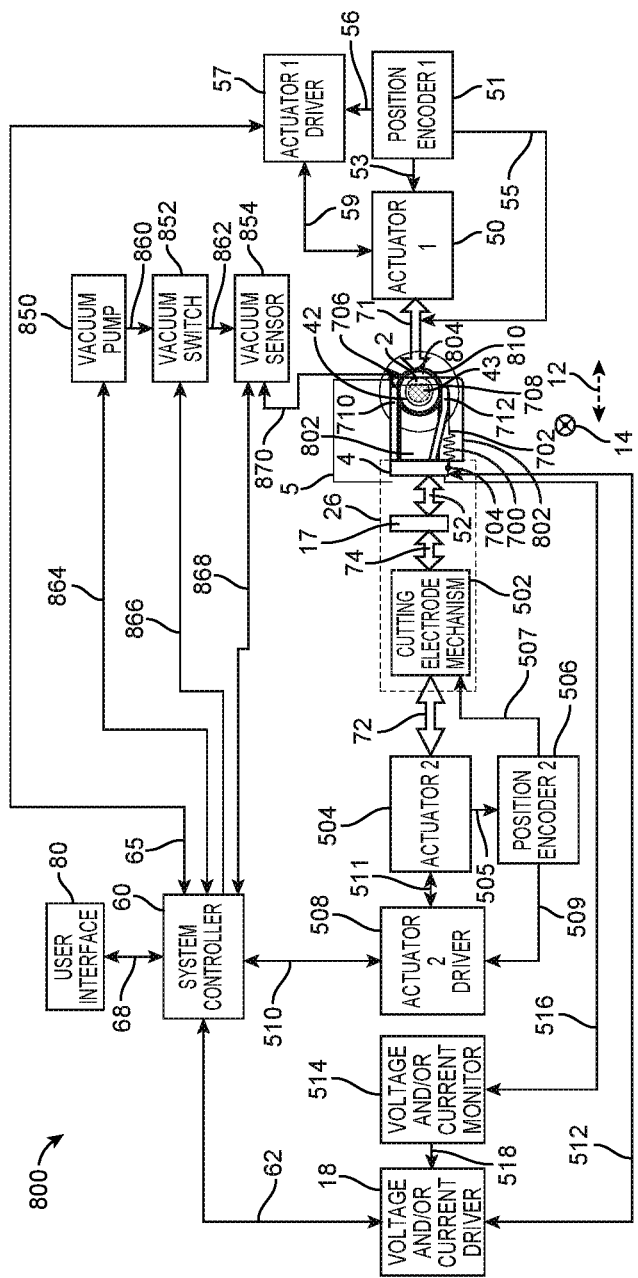
FIG. 6 is directed at a system to incise target tissue structure, in accordance with embodiments of the present disclosure.

FIG. 6 shows a system to incise tissue; such as ocular tissue, including corneal, limbal, and stromal tissue, system 800. System 800 may comprise a tensioned electrode assembly 5 similar to that of FIGS. 4 and 5. Electrode subassembly 4 may be coupled to electrode mount 17 via coupler 52. By way of non-limiting example, coupler 52 may be made to be at least partially electrically insulated. Electrode subassembly 4 may comprise arms 710 & 712, electrode 702, and tensioning element 700, which may be operatively coupled to electrode 702 and affixed via attachments 704 & 706 to create tensioned electrode assembly 5 such that tensioning element 700 may allow electrode 702 to stretch while in contact with tissue 2. Attachments 704 and/or 706 may be achieved via soldering, brazing, adhering, compression fitting, clamping, and combinations thereof. Radii 708 located atop arms 710 & 712 may provide a smooth surface for electrode 702 while it stretches in order to avoid excessive strain as might be experienced at a sharper corner. Tensioning element 700 may be connected directly to an electrically conductive portion of electrode 4, or alternately to a subsequent element to which to comprise electrode 702; such as coupler 52 or electrode mount 17. An incision may be made by moving along axis of motion 12. In the instant exemplary configuration, tensioned electrode assembly 5 may be comprised of elements 700, 702, 704, 706, 708, 710, and 712; all of which may be at least partially constructed from an at least a partially conductive material and thus may be held at about the same voltage by driver 18 (not shown) and all of which may be considered to comprise tensioned electrode assembly 5. Alternately, electrode subassembly 4 and tensioned electrode assembly 5 may be the same. Alternately, some of the aforementioned elements may be comprised at least partially of an electrically insulating material and thus may not be at the same electrical potential as the other elements comprised of at least partially electrically conductive material and electrode subassembly 4 may be considered to be only those elements comprising an at least partially electrically conductive material and be a subsystem of a tensioned electrode assembly 5, as shown. By way of non-limiting example, tensioning element 700 may be a spring, a coil spring, a leaf spring, a torsion spring, an elastic mesh or web, a hinge, a living hinge, and combinations thereof. A torsion spring may be such as that found in a staple remover. By way of non-limiting example, an at least partially electrically conductive electrode material may be selected from the group consisting of: tungsten, nitinol, steel, copper, brass, titanium, stainless steel, beryllium-copper alloy, cupronickel alloy, palladium, platinum, platinum-iridium, silver, aluminum, and combinations thereof. Alternately, an electrode 702 may be at least partially comprised a wire composed of the same material. Alternately, an electrode subassembly 4 may be at least partially comprised of elements composed of electrically insulating materials. Alternately, an electrode subassembly 4 may be coated in certain areas to preclude conduction and/or incision in said areas. Similarly, tubing may be used in lieu of a coating to insulate areas of an electrode assembly. By way of non-limiting example, such a coating or tubing may selected from the group consisting of: polyimide, PTFE (e.g., Teflon), polyethylene, polypropylene, polycarbonate, poly(methyl methacrylate), acrylonitrile butadiene styrene, polyamide, polylactide, polyoxymethylene, polyether ether ketone, polyvinyl chloride, polylactic acid, glass, ceramic, and combinations thereof. A return electrode (not shown) may be placed on or near the eye of the patient and connected to driver 18. A serial load of between ~1500Ω and ~5000Ω may be placed in-line with the electrode in order to provide for current limitation. Coupler 52 may be operatively coupled to cutting electrode mechanism 502 via coupler 74. Alternately, by way of non-limiting example, elements electrode 4, coupler 52, electrode mount 17, cutting electrode mechanism 502, coupler 74, or a subset thereof may be packaged into a probe body 26 as a disposable module configured to engage system 800 via couplers 71 & 72, which in turn may comprise mating features compatible with those of actuators 50 & 504, respectively; such as threads, a clasp, a snap fitting, and combinations thereof. Actuator 50 may provide an axis of motion (or equivalently, a "translation" along a direction of motion, e.g., axis of motion 14) be coupled to position encoder 51 via connection 53 and both position encoder 51 and actuator 50 may be connected to a translation device and/or actuator driver 57 via connections 55 & 59, respectively. By way of non-limiting example, connections 55 & 507 may comprise at least one of the following, a mechanical coupler, an electrical coupler, a magnetic coupler, and an optical coupler. Actuator 504 may also provide an axis of motion (e.g. axis of motion 12) and be coupled to position encoder 506 via connection 505 and both position encoder 506 and actuator 504 may be connected to actuator driver 508 via connections 509 & 511, respectively. It should be noted that only a single axis of motion may be relied on to practice certain embodiments of the present disclosure, such as in the creation of a corneal flap utilizing a single incision. The axes of motion for actuators 50 & 504, axes of motion 14 & 12, respectively, may be configured to be orthogonal or at least not colinear. Actuators 504 & 50 may be configured to actuate tensioned electrode assembly 5, or portions thereof, along axes of motion 12 & 14. Position encoders 51 & 506 may be mechanically coupled, via connections 55 & 507, respectively, to the module onto which electrode subassembly 4 is mechanically coupled in order better provide reliable position information than non-collocated sensors may provide. Alternately, Actuator 50 may be configured to correspond to (or, "move along") axis of motion 14 and be made to actuate (or "translate") a contact plate 804 and connection 55 may be made with contact plate 804, or structure supporting contact plate 804. Driver 18 may be configured to provide controlled voltage and/or controlled current to electrode 4. Driver 18 may provide an alternating voltage and/or current waveform to electrode 702. The type of such a waveform may be, by way of non-limiting examples; selected from the group consisting of: pulsatile, sinusoidal, a square, sawtooth, triangular, fixed frequency, variable frequency, and combinations thereof. Driver 18 may be configured to supply a waveform with a peak-to-peak full range voltage of between ~50V and ~1000V. Alternately, driver 18 may be configured to supply a waveform with a peak-to-peak full range voltage of between ~200V and ~500V. Driver 18 may be configured to supply a waveform with a carrier (or "base") frequency of between ~10 kHz and ~10 MHz. Alternately, driver 18 may be configured to supply a waveform frequency of between ~500 kHz and ~2 MHz. Alternately, driver 18 may be configured to supply a waveform frequency of between ~800 kHz and ~1.2 MHz. A burst duration may also be used and may further depend on the electrode velocity, $v_t$. Driver 18 may be further modulated to comprise bursts of pulses at a modulation frequency of between ~100 Hz and ~3 MHz to create a duty cycle. The duty cycle may be between ~0.01% and ~100%. Alternately, the duty cycle may be between ~50% and ~100%. Alternately, the duty cycle may be between ~95% and ~100%. Driver 18 may be configured to supply an average power of between ~1 W and ~25 W. Alternately, driver 18 may be configured to supply an average power of between ~12 W and ~18 W. Driver 18 may be configured to supply an energy per cycle (or, equivalently, an "energy per pulse") of between ~1 µJ and ~100 µJ. Alternately, driver 18 may be configured to supply an energy per cycle of between ~5 µJ and ~50 µJ. Alternately, driver 18 may be configured to supply an energy per cycle of between ~10 µJ and ~20 µJ.

In some embodiments, a flap may be described as an incision yielding a "flap" of tissue that may be lifted and pivot on a "hinge" to provide access to the tissue beneath it. By way of non-limiting example, cutting a segment of tissue to depth of 130 µm and razing a plane at that depth beneath a tissue surface may yield a flap with an uncut edge as its hinge. A flap may be amputated by completing the uncut edge of the exemplary incision. In some embodiments, a pocket may be described as an incision that separates a first depth (or layer) of tissue from a second depth (or layer) of a segment of tissue without necessarily creating a flap. By way of further non-limiting example, cutting one side of a tissue to a depth and razing a plane at that depth beneath a tissue surface may yield a pocket.

In some embodiments, significant drops of the input impedance of driver 18 due to plasma discharge at electrode 702 may cause local current spiking, which in turn may destroy the electrode and/or cause damage tissue. The power delivered (or, equivalently "delivered power", or equivalently "maximum power output") to the electrode may be limited instead to avoid such situations. An average power suitable for practicing embodiments of the present disclosure may be between ~1 W·mm$^{-1}$~10 W·mm$^{-1}$, especially during glow discharge. The delivered power may be higher during the initial exposure to better ensure commencement of dielectric breakdown. Alternately, a voltage and/or current waveform (or alternately, a power control signal) used to power said electrode 702 may be further modulated, or adjusted, such that it is proportional to the instant or expected length of tissue engagement and/or the electrode translation velocity, $v_t$.

By way of non-limiting example, when incising a cornea, a voltage may be increased from an initial value that corresponds to when electrode 702 is about to initially engage, or initially engages, or is expected to initially engage the tissue and is nominally directed towards a region of more central cornea to a higher voltage that corresponds to when electrode 702 is traversing or expected to traverse the central cornea and thus have a relatively greater length of tissue engagement than it did initially; said electrode voltage may be then made to decrease as electrode 702 continues traversing cornea 2 and incising tissue with inherently less engagement length, said decrease may be configured to be the opposite of the initial increase, but need not be. The position of an electrode 702 within a cornea 2 may be inferred using an encoder in the translation subsystem, as described elsewhere herein. In an embodiment, the voltage provided by driver 18 may be configured to deliver a maximum peak-to-peak bipolar nominally sinusoidal voltage of ~500V (comprising both ~+250V and ~-250V amplitudes, relative to a nominal neutral voltage, which need not be a ground voltage) with a PRF (or "carrier frequency") of ~1 MHz that may ramp from ~0V to maximum amplitude during the initial ~50 µs of a translation and then may ramp back to ~0V during the final ~100 µs of a translation, such as may be useful when tensioned electrode assembly 5 is comprised of an ~10 mm long, ~Ø10 µm, ~99.99% pure tungsten wire for the incisional portion of electrode 702 that is tensioned to ~300 mN by tensioning element 700 and translated at a maximum rate (i.e., $V_t$, max) of ~300 mm·s$^{-1}$ along direction 12 with a constant acceleration of ~2,000 mm·s$^{-2}$ with an initial electrode location that is between ~4 mm and ~7 mm from the closest aspect of the target tissue to be incised. It is to be noted that such a constant acceleration may yield a linear velocity profile in which an electrode may be brought to rest inside of the target tissue, such as may be required to create a flap or a lenticule as opposed to a complete incision, as will be described elsewhere herein.

In some embodiments, monitor 514 may be configured to monitor the voltage and/or current suppled to electrode 702 via connection 516 and provide data regarding said voltage and/or current to driver 18 via connection 518. The data regarding voltage and/or current of electrode 702 may be in the form of signals from a comparator. System controller 60 may be operatively coupled to driver 18 via connection 62, which is at least a unidirectional connection. Alternately, connection 62 may also be a bidirectional connection wherein controller 60 is able to sense and/or respond to at least a signal from driver 18. Signals from monitor 514 may be also provided to system controller 60 and acted upon thereby to control the incision created by electrode 702. Monitor 514 may reside within system controller 60, and/or communicate with system controller 60 via driver 18. Such a signal may be a safety signal related to a sensed voltage or current, such as when said voltage or current is outside of prescribed bounds. In a further alternate embodiment, driver 18 and/or monitor 514 may provide feedback to controller 60 or use such feedback internally. Such feedback may be, by way of non-limiting example, EMF or current feedback and may be useful in determining when electrode 702 contacts tissue and/or the status of the plasma. Such status may be, for example, whether or not the plasma in the glow discharge regime or not. Connection 65 connects controller 60 with actuator 50 and is at least a unidirectional connection. Actuator 50 may be comprised of at least one electrical motor and may further comprise a positional encoder. Connection 65 may alternately be a bidirectional connection wherein signals are shared between controller 60 and actuator 50, such as position, velocity, acceleration, out of bounds errors, etc. In a further alternate embodiment, actuator 50 may provide feedback to controller 60 or use such feedback internally and may share such feedback as signals with controller 60. Such feedback may be, by way of non-limiting example, force feedback and may be useful in determining when electrode 702 contacts tissue or when it imparts excessive force on the tissue to be incised. Likewise, connection 67 connects controller 60 with power supply 70 and is at least a unidirectional connection. In a further alternate embodiment, power supply 70 may provide feedback to controller 60 or use such feedback internally and may share such feedback as signals with controller 60. Such feedback may be, by way of non-limiting example, an error signal. Such error signals may be temperature errors, input voltage errors, output voltage errors, input current errors, output current errors, etc. Likewise, connection 68 connects controller 60 with user interface 80 and is at least a unidirectional connection from user interface 80 to controller 60. In a further alternate embodiment, user interface 80 may provide feedback to controller 60 or use such feedback internally and may share such feedback as signals with controller 60. For example, user interface 80 may be a graphical user interface or a button or a foot pedal used to signal actuator 50 to move electrode subassembly 4 and/or tensioned electrode assembly 5 and incise tissue. Actuator drivers 57 & 508 may be connected to system controller 60 via connections 65 & 510, respectively. User interface 80 may be connected to system controller 60 via connection 68 and user instructions sent therethrough.

In some embodiments, the system controller 60 comprises a processor configured with instructions to determine a profile of tissue to be removed from the eye to provide refractive correction. The processor can be configured to determine the shape profile of one or more plates used to provide a refractive correction for the patient. Also, although reference is made to controller 60, controller 60 may comprise a component of a distributed computing system and may be operatively connected to one or more processors as described herein, such as a distributed processing system.

In some embodiments, system 800 may further comprise contact plate 804, a support element 802, a suction element 810, and accompanying vacuum apparatus which may be used to fixate a contact tissue 2. An incision 42 may be made in tissue 2 (the cornea and/or corneal stroma in the instant exemplary embodiment) by moving at least portions of tensioned electrode assembly 5 along axis of motion 12 to create bed 43 using actuator 504. A contact plate 804 may be incorporated to applanate the cornea by moving it onto the anterior surface of the cornea along axes of motion 14 by means of actuator 50. Contact plate 804 may further comprise a contact surface 806 (not shown for clarity). Said contact plate 804 may be used to applanate the cornea, especially when contact surface 806 is nominally about planar. By way of non-limiting example, contact plate 804 may be configured to be a planar glass window to allow visibility therethrough. By way of non-limiting example, contact plate 804 may be composed of a material selected from the group consisting of: glass, crystalline, ceramic, metal, polymer, and combinations thereof. A contact element 808 (not shown) may be placed on the distal surface of contact plate 804 to provide a clean and/or sterile surface for contact with tissue 2 and may be configured as a thin, conformal, peel-and-stick sterile barrier, which may also be disposable. By way of non-limiting example, contact element 808 may be composed of a material selected from the group consisting of: polyethylene (PE), polyvinylchloride (PVC), polypropene (PP), oriented PP (OPP), biaxially oriented PP (BOPP), polyethylene terephthalate (PET), and combinations thereof. Contact plate 804 may be supported, at least in part, by support 802. Support 802 may further at least partially support elements of tensioned electrode assembly 5, such as arms 710 & 712 and thereby also supporting electrode 702 and tensioning element 700 to form a at least a portion of electrode subassembly 4 and/or tensioned electrode assembly 5. As such, arms 710 & 712 may be considered to be a support structure for electrode 702. Alternately, support 802 may be operatively coupled to probe body 26 and/or sheath 16. Alternately, contact plate 804 may be made to move along with support 802 relative to tissue 2. A suction element 810 may be used to stabilize the eye containing tissue 2 relative to contact plate 804 and/or electrode 4. Suction element 810 may be configured as a nominally open annular ring, as shown, or alternately by any other applicable construction to achieve fixation to the eye, such as a single open pocket, or a plurality of open pockets. Suction element 810 may be operatively coupled to vacuum pump 850 via vacuum line 870 to provide a negative pressure within suction element 810. For patient safety and system reliability, a vacuum switch 852 and/or a vacuum sensor 854 may be placed in between suction element 810 and vacuum pump 850, and connected via connections 860 and 862, respectively. System controller 60 may be connected to vacuum pump 850, vacuum switch 852, and vacuum sensor 854 via electrical connections 864, 866, and 868, respectively. In the instant configuration, actuator 50 may be configured to correspond to axis of motion 14 and be made to actuate (or "translate") a contact plate 804 and connection 55 may be made with contact plate 804, or such structure supporting contact plate 804. Contact plate 804 may be translated at a rate, or velocity of between ~0.1 mm·s$^{-1}$ and ~1000 mm·s$^{-1}$, and in an alternate embodiment it may be translated at a rate of between ~10 mm·s$^{-1}$ and ~100 mm·s$^{-1}$. The motion corresponding to actuator 50 may be configured to be at least partially simultaneous with of actuator 504, or the velocity profiles thereof.

In some embodiments, system 800 may be further configured such that a tensioned electrode assembly 5 that at least partially comprises an electrode 702. Electrode 702 may comprise a tungsten wire of ~12.5 μm in diameter and at least ~99% purity that runs across arms 710 & 712 to form a bridge distance of ~12 mm and uses a mechanical coil spring imparting a tensional force of ~300 mN on electrode 702, for example.

Figure 7:
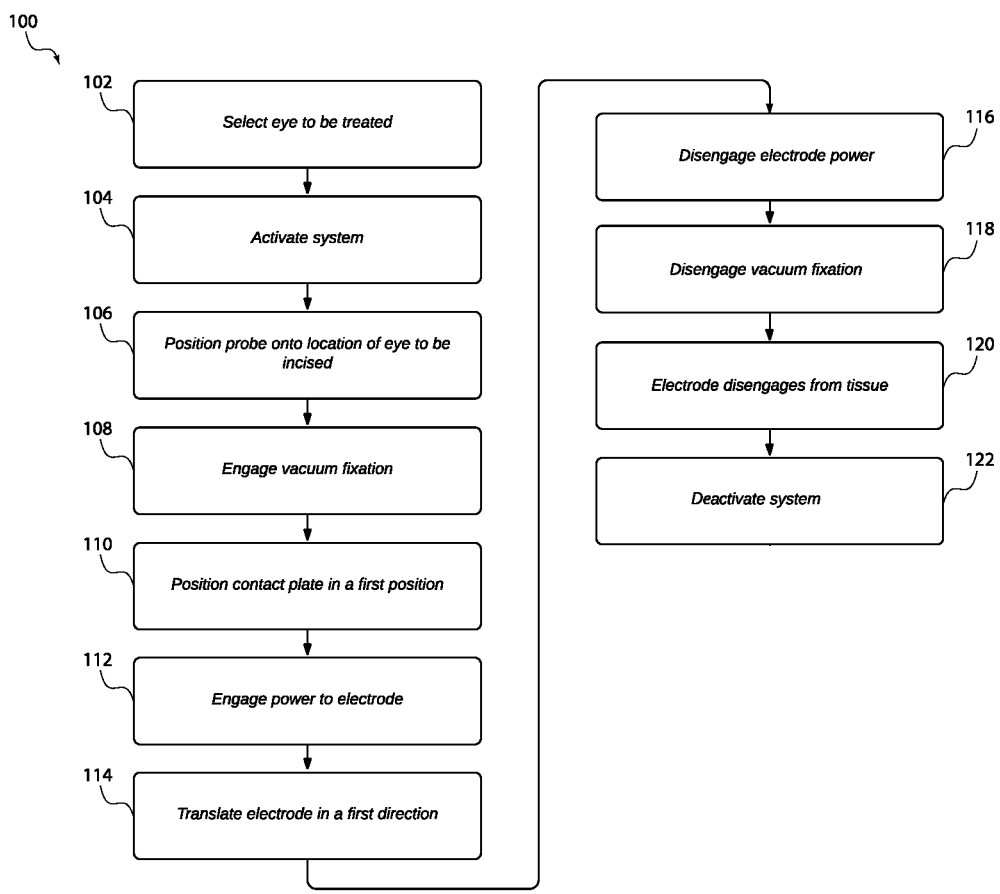
FIG. 7 depicts a flow chart describing steps to practice a method, in accordance with embodiments of the present disclosure.
Figure 9:
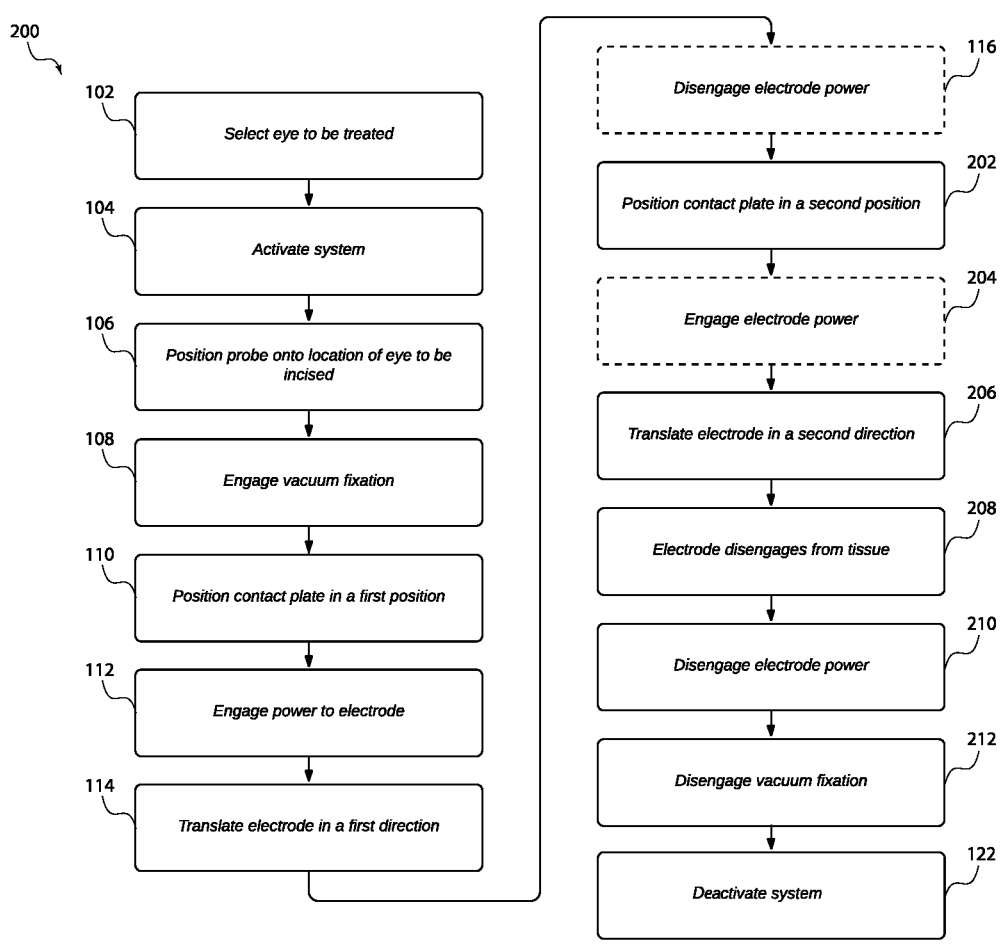
FIG. 9 depicts a flow chart describing steps of a method, in accordance with embodiments of the present disclosure.

In some embodiments, an incision may form a flap or a pocket or combinations thereof based upon whether or not the electrode cutting width is about greater than or about equal to the lateral extent of the target tissue structure to be incised and whether or not the electrode is made to penetrate outwards laterally from the tissue. That is, a flap may be made in an anterior aspect of a cornea by applanating or otherwise compressing said anterior corneal surface using contact plate 804 to yield a lateral dimension for incision 42 of between ~3 mm and ~11 mm, or alternately of between ~8 mm and ~10 mm, all of which may be less than the aforementioned bridge distance to provide a flap incision. A flap incision may be configured to provide a D-shaped incision 42, as shown, where the straight segment of the D-shaped incision may be a hinge portion. Similarly, a pocket incision may be made if the electrode bridge distance is less than the lateral extent of the compressed cornea presented to the electrode. Alternately, a combination flap/pocket incision may be created using a pocket incision configuration and allowing the electrode to traverse the entire distance through the cornea and may yield an incision shaped as a fully-rounded rectangle, or a partially-rounded rectangle (e.g. when configured to comprise a straight uncut portion). In an alternate embodiment, driver 18 may be configured to supply a sinusoidal waveform that may have a peak-to-peak full range voltage of ~250V at a frequency of ~1 MHz and a power limit of ~15 W to incise corneal tissue at an electrode translation rate of between ~200 mm·s$^{-1}$ and ~0 mm·s$^{-1}$ (i.e. V$_t$=~0 mm·s$^{-1}$ while electrode is stopped at end of incision) along direction of motion 12 and utilizing steps 102 through 122 of flowcharts 100 & 200, as shown in FIGS. 7 and 9. Step 202 of flowchart 200 may be utilized for the discontinuation of power to an electrode in coordination with the motion of the electrode and contact plate 804 such that the electrode is provided a voltage of nominally ~0V during the interim period between the electrode moving in a first direction and then moving in a second direction, such as might be the case if contact plate 804 is moved along direction of motion 14 in order to remove a portion of tissue (e.g. a "lenticule" of intrastromal tissue). Alternately, the electrode voltage and/or power may be made a function of the electrode velocity, and/or position, and/or cutting extent, as described elsewhere herein.

Alternately, a variable acceleration may be utilized to create a motion profile for an electrode, resulting in a nonlinear velocity profile. Such a motion profile may require a higher order control model and incorporate "jerk" and/or "snap" and/or "crackle" and/or "pop" factors to provide an asymmetrical acceleration/deceleration such that the range of v$_t$ in the initial ~50 μs is similar to that of the final ~10 μs, by way of non-limiting example.

The velocity and/or velocity profile and/or the active incision width may be taken into account when controlling (e.g., "modulating") the power to the electrode.

By way of non-limiting example, the power to an electrode 702 may be adjusted by choosing a maximum value of a parameter selected from the group consisting of: a voltage, a current, a carrier frequency, a modulation frequency, a duty cycle, a power setpoint, a power limit, an energy per pulse setpoint, an energy per pulse limit, and combinations thereof.

By way of non-limiting example, a modulation relationship describing the controlled power output of an electrode 702 driven by driver 18 may be selected from the list comprised of the following; a fixed relationship, a constant relationship, a linear relationship, a nonlinear relationship, a logarithmic relationship, a sinusoidal relationship, an exponential relationship, a polynomial relationship, and combinations thereof. Said relationships may be direct or inverse, depending upon the immediate system configuration and determinable using the descriptions and equations included herein. Said controlled power output may be considered to be the instantaneous power and/or the average power and/or the peak power. Said modulation may be achieved via control of driver 18, by way of non-limiting example. The term modulation is used herein to indicate an alteration of an otherwise consistent output, waveform, or signal. As used herein, "modulating" a waveform is equivalent to "enveloping" a waveform and "modulation envelope" is equivalent to "envelope." Alternately, no modulation may be used to envelope a waveform, including an intrinsically pulsatile waveform.

By way of non-limiting example, when creating a corneal flap incision, a duty cycle Dc may be modulated by utilizing a compound relationship representing the active incision width y$_\alpha$ which may be modeled as a chord length of a circle of radius R that is turn a function of the distance into the target tissue x$_c$ (i.e., the height of the circular cap) multiplied by the velocity profile v$_t$ to yield $$D_c \propto v_t y \rightarrow 2v_t [x_c(2R - x_c)]^{\frac{1}{2}},$$

which may be normalized using the nominal values for R and V$_t$,max to provide a generic envelope function.

Alternately, the voltage U required for vaporization may be regarded as $$U = r_e \sqrt{\frac{\rho C \Delta T \gamma}{\tau} \ln\left(\frac{L}{r_e}\right)},$$

and at least a component of a modulation relationship for electrode voltage V provided by driver 18 to an electrode 702 may be V∝√ln(ya)·2√x$_c$(2R−x$_c$)/√2. It should be noted that the preceding examples at least partially involve exponential relationships, as the radical is the inverse function to the of taking of a power.

Alternately, an energy per cycle provided by driver 18 to an electrode 702 may be configured to deliver an energy per cycle that may be at least partially dependent on the value of v$_t$ and/or at least partially dependent on the value of the active incision width y$_\alpha$.

Alternately, a duty cycle provided by driver 18 to an electrode 702 may be configured to deliver a duty cycle that may be at least partially dependent on the value of V$_t$ and/or at least partially dependent on the value of the active incision width y$_\alpha$.

Alternately, a voltage provided by driver 18 to an electrode 702 may be configured to deliver a voltage that may be at least partially dependent on the value of v$_t$ and/or at least partially dependent on the value of the active incision width y$_\alpha$.

Alternately, a current limit provided by driver 18 to an electrode 702 may be configured to deliver a current limit that may be at least partially dependent on the value of v$_t$ and/or at least partially dependent on the value of the active incision width y$_\alpha$.

Alternately, a power limit or setpoint provided by driver 18 to an electrode 702 may be configured to deliver a power limit or setpoint that may be at least partially dependent on the value of $v_t$ and/or at least partially dependent on the value of the active incision width $y_\alpha$.

Alternately, a PRF provided by driver 18 to an electrode 702 may be configured to deliver a PRF that may be at least partially dependent on the value of $v_t$ and/or at least partially dependent on the value of the active incision width $y_\alpha$.

Alternately, $v_t$ may be at least partially dependent upon the active incision width $y_\alpha$ and/or $x_c$, where $y_\alpha = 2\sqrt{x_c(2R-x_c)}$, as described elsewhere herein.

Alternately, such as may be useful when tensioned electrode assembly 5 is comprised of an ~10 mm long, ~⌀20 μm, ~99.99% pure tungsten wire for the incisional portion of electrode 702 that is tensioned to ~300 mN by tensioning element 700 and translated at a maximum rate of ~200 mm·s$^{-1}$ along direction 12 with a constant acceleration of ~1,000 mm·s$^{-2}$ with an initial electrode location that is between ~2 mm and ~4 mm from the closest aspect of the target tissue to be incised (i.e., the point nearest the electrode along its axis of motion), a voltage provided by driver 18 may be configured to deliver a maximum peak-to-peak bipolar nominally sinusoidal voltage of ~600V (comprising both ~+300V and ~−300V amplitudes, relative to a nominal neutral voltage) with a PRF (or "carrier frequency") of ~1 MHz that linearly ramps from ~0V to maximum amplitude during the initial ~50 μs of a translation and ramps back to ~0V during the final ~50 μs of a translation.

In a further alternate embodiment, a duty cycle provided by driver 18 may be configured to deliver a duty cycle that ramps from ~0% to maximum amplitude of between ~70% and ~100% during the initial ~50 μs of a translation and ramps back to ~0% during the final ~10 μs of a translation. Said duty cycle may be created utilizing a modulation frequency, such as a square-wave gating function. Said square-wave gating function may be configured to have variable "on" and/or "off" times. The relationship of the variable "on" and/or "off" times may be as described elsewhere herein regarding the relationships for describing the controlled power output of an electrode.

In a further alternate embodiment, a duty cycle provided by driver 18 may be configured to deliver a duty cycle that may be at least partially dependent on the value of $V_t$ and may ramp from ~0% to maximum amplitude of between ~70% and ~100% while the velocity of the electrode is increased from rest (i.e. $V_t=0$ mm·s$^{-1}$) to its maximum value and the duty cycle is then decreased to ~0% when the electrode velocity is reduced back to rest.

In a further alternate embodiment, the maximum power output provided by driver 18 may be configured to deliver a maximum power output that is that may be at least partially dependent on the value of $v_t$ and may ramp from ~0% to maximum amplitude of between ~70% and ~100% while the velocity of the electrode is increased from rest to its maximum value and the maximum power output is then decreased to ~0% when the electrode velocity is reduced back to rest.

In a further alternate embodiment, a voltage provided by driver 18 may be configured to deliver a voltage that may be at least partially dependent on the value of $v_t$ and may ramp from ~0% to maximum amplitude of between ~70% and ~100% while the velocity of the electrode is increased from rest to its maximum value and the duty cycle then decreased to ~0% when the electrode velocity is reduced back to rest.

FIG. 7 describes a method of incising tissue. Flowchart 100 comprises steps 102-122 that may be completed serially, or in any suitable order. At a step 102 an eye is selected for treatment. Step 104 involves activating the system, and step 106 involves positioning a probe onto the tissue to be treated. Step 108 involves activating a vacuum system to fixate tissue with respect to the probe (such as via the vacuum system described earlier). Step 110 involves positioning a contact plate onto the tissue in a first position. Step 112 involves power being applied to an electrode. Step 114 involves translating (or "moving" or "actuating") said electrode in a first direction (such as along axis of motion 12, the "+x-direction"). Step 116 involves discontinuing power to the electrode. Step 118 involves disengaging the vacuum fixation and freeing the tissue and disengaging the eye being treated. Step 120 involves an electrode disengaging from a tissue just incised. Step 122 involves deactivating the system and disengaging it from the eye. A thin electrode may be allowed to break as the system is disengaged from the patient. Alternately said electrode may be made to translate in a second direction, nominally opposite of said first direction. Alternately, step 108 and step 110 can be exchanged, and power applied to the electrode once it is in contact with tissue 2. Alternately, steps 116 through 120 may be eliminated to create an excision. Alternately, steps 116 & 118 may be eliminated if there is only low risk of collateral damage due to tissue heating while the actuator changes direction. Alternately, step 116 may involve a tapered reduction in power to the electrode, and step 112 may involve a tapered increase in power to the electrode, as described elsewhere herein.

Although FIG. 7 shows a method of incising tissue in accordance with some embodiments, one of ordinary skill in the art will recognize that many adaptations and variations can be made in accordance with the present disclosure. For example, the steps can be performed in any suitable order, some of the steps repeated, some of the steps omitted, and combinations thereof.

In some embodiments, a processor as described herein is configured with instructions to perform one or more of the steps of the method of FIG. 7.

Figure 8A:
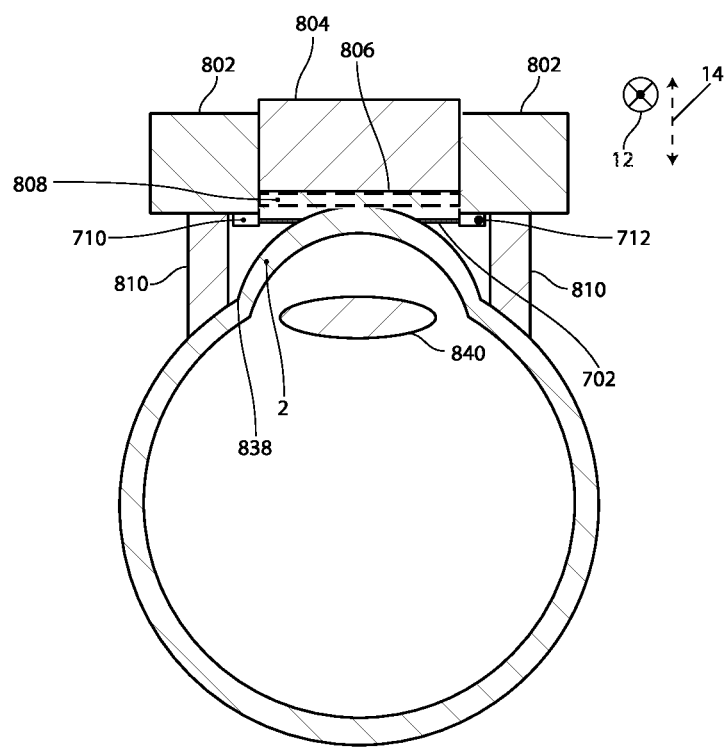
FIGS. 8A through 8D are directed at a system to incise a target tissue structure, in accordance with embodiments of the present disclosure.

FIGS. 8A through 8D are directed at details in accordance with embodiments of the present disclosure, wherein a tensioned electrode assembly 5 is now shown in a view orthogonal to that of FIGS. 4 through 6, such that axis of motion 12 may now be into and out of the plane of the figure, while axis of motion 14 may be vertical, and wherein the steps of FIG. 7 may be followed. FIG. 8A shows that contact plate 804 may be configured to lie within a middle portion of support 802 and move relative to support 802 along axis of motion 14. Contact surface 806 of contact plate 804 may be about planar and about parallel to the cutting portion of electrode 702. Electrode 702 is shown as being initially behind the cornea in this view. Contact element 808 may be placed on contact surface 806 to create a sterile disposable for use only during a single procedure. Contact element 808 may nominally conform to at least a portion of contact surface 806. The portion of contact surface 806 to which contact element 808 conforms may be a center portion. Suction element 810 may be configured to contact the eye containing tissue 2 at a region nearby the outer cornea and/or the corneoscleral limbus 838, as shown, to fixate and stabilize cornea 843 (not indicated in the present figure). Alternately, suction element 810 may be made to contact at least an aspect of cornea 843 to better stabilize tissue 2 relative to the incision of electrode 702. Cornea 843 may comprise anterior corneal surface 842 and posterior corneal surface 844. In this instance, target tissue 2 may be considered to be stromal tissue within cornea 843 and contained between anterior corneal surface 842 and posterior corneal surface 844. Intraocular lens 840 is shown for the purposes of orientation and may be a natural lens or a prosthetic lens. In the present embodiment, contact element is in contact with the apex of anterior corneal surface 842 of cornea 843. Tensioned electrode assembly 5 may comprise arms 710 and 712, as well as electrode 702, as shown. The configuration of the immediate figure may represent steps 102, 104, and 106 of FIG. 7.

Figure 8B:
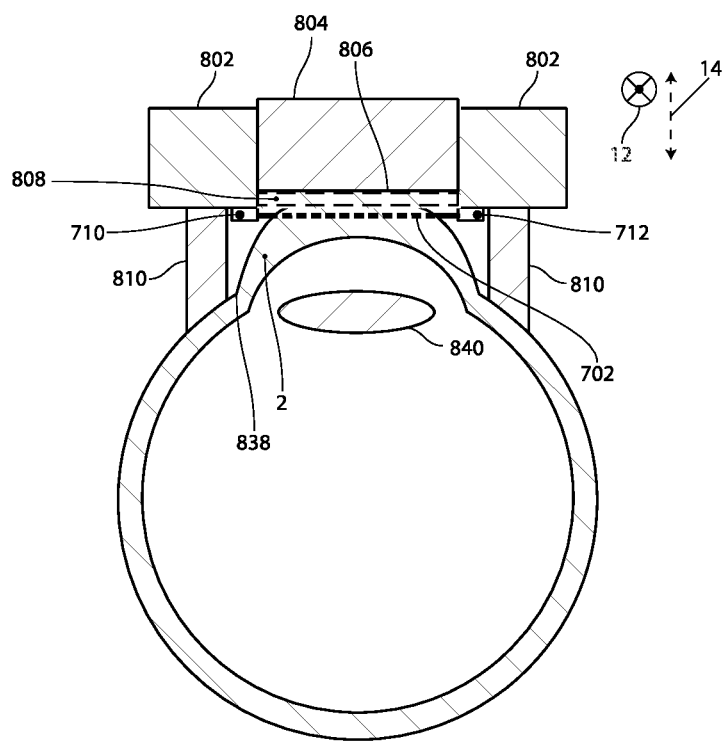

FIG. 8B shows the system of FIG. 8A, wherein contact plate 804 and therefore contact element 808 may have been moved farther along axis of motion 14 to applanate cornea 843 and tissue 2 therein. Electrode 702 may be made to incise tissue 2 by traversing a path along axis of motion 12, as has been described elsewhere herein, to create incision 45 and thereby bed 43 (not indicated in this view). The configuration of the immediate figure may represent steps 108, 110, 112, and 114 of FIG. 7.

Figure 8C:
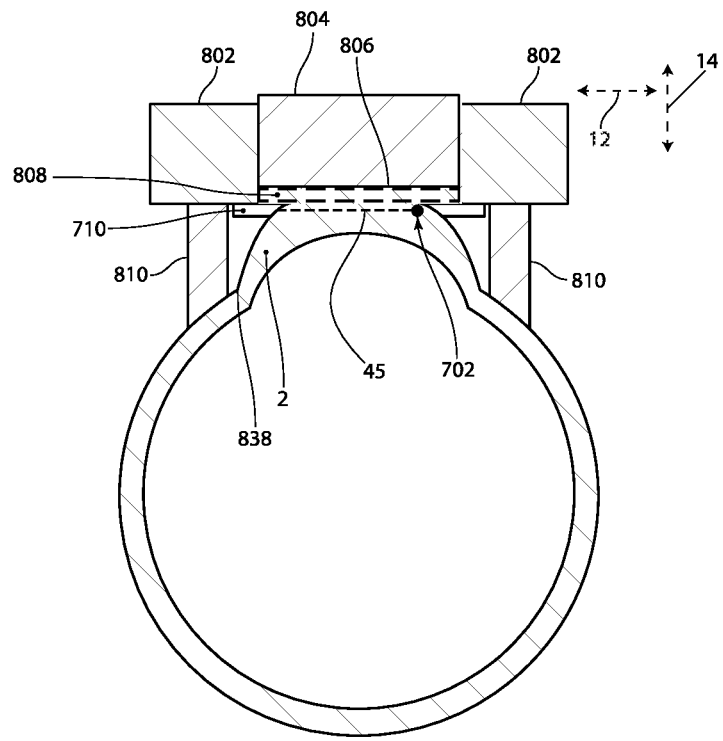

FIG. 8C shows the system of FIG. 8B in a different orientation, as evidenced by axes of motion 12 & 14, such that incision 45 is seen to be progressing through tissue 2 as electrode 702 is translated along axes of motion 12 (shown in this view as proceeding from left to right). The actuation of electrode 702 may be in its final position, such as may be the case when creating a flap incision.

Figure 8D:
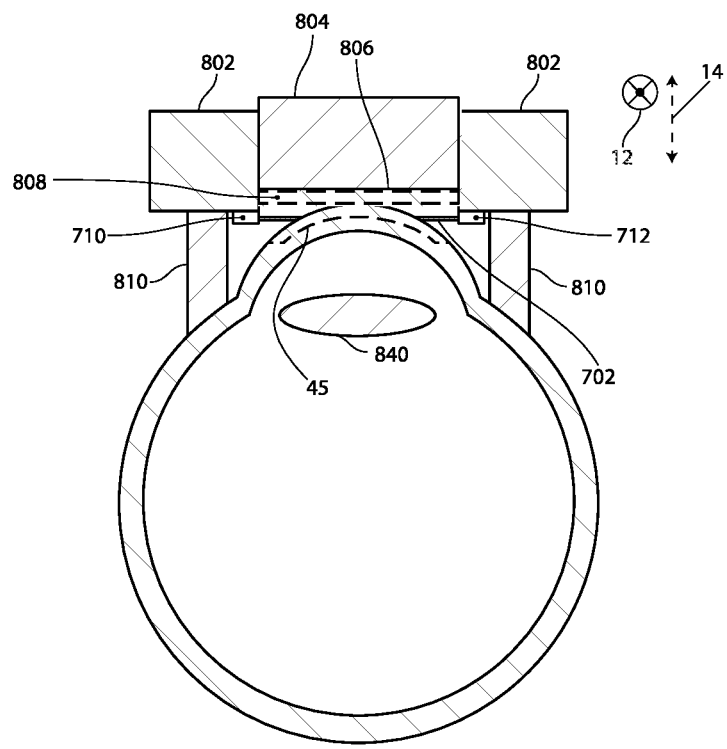

FIG. 8D shows the system of FIGS. 8A-8C, wherein contact plate 804 and therefore contact element 808 may have been moved along axis of motion 14 to just rest atop the apex of corneal surface 842, as in FIG. 8A. The immediate figure now shows incision 45, which may form a surface for bed 43 (not indicated). The surface shape of bed 43 thus created may be nominally characterized as about that of the anterior corneal surface 842. Alternately, the surface shape of the central region of bed 43 (not shown) thus created may characterized as the mean value of at least portions of the surface shapes of the anterior corneal surface 842 and the contact surface 806 (or contact element 808). Said mean may nominally be an arithmetic mean, a geometric mean, a harmonic mean, a weighted mean, or combinations thereof. The configuration of the immediate figure may represent steps 116, 118, 120, and 122 of FIG. 7.

FIG. 9 describes a method of similar to that of FIG. 7, with additional steps 202 through 212; wherein step 116 may be made optional and allow the electrode to incise during step 202. That is, alternately, steps 116 & 118 may be eliminated if there is only low risk of collateral damage due to tissue heating while the actuator changes direction and/or the strain to an unpowered electrode may cause a failure of said electrode due to the change in position of the contact plate. Step 202 involves positioning a contact plate at a second position, which may be a translation of the entire element, or a translation of at least a portion of the element. The translation of at least a portion of the element may be utilized to create a non-planar contact plate surface to provide a desired corneal deformation, as will described with regard to FIGS. 11A and 11B. Alternately, a contact plate may be interchanged at step 202 to provide a desired corneal deformation. Said corneal deformation may be intended to create a surface that defines at least a portion of a lenticule, such as bed 43, to achieve at least a portion of a desired three-dimensional tissue resection profile. Said lenticule may be subsequently removed to cause a refractive change to a cornea 843 of an eye of a patient. Step 204 may be made optional, if step 202 is removed, but may otherwise be similar to step 112. Step 206 involves translating an electrode in a second direction. Said second direction may be nominally the opposite of said first direction. Step 208 involves an electrode disengaging from tissue, such as may occur should the translation of step 206 bring the electrode outside of tissue 2. Step 210 involves disengaging power to an electrode and may be similar to step 116 of FIG. 7. Step 212 involves disengaging the vacuum fixation and freeing the tissue and disengaging the eye being treated and may be similar to step 118 of FIG. 7. Step 122 involves deactivating the system and disengaging it from the eye similar to step 122 of FIG. 7.

Although FIG. 9 shows a method of incising tissue in accordance with some embodiments, one of ordinary skill in the art will recognize that many adaptations and variations can be made in accordance with the present disclosure. For example, the steps can be performed in any suitable order, some of the steps repeated, some of the steps omitted, and combinations thereof.

In some embodiments, a processor as described herein is configured with instructions to perform one or more of the steps of the method of FIG. 9.

FIGS. 10A through 10F are directed at a system similar to that of FIGS. 8A through 8D, further configured such that the shape of contact surface 806 may be configured as other than planar and is shown as convex and additionally that a lenticule (e.g., lenticule 820) may be incised within (stromal) tissue 2 of cornea 843. Contact surface 806 may be considered a corrective surface. The difference between a first incision profile and a second incision profile may correspond to a shape of a lenticule of tissue to be removed from the cornea to treat (or "correct") a refractive error of the eye. The difference between a first incision profile and a second incision profile may correspond to a three-dimensional tissue resection profile. The union of a first incision profile and a second incision profile may correspond to a three-dimensional tissue resection profile.

Figure 10A:
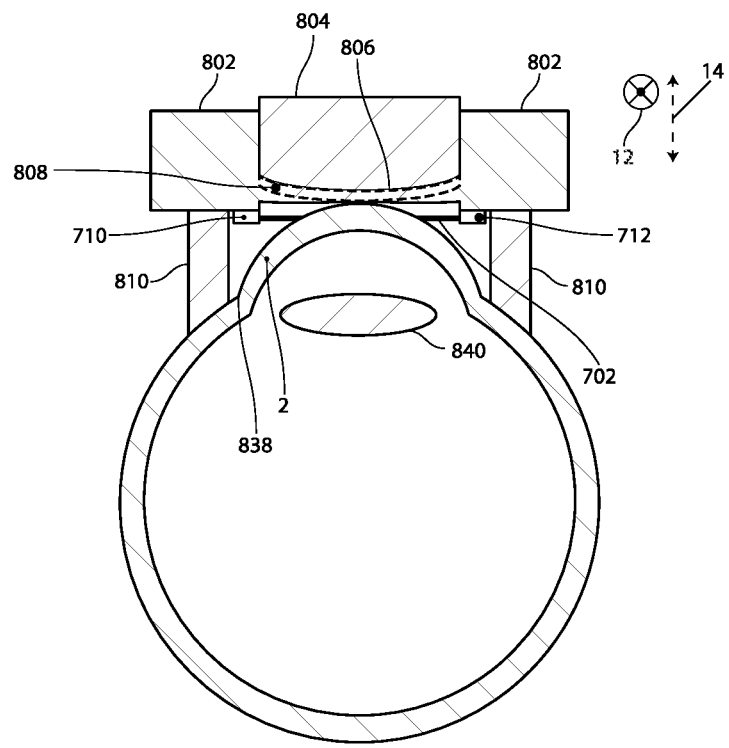
FIGS. 10A through 10F are directed at a system to incise a target tissue structure, in accordance with embodiments of the present disclosure.

FIG. 10A shows a system configured similarly to that of FIG. 8A, with the addition of a curved surface 806 on contact plate 804. Likewise, contact element 806 is placed on curved contact surface 806 and nominally matches said curvature. The configuration of the immediate figure may represent steps 102 through 108 of FIGS. 7 and 9.

Figure 10B:
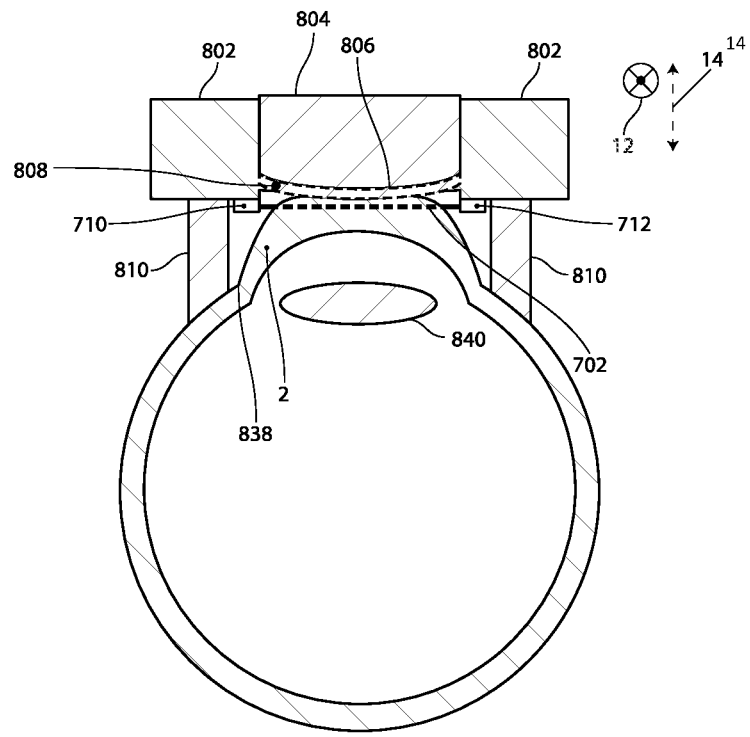

FIG. 10B shows the system of FIG. 10A, wherein contact plate 804 and therefore contact element 808 may have been moved farther along axis of motion 14 to contact cornea 843 and tissue 2 therein. Unlike the configuration of FIGS. 8A through 8C, in the configuration of the immediate figure the cornea is not necessarily applanated but caused to compress to differentially to at least partially match the curvature (or "shape" in the case where a curvature alone cannot suffice to adequately describe contact surface 806) of contact surface 806 in order to produce an incision 46. The configuration of the immediate figure may represent steps 110 through 112 of FIGS. 7 and 9.

Figure 10C:
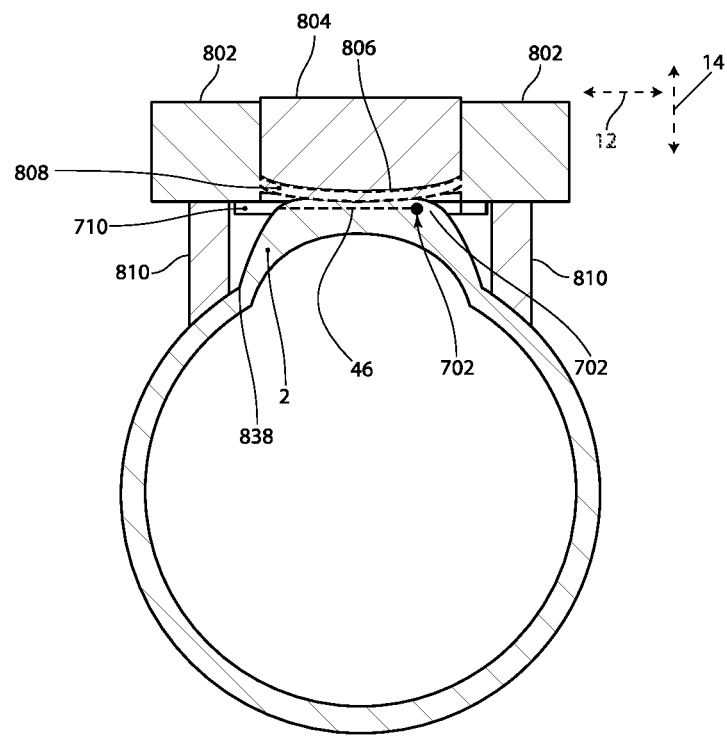

FIG. 10C shows the system of the previous FIGS. 10A-10B in a different orientation, as evidenced by axes of motion 12 and 14, such that incision 46 is seen to be progressing through tissue 2 as electrode 702 is translated along axes of motion 12 (shown in this view as proceeding from left to right). The actuation of electrode 702 may be in its final position, such as may be the case when creating a flap incision.

Figure 10D:
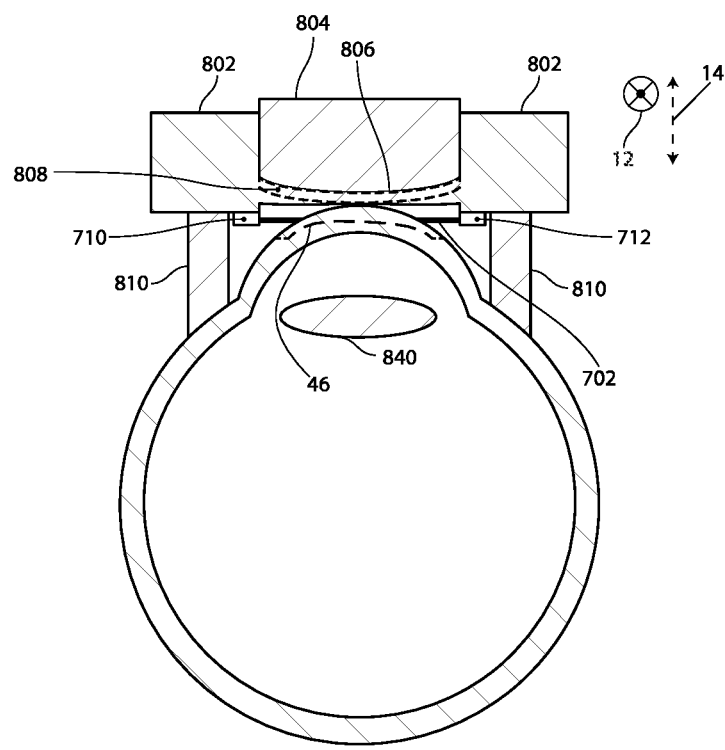

FIG. 10D shows the system of the previous FIGS. 10A-10C, wherein contact plate 804 has been translated anteriorly and incision 46 is now indicated. Such incision 46 may form a surface for bed 44 (not indicated). The surface shape of bed 44 thus created may characterized as the mean value of the surface shapes of the anterior corneal surface 842 and the contact surface 806 (or contact element 808). Said mean may nominally be an arithmetic mean, a geometric mean, a harmonic mean, a weighted mean, or combinations thereof.

Figure 10E:
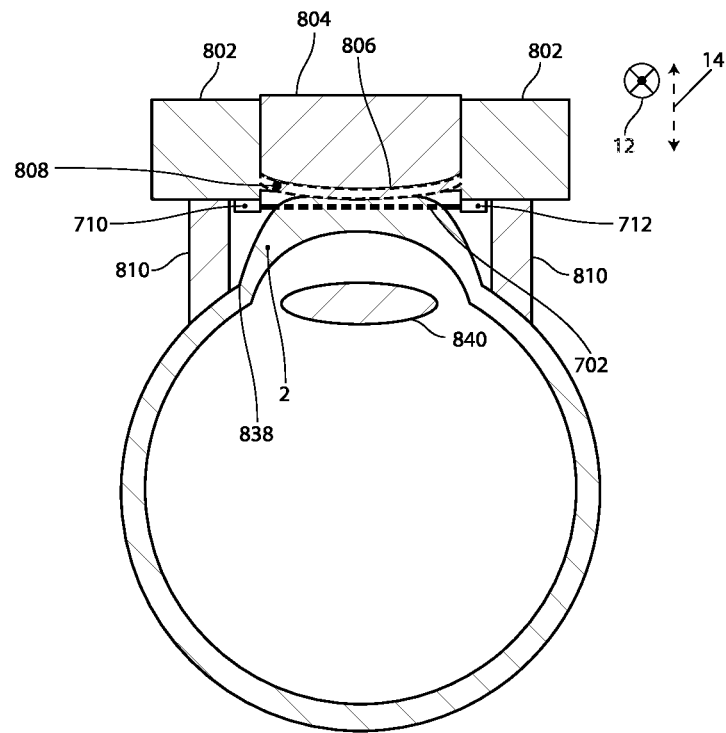

FIG. 10E shows the system of the previous FIGS. 10A-10D, wherein a second incision, incision 45, may now be created. The configuration of the immediate figure may represent steps 202-206 of FIG. 9. Alternately, incision 45 may be created by interchanging contact plate 804, or portions thereof, to provide a different surface shape for incision 45. A flat contact surface may be used for at least one the incisions.

Figure 10F:
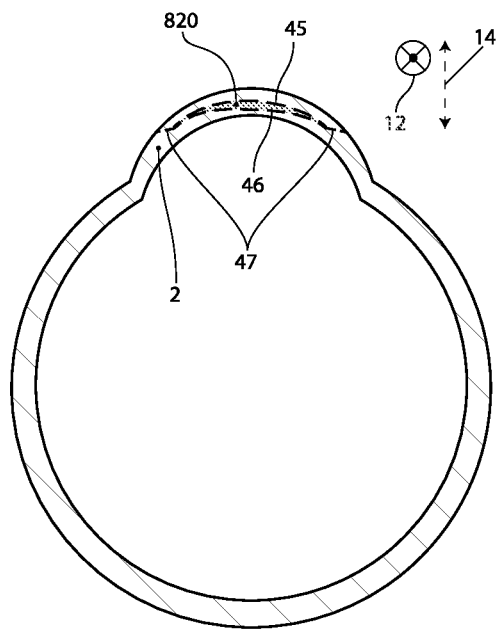

FIG. 10F shows an eye treated with the system of the previous FIGS. 10A-10E, wherein lenticule 820 has been incised within (stromal) tissue 2 of cornea 843 and is bounded by surfaces created by incisions 45, 46. Incisions 45, 46 may comprise incisions 47 when the electrode is made to incise across the entire cornea rather than to create a pocket in the cornea. The configuration of the immediate figure may represent the outcome of completing the remaining steps of FIG. 9. The shapes of surfaces created via incisions 45, 46 may be chosen to affect a refractive correction to a cornea 843 of an eye of a patient. Said refractive correction may be defined, at least in part, by diagnostic measurements such as corneal aberrometry, ocular aberrometry, wavefront aberrometry, corneal topography, and combinations thereof, where the nominal shape of the lenticule may be defined to optically balance (or correct) the measured aberrations, such as has been described in Sekundo W. Small Incision Lenticule Extraction (SMILE) Principles, Techniques, Complication Management, and Future Concepts. 2015. Springer Cham Heidelberg; and the associated citations therein.

In some embodiments, for the cornea an approximate tissue profile for tissue to be removed may be expressed as:

$T(x,y) \sim = W(x,y)/(n-1)$ where T is the thickness in microns, W is the wavefront error in microns, n is the index of refraction of the cornea and x and y are the coordinate references corresponding to a plane, such as a plane near the pupil or vertex of the cornea. The wavefront error can be expressed in many ways, such as with an elevation in microns, or with individual Zernike coefficients for example.

Other approaches may be used to determine the thickness profile of tissue to be removed, for example with reference to the SMILE procedure as will be known to one of ordinary skill in the art.

Figure 11A:
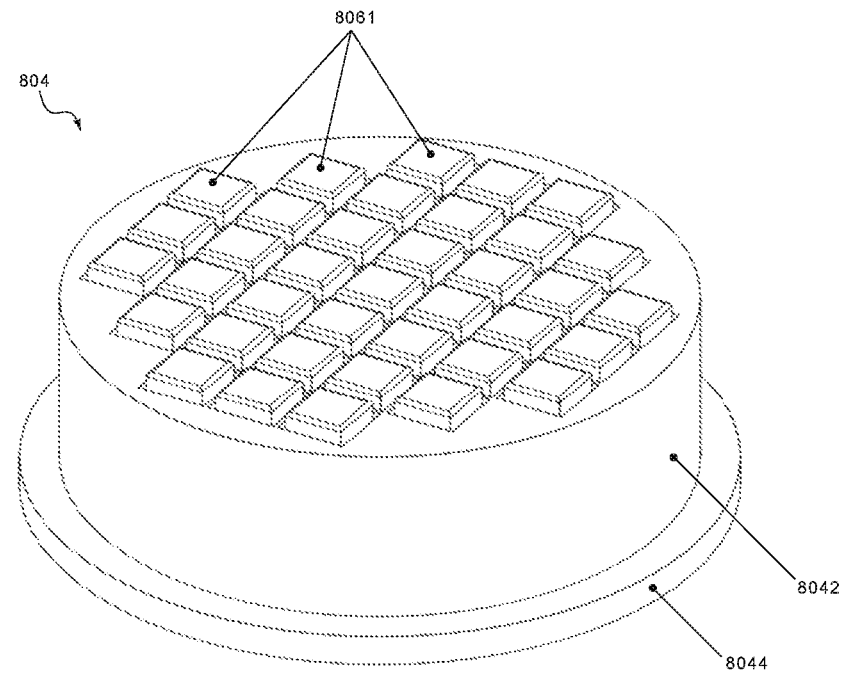
FIGS. 11A and 11B are directed at a piecewise adjustable contact element, in accordance with embodiments of the present disclosure.
Figure 11B:
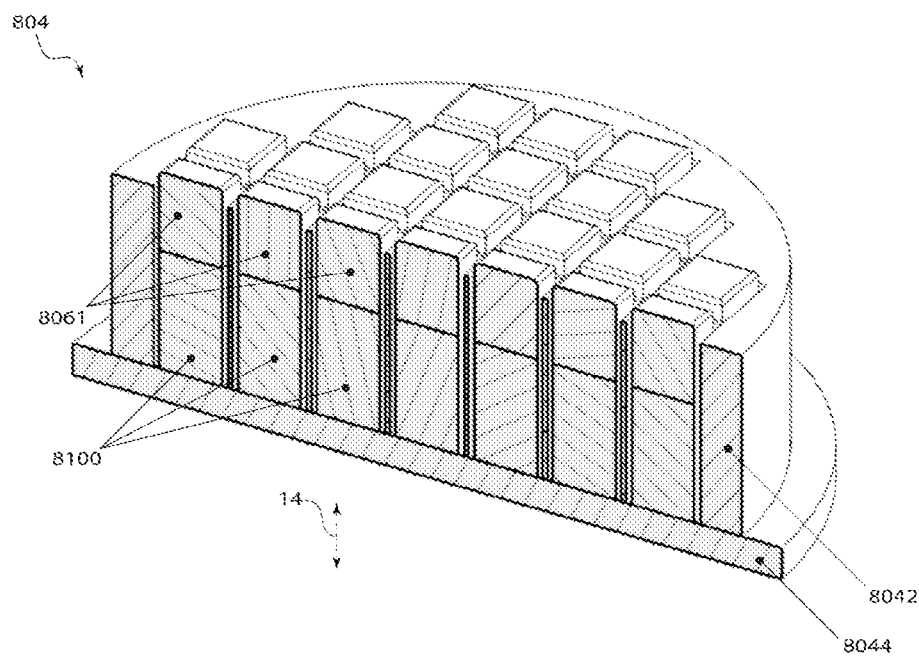

FIGS. 11A and 11B are directed at a piecewise adjustable contact plate 804 to deform the cornea in order to create a lenticule or other therapeutic incision. The adjustable contact plate 804 can be operatively coupled to the controller and configured to shape the cornea to provide refractive correction, for example with reference to small incision lenticular extraction as described herein. FIG. 11A depicts piecewise adjustable contact plate 804 comprised of sub-plates (or, equivalently, "elements") 8061, which together may be constitute a contact surface 806, that may be housed within housing 8042 and mounted to base 8044. FIG. 11B depicts the same contact plate 804 in a cross-sectional view in order to expose actuators 8100 that are operatively coupled to sub-plates 8061 within housing 8042. In the instant embodiment, sub-plates 8061 may each be affixed to an actuator 8100 to allow each subplate 8061 to be individually actuated using additional actuators and associated monitoring and control subsystems, as shown and described in regard to the system of FIG. 6 (said connections not indicated in the immediate figure). By way of non-limiting example, sub-plates 8061 may be adhered to actuators 8100 using an epoxy or be soldered. Actuators 8100 may be selected from the group consisting of: piezoelectric actuators, motors, pneumatic actuators, fluidic actuators, and combinations thereof. As shown in the exemplary embodiment, sub-plates 8061 may be constructed using a material selected from the group consisting of: a glass, a ceramic, a quartz, a silicon, a metal, a polymer, and combinations thereof. Such sub-plates 8061 may be actuated along an axis of motion (e.g., axis of motion 14). Such sub-plates 8061 may be translated (or "displaced") to form a piecewise contact surface 806 with a freeform profile (or "shape" or "surface profile") to create a contact surface 806 with a discrete but arbitrarily addressable profile for use in creating an incision 45 and/or an incision 46 to address optical aberrations, including higher order aberrations, such as defocus, radial distortion, sphere, spherical aberration, cylinder, cylindrical aberration, astigmatism, coma, and trefoil in prescribing a figure for a lenticule to be removed from tissue 2 within a cornea 843. Such sub-plates 8061 may be configured to be nominally rectangular, as shown, but need not be and other geometries are considered within the scope of the present disclosure. A contact element 808 (not shown) may be placed on the distal surface of contact plate 804 to provide a clean and/or sterile surface for contact with tissue 2 and may be configured as a thin, conformal, peel-and-stick sterile barrier, which may also be disposable, as was described elsewhere herein. Rather than utilizing step 202 of FIG. 9 to reposition a contact plate 804, the immediate embodiment may allow for said step 202 to be modified to reconfigure contact plate to a second configuration prior to creating another incision. The number of actuators 8100 may be determined by the spatial resolution requirements of a given prescription and/or the tolerance of the surface figure. By way of non-limiting examples, there may be an array of 10 square cross-sectional shaped actuators 8100, or there may be an array of 14 such actuators 8100, or there may be an array of 28 such actuators 8100; which when configured to be square-packed within the extent of a nominally 12 mm diameter disk-shaped contact surface yield areas of ~2.0 mm$^2$, ~1.44 mm$^2$, and ~0.80 mm$^2$ per actuator 8100, respectively. Alternately, a more regular array may be used, such as a 4×4 square array to yield 16 actuators 8100. When said regular array of 16 square cross-sectional shaped actuators 8100 is positioned concentric with a nominally 12 mm disk-shaped contact surface, the area per actuator may be ~9 mm$^2$, although the corners of the array may lie outside of the 12 mm disk boundary. Similarly, a 10×10 square array may yield an area per actuator of ~1.44 mm$^2$ Alternately, a customized contact plate 804 and/or a corrective portion of contact surface 806 may be fabricated to comprise a surface profile for use in creating an incision 45 and/or an incision 46 to address higher order aberrations in prescribing a figure for a lenticule to be removed from tissue 2 within a cornea 843. Alternately, such customized contact plate 804 and/or contact surface 806 may be used individually in creating an incision 45 and/or an incision 46. Alternately, a first customized contact plate 804 and/or contact surface 806 may be used in creating an incision 45 and a second customized contact plate 804 and/or contact surface 806 may be used in creating an incision 46, wherein the first and second customized contact plates 804 and/or contact surfaces 806 may be configured with different surface profiles. Rather than utilizing step 202 of FIG. 9 to reposition a contact plate 804, the immediate embodiment may allow for said step 202 to be modified to substitute (or "interchange") second contact plate prior to creating another incision. Means of fabricating such customized contact plates 804 and/or contact surfaces 806 may selected from the group consisting of: additive manufacturing, injection molding, machining, and combinations thereof.

In some embodiments, an optical prescription may comprise one or more of surface curvatures, optical power in diopters, material properties, indices of refraction, a wavefront measurement of the eye, or thicknesses. In some embodiments, a surface figure of an optic may be defined as the perturbation of the optical surface from the optical prescription. Low-frequency errors may be typically specified as irregularity, fringes of departure, or flatness and tend to transfer light from the center of the airy disk pattern into the first few diffraction rings. This effect may reduce the magnitude of the point-spread function without widening it, thus reducing the Strehl ratio. Mid-frequency errors (or small-angle scatter) may be specified using slope or (PSD) requirements and tend to widen or smear the point spread function (PSF) and reduce contrast. Low-frequency and mid-frequency errors may both degrade the optical system performance. However, some figure imperfections may be omitted from a surface-figure specification, as may be the case for optical power and occasionally astigmatism. Optical systems may allow for individual optics to be focused, decentered, or tilted to compensate for specific aberrations. Surface accuracy and surface figure are terms often used to capture both regions. To eliminate ambiguity, one may use microns as the unit value in specifications.

Figure 12A:
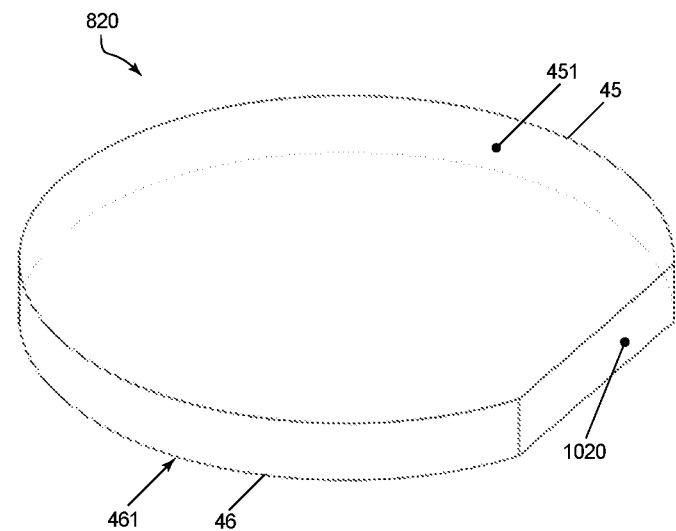
FIGS. 12A and 12B are directed at a disc-shaped lenticule, in accordance with embodiments of the present disclosure.
Figure 12B:
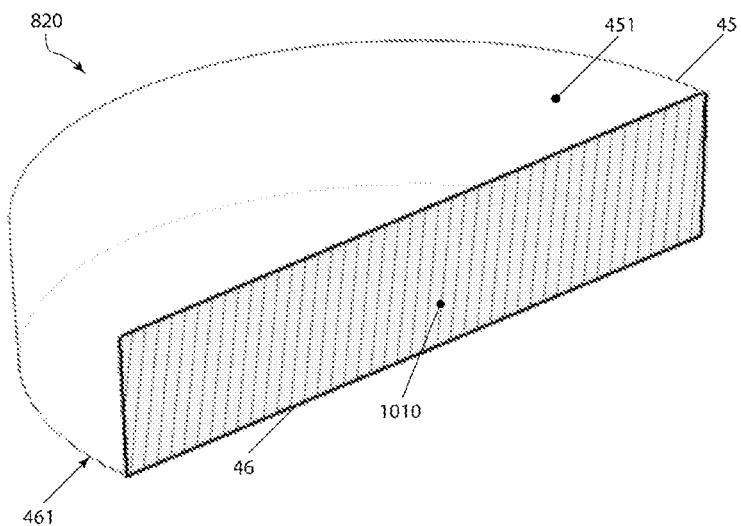

FIGS. 12A and 12B are directed at the creation of a disc-shaped lenticule. FIG. 12A shows lenticule 820, which is comprised of anterior surface 451 that may be created by incision 45 via step 114 of FIGS. 7 and 9, and posterior surface 461 that may be created by incision 46 via step 116 or 118 of FIGS. 7 and 9. Hinge 1020 may be created via step 202 of FIG. 9, the translation of contact plate to a second position between the creation of incisions 46 and 45. In the present figure the lenticule may appear to be a flat disc as shown when it is spread upon a flat surface, as shown. FIG. 12B shows a cross-sectional view of the same lenticule 820 of FIG. 12A. It the instant embodiment, a nominally planar contact plate may be positioned to first position (or "depth" or "location") to create incision 46 and then translated to a second, more anterior (or "proximal"), position in order to create incision 45. In the configuration of the instant embodiment, cross-sectional shape 1010 may be nominally rectangular and faces 451 & 461 may be nominally parallel. Alternately, incision 45 more be created at a more posterior (or "distal") position than that of incision 46 by appropriate translation of the contact plate.

Figure 13:
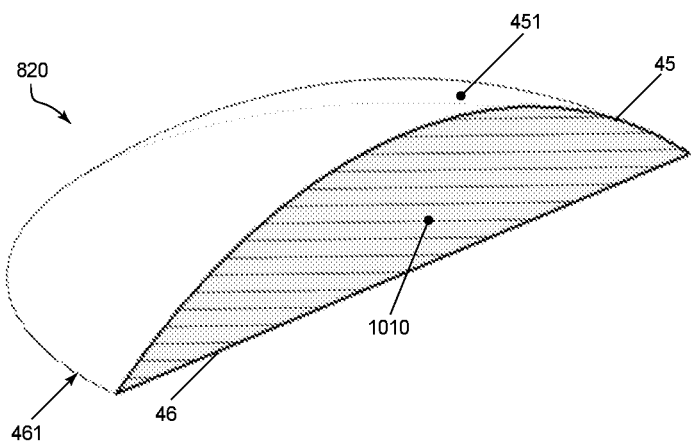
FIGS. 13 through 15 are directed at different lenticule configurations, in accordance with embodiments of the present disclosure.

FIG. 13 is directed at a plano-convex type lenticule, similar to that of FIG. 12B, in accordance with embodiments of the present disclosure. Here lenticule 820 comprises anterior face 451 that may be created by incision 45 and posterior face 461 that may be created by incision 46. The contact plate, or elements of a contact plate comprised of a plurality of translatable elements, may be configured to produce a non-planar type of surface for face 451. The configuration of the instant embodiment may be utilized to create a plano-convex type lenticule, as shown.

Figure 14:
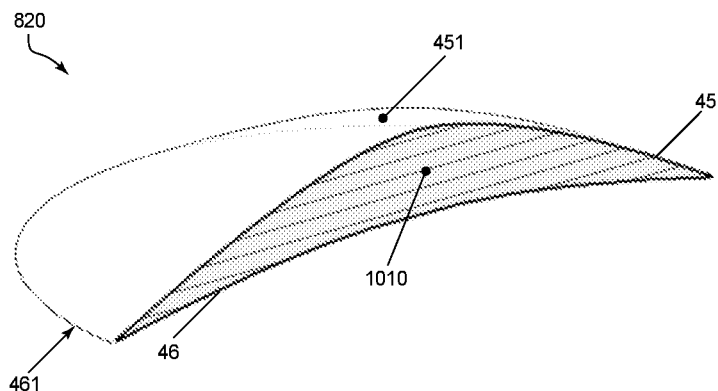

FIG. 14 is directed at a meniscus-shaped lenticule, similar to that of FIG. 13, in accordance with embodiments of the present disclosure. Here lenticule 820 comprises anterior face 451 that may be created by incision 45 and posterior face 461 that may be created by incision 46. The contact plate, or elements of a contact plate comprised of a plurality of translatable elements, may be configured to produce a non-planar type of surface for both faces 451 & 461. The configuration of the instant embodiment may be utilized to create a meniscus type lenticule, as shown.

Figure 15:
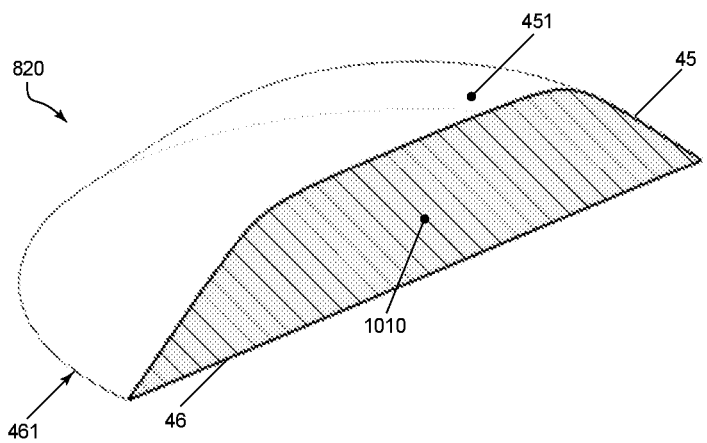

FIG. 15 is directed at a hybrid type lenticule, similar to that of FIG. 14, in accordance with embodiments of the present disclosure. Here lenticule 820 comprises anterior face 451 that may be created by incision 45 and posterior face 461 that may be created by incision 46. The contact plate, or elements of a contact plate comprised of a plurality of translatable elements, may be configured to produce a non-planar type of surface for both faces 451 & 461. The configuration of the instant embodiment may be utilized to create a hybrid type lenticule, as shown.

Figure 16A:
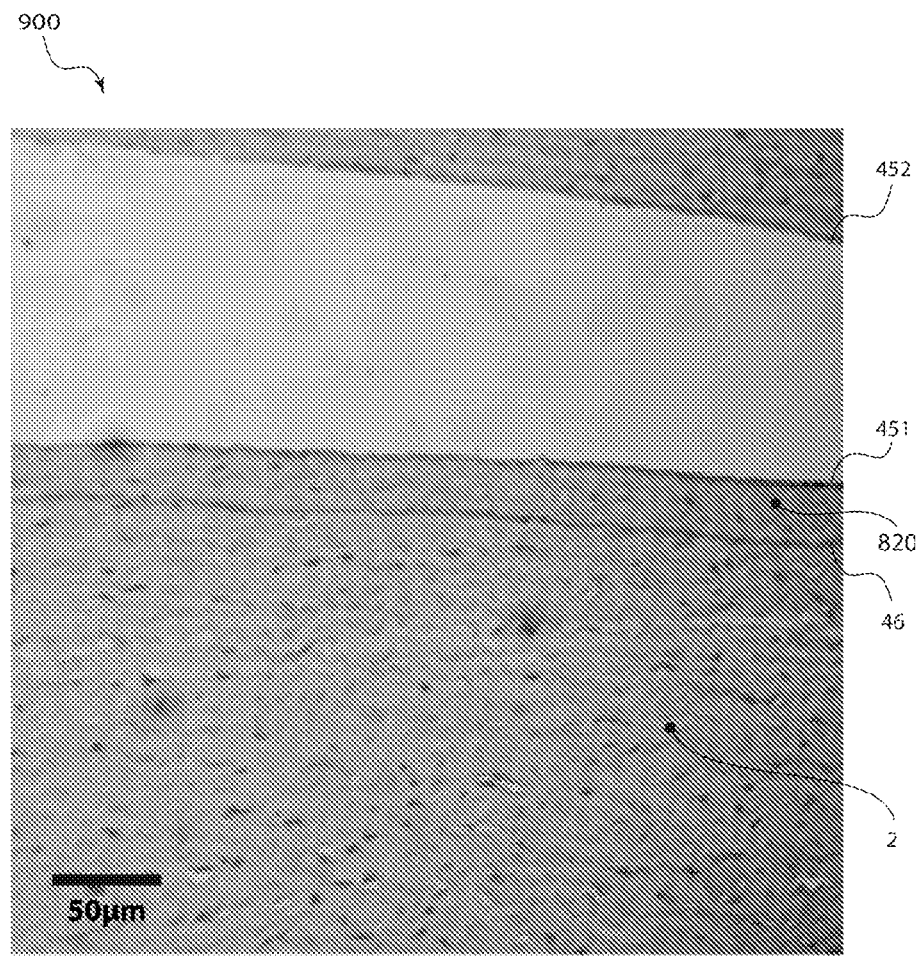
FIGS. 16A and 16B are directed at histological images of porcine corneas containing incisions made, in accordance with embodiments of the present disclosure.
Figure 16B:
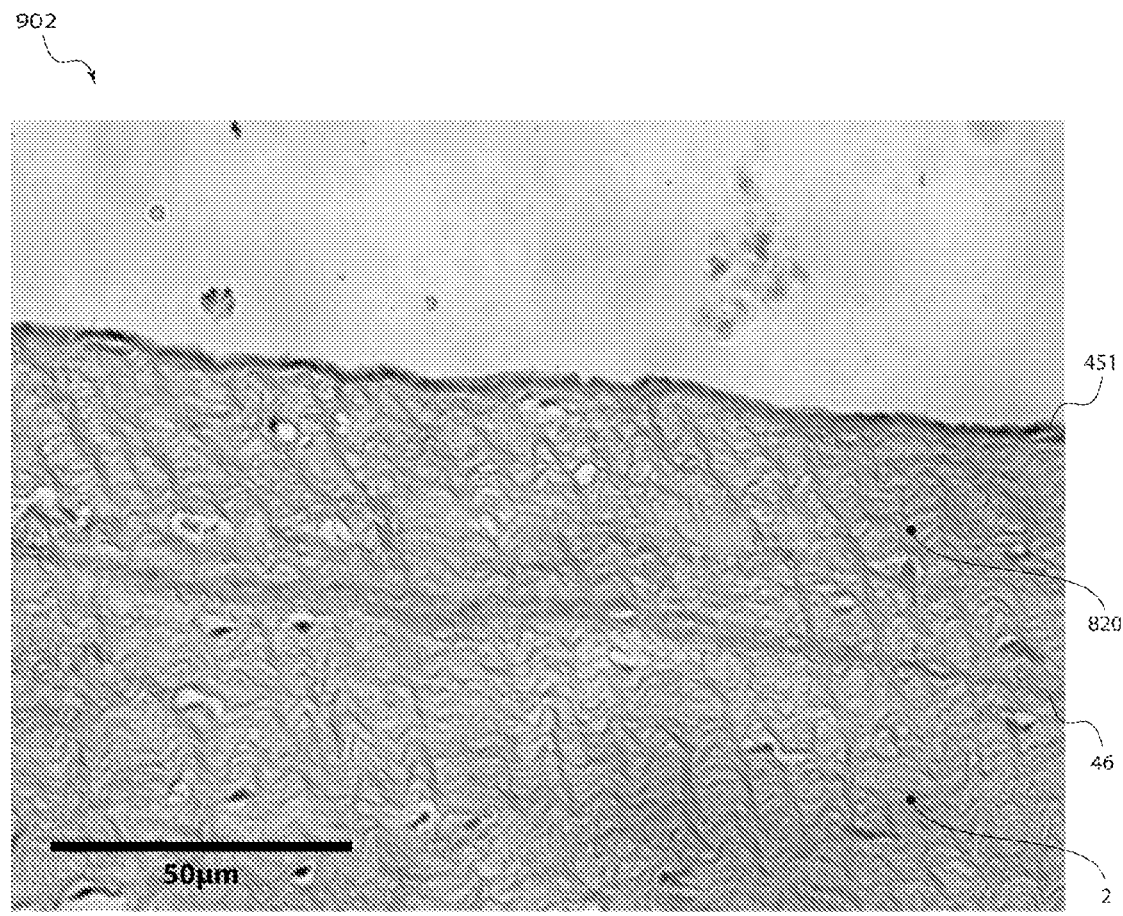

FIGS. 16A and 16B are directed at histological images of incisions in porcine cornea created in accordance with embodiments of the present disclosure. FIG. 16A shows image 900, a traditional sagittal cross-sectional (H&E stained) histological microscopic image of a porcine cornea that was incised when fresh (≤2 days post-harvest, stored at ~2° C.) and was subsequently fixed in a 4% paraformaldehyde solution. The incisional system was configured as follows: PRF~1 MHz, V~+250V, sinusoidal waveform, $P_{rms}$~15 W; $V_{t,max}$~400 mm·s$^{-1}$; constant acceleration ~2000 mm·s$^{-2}$; ~Ø15 μm, L~10 mm, ~99.99% pure tungsten wire electrode; T~290 mN; ~35 μm contact plate (flat) posterior displacement between incisions 45 & 46, and a vacuum gauge pressure of ~−500 mmHg for suction element 810 as measured at vacuum sensor 854. Electrode assembly translation was accomplished using M-664.164 piezo-motor actuators from (PI, Karlsruhe, Germany). Target tissue 2 is corneal stromal tissue. Incision 45 was separated to reveal surfaces 451 and 452. Incision 46 was left intact with lenticule 820 in place. Damage may be visible as the darker bands along incisions 45 & 46 and may be on the order of ~3 μm in extent. FIG. 16B shows image 902, similar to that of FIG. 16A, but at a higher magnification and with the different spacing between incisions 45 & 46 by means of a ~50 μm posterior contact plate translation. Again, narrow damage zones are evident.

Figure 17:
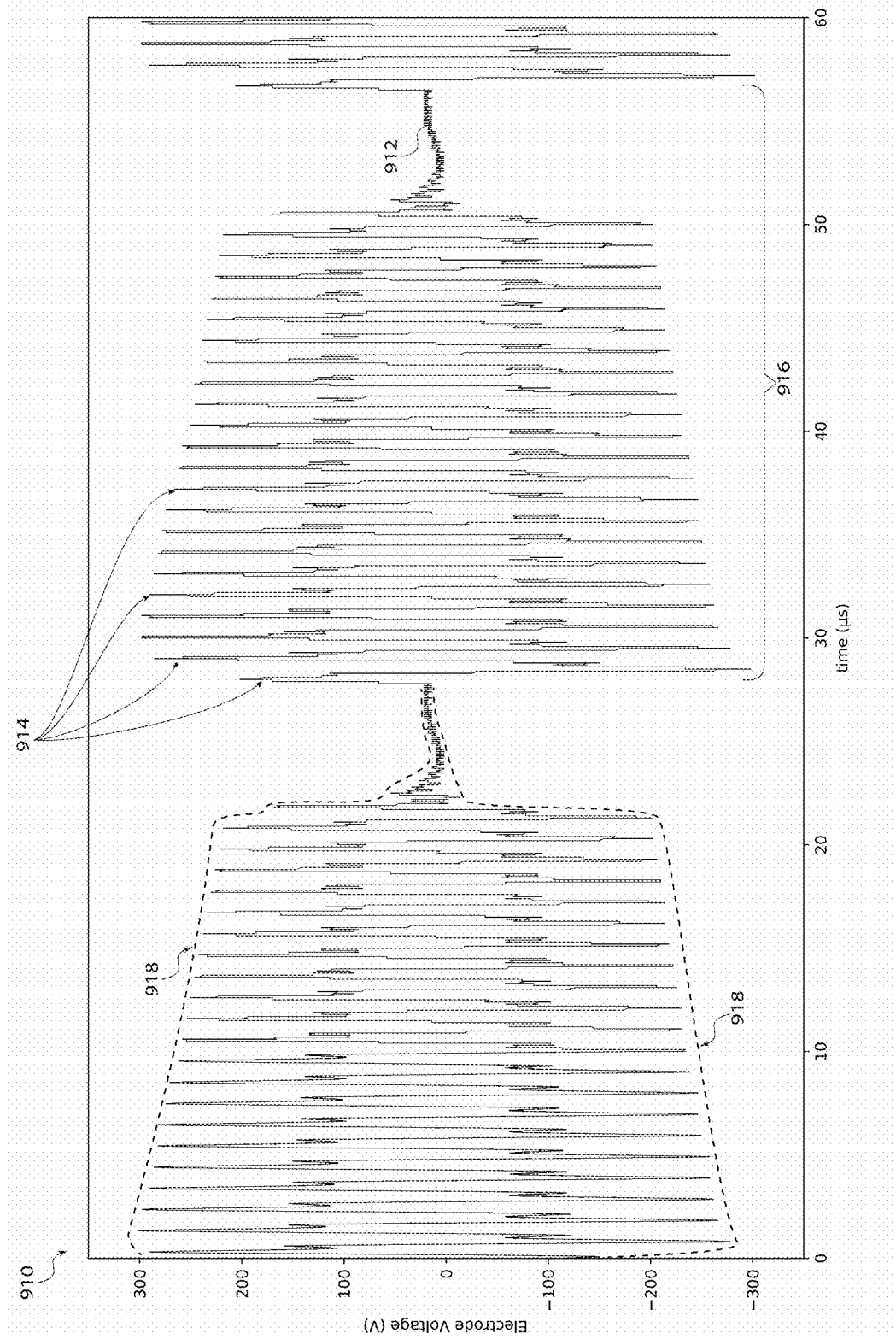
FIG. 17 is directed at a plot displaying an exemplary electrode voltage versus time, in accordance with embodiments of the present disclosure.

FIG. 17 is directed at plot 910, which displays an exemplary electrode voltage versus time waveform 912 that comprises features in accordance with embodiments of the present disclosure. Waveform 912 comprises individual cycles 914. Bursts 916 are comprised of pulses (cycles 914) and constrained by modulation envelope 918. Modulation envelope 918 may be configured to be a combination of the relationships described elsewhere herein, including pulsatile, duty cycle, and modulation (e.g., ramping) relationships. While shown here for clarity at the level of pulses and bursts, an entire incisional waveform may be similarly configured.

Figure 18:
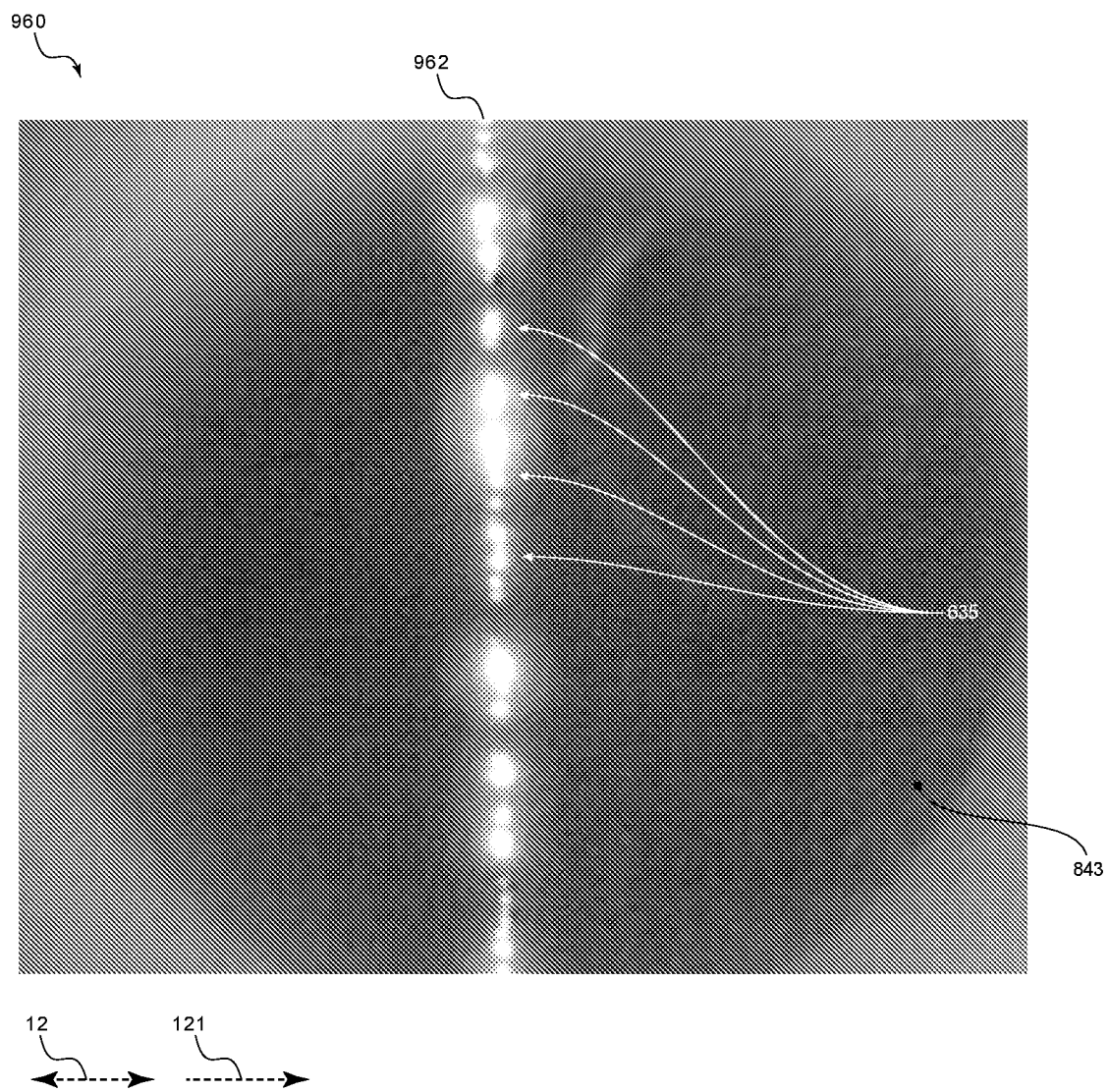
FIG. 18 is directed at a high-speed video image of a porcine cornea being incised, in accordance with embodiments of the present disclosure.

FIG. 18 is directed at image 960, a 576 pixel×464 pixel frame, as may be obtained using a high-speed digital camera such as the AOS M-VIT 4000 (AOS Technologies, Daettwil, Switzerland), when configured to operate with an equivalent sensitivity of 6400 ISO, and a shutter speed (or "integration time") of $t_{sh}$ ~250 μs. In the instant figure, the plurality of vapor cavities 635 along image element 962 may show the staccato disruption process, which may correspond to an electrode translation of about one diameter, as $v_i*t_{sh}$→~13 μm and PRF*$t_{sh}$→~250 cycles of a ~1 MHz waveform for an incisional system configured similarly to that of FIGS. 6 through 10E: $V_{t,max}$~400 mm s$^{-1}$; constant acceleration ~2000 mm s$^{-2}$; ~Ø13 μm, L~10 mm, ~≥99.99% pure tungsten wire electrode; T~280 mN; and a vacuum gauge pressure of ~−640 mmHg for suction element 810 as measured using a vacuum sensor 854, and nominally utilizing the waveform of FIG. 17. A plurality of vapor cavities 635 may be visible along image element 962 as an electrode 702 (located at image element 962, but otherwise obscured in the present figure) is actuated to translate along axis of motion 12 in direction 121 to create an incision within cornea 843. The plurality of vapor cavities 635 may comprise regions where light is emitted in association with the formation of plasma, and the light may comprise a wavelength that is a function of the plasma temperature and may lie within a range from about 400 nm to about 750 nm.

In accordance with embodiments of the present disclosure the technique dependency of scleral incisions may be reduced by semi-automating flap creation using a plasma-induced cutting tool which limits tissue damage and providing predictable, accurate, and precise incisions in the sclera and/or cornea, including the sclero-corneal limbus. In accordance with embodiments of the present disclosure, pockets in the sclera and/or cornea, including the sclero-corneal limbus may be made rather than the flaps traditionally used. Further embodiments may provide for incising other tissues, such as those listed in FIG. 1A. By way of non-limiting example, a plasma-induced incision may be created in a CAPSULE to produce a capsulorrhexis; in a LENS to produce lens fragments or to simplify lens fragmentation and/or lens removal; in a RETINA to produce a pocket or flap, in a TM to improve drainage and/or to lower IOP; and in an IRIS to produce an iridotomy.

A flap may be described as an incision yielding a "flap" of tissue that may be lifted and pivot on a "hinge" to provide access to the tissue beneath it. By way of nonlimiting example, cutting three sides of a square to the 50% depth and razing a plane at that 50% depth beneath the edges of the square of a tissue may yield a half-thickness flap with the fourth uncut side of the square as its hinge. A flap may be amputated by completing the fourth side of the exemplary square incision.

A pocket may be described as an incision that separates a first depth (or layer) of tissue from a second depth (or layer) of tissue without necessarily creating a flap. By way of a further nonlimiting example, cutting one side of a square to the 50% depth and razing a plane at that 50% depth beneath the edges of the square of a tissue may yield a half-thickness pocket.

A semi-automated cutting tool may be used to yield an incision improved over those of traditional sharp-edged instruments. A plasma-induced, semi-automated cutting tool may be used to yield an incision improved over those of a semi-automated cutting tool configured for use with traditional sharp-edged instruments.

A semi-automated cutting system with at least one degree of motion may be used to create the 5×5 mm and 4×4 mm flaps instead of manually creating them. For example, a system comprising both 5 mm wide and 4 mm wide "blades" may be used to create the 5×5 mm and 4×4 mm flaps, respectively. An electrode may comprise a wire and/or a blade.

FIG. 19A shows flap 40 in tissue 2 as seen from above, and FIG. 19B shows the same flap 40 as seen looking into cross-section A-A. Flap 40 is constructed of incisions 42 and 44, which create bed 43 and form 3 sides of a square (in the examples of FIGS. 19A-19D, although other such shapes are also considered within the scope of the present disclosure). The flap may be lifted and hinge about the missing side of the square to expose the tissue beneath. Bed 43 may be planar or curved. A flap may be amputated by completing the fourth side of the exemplary square incision.

Similar to the configuration of FIGS. 19A and 19B, FIG. 19C shows pocket 41 in tissue 2 as seen from above, and FIG. 19D shows the same pocket 41 as seen looking into cross-section A-A. However, in this configuration, pocket 41 is comprised of incision 42, which creates bed 43, but lacks incisions 44. Again, bed 43 may be planar or curved, but this time will be dependent upon the longitudinal shape (or "profile") of the incisor in order to avoid creating incisions 44.

Figure 20:
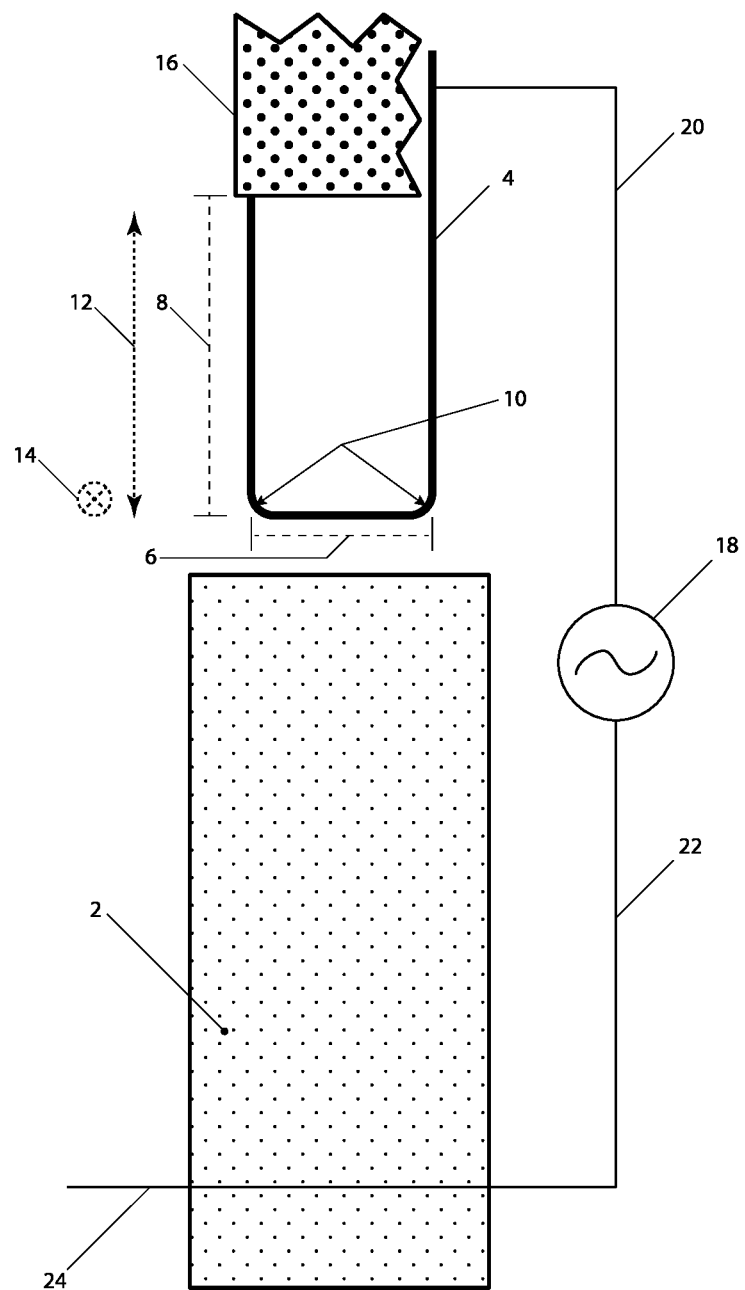
FIG. 20 depicts aspects of a system that is configured to create a tissue flap or a tissue pocket, in accordance with embodiments of the present disclosure.

FIG. 20 is directed at a system in accordance with embodiments of the present disclosure configured to create a rectangular flap or pocket as may be useful in canaloplasty for the reduction of IOP in the treatment of glaucoma. Tissue 2 may be incised using electrode 4, which is configured in a U-shape of width 6 and length 8 and comprises bends 10 in this exemplary embodiment. Electrode 4 may be connected to power RF driver 18 via lead 20. Lead 22 may be connected to the patient creating electrode 24, which in turn may be a part of a return path. RF driver may produce bipolar pulses. Electrode 4 may be enclosed within a sheath 16, shown here as partially cut-away for clarity. Direction of motion 12 may be used to provide a lateral extent to the incision and direction of motion 14 may be orthogonal to direction of motion 12 and perpendicular to the plane described by the width 6 of U-shape of electrode 4, such as may be used to create a tissue flap and/or pocket. Alternately, direction of motion 14 may be employed to create an incision nominally perpendicular to a surface of tissue 2. Width 6 may be chosen to be between 1 mm and 10 mm, specifically 4 mm or 5 mm, as described above. Length 8 may be greater than width 6 and made to traverse tissue a distance less than length 8. For example, a 4 mm×4 mm flap may be created by configuring width 6 to be 4 mm and length 8 to be greater than 4 mm but made to traverse 4 mm of tissue along direction of motion 12.

Figure 21:
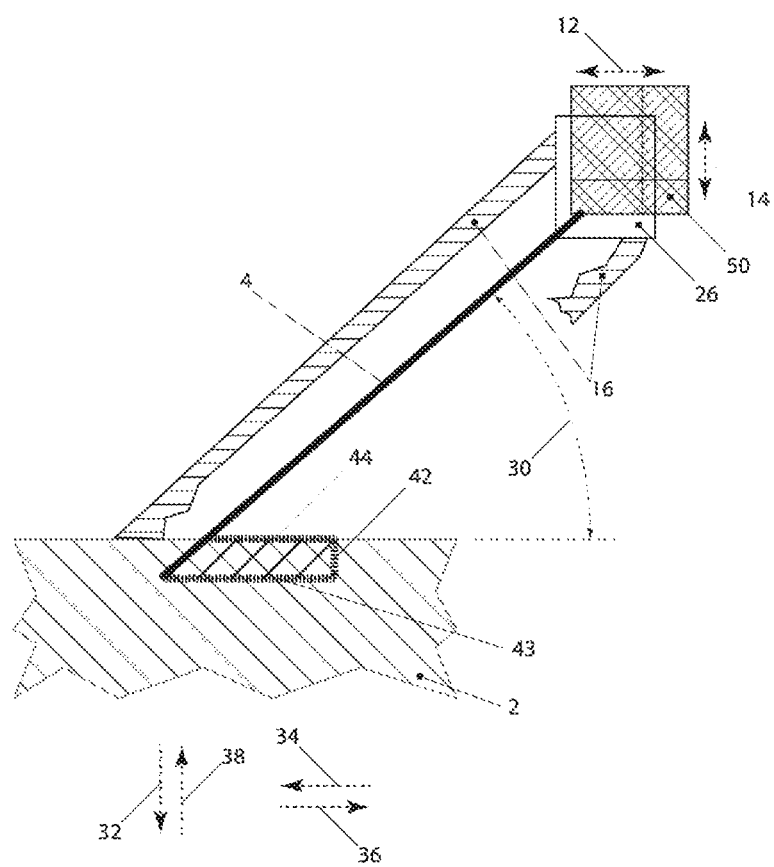
FIG. 21 depicts aspects of a system, in accordance with embodiments of the present disclosure.

FIG. 21 is directed at a system similar to that of FIG. 20, as seen from the side and configured to create a flap; with the additions of probe body 26 to contain electrode 4, sheath 16, and actuator 50; as well being oriented at angle 30 relative the surface of tissue 2. Actuator 50 may be operatively coupled to electrode 4 and move in directions of motion 12&14 such that electrode 4 is made to translate within tissue 2 along a motion profile described by moving first in direction 32; then direction 34; then direction 36, which is in opposite direction from direction 34; then direction 38, which is in opposite direction from direction 32. This configuration may then create a flap 40 (not explicitly shown for purposes of clarity) by creating incision 42, then incision 44 and bed 43. Actuator 50 may be powered, such as a motor or voice coil, by way of non-limiting examples. Alternately, actuator 50 may comprise a series of springs and ratchets or stop and triggers to create the motion profile described. Elements electrode 4 and/or sheath 16 and/or probe body 26 may be configured to be a subsystem that engages with actuator 50 and RF driver 18 and to be disposed of after use.

In an alternate embodiment, a flap may be amputated by altering the motion profile as follows: by moving first in direction 32; then direction 34; then direction 38, which is in opposite direction from direction 32.

Alternately, the system of FIG. 21 may be configured such that actuator 50 translates electrode 4 first in a direction that is nominally along angle 30 then retract electrode 4 along a second direction that is nominally the opposite of the first direction in order to create a pocket rather than a flap.

Alternately, a second electrode may also be used to create a second flap or pocket that of different size and/or shape than a first flap or pocket. For example, a 5 mm×5 mm flap may be first made first and subsequently and 4 mm×4 mm flap may then be made. The exemplary 4 mm×4 mm flap may further be an amputated flap.

Figure 22A:
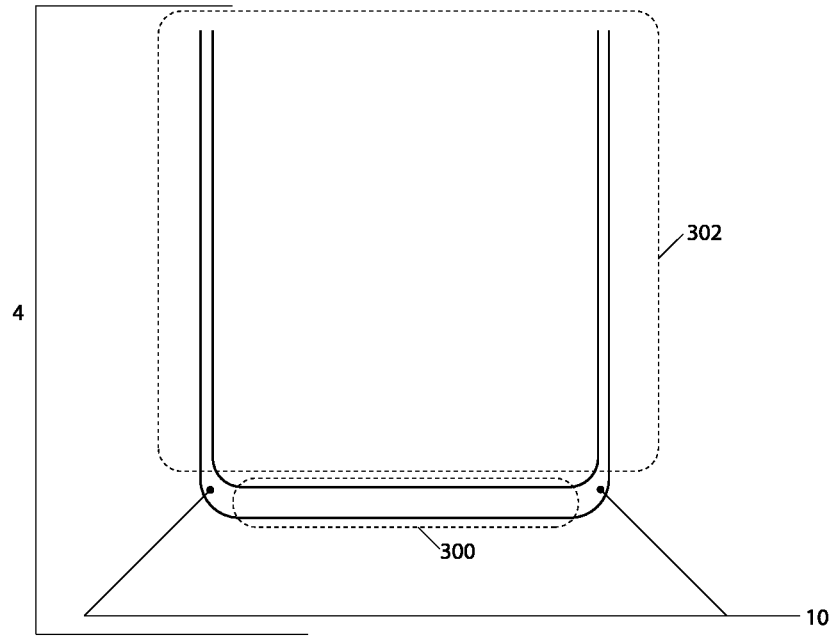
FIGS. 22A through 22C depict aspects of a system, in accordance with embodiments of the present disclosure.
Figure 22B:
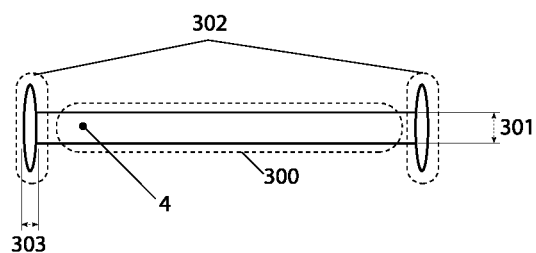
Figure 22C:
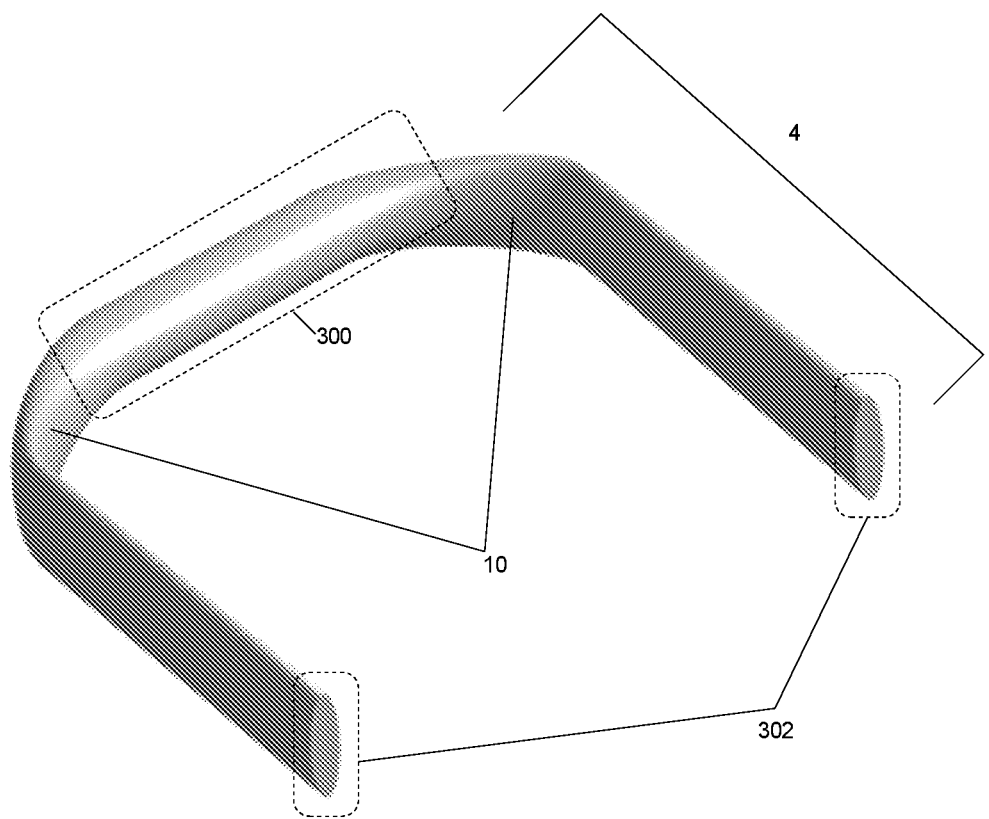

FIGS. 22A-22C are directed at details of an electrode configured in accordance with embodiments of the present disclosure, wherein electrode 4 comprises regions 300, 302, and bends 10. Nominally, the surface area may be kept constant along electrode 4. By way of non-limiting example, electrode 4 may comprise a solid wire of diameter between ~50 μm and ~300 μm and be composed of a material selected from the group consisting of; tungsten, nitinol, steel, copper, stainless steel, beryllium-copper alloy, cupronickel alloy, and aluminum. Furthermore, in alternate embodiments, an electrode may be at least partially coated with another conducting material, such as gold. Region 302 may comprise the same base structure as region 300 with the modification of being compressed in the direction parallel to the plane of the image and elongated in an orthogonal direction. Such a configuration may maintain the surface area while providing increased strength in the aforementioned orthogonal direction for improved reliability and strength while incising tissue by reducing dimension 303 to be less than dimension 301. Bends 10 may be made from either the configuration of region 300, that of region 302, or be made to transition between regions 300 & 302. Alternately, regions 300 and 302 and/or bends 10 may be joined from disparate materials. In a further alternate embodiment, electrode 4 may be constructed from tungsten wire with a diameter of ~250 μm, which has been compressed everywhere except region 300 of length ~3 mm and with a dimension 301 that is nominally the same as the ~250 μm native diameter of the wire, and to the native bends 10 located about the region 300 and made to have radii of ~0.5 mm to yield a width 6 of ~4 mm while dimension 303 is configured to be formed by the aforementioned compression and to ~400 μm.

For purposes of clarity, electrode 4 has been shown thus far as being U-shaped but it need not be. Rf driver 18 may provide an alternating current to electrode 4. Such an alternating current may be, by way of non-limiting examples; a sinewave, a square wave, a sawtooth wave, a triangle wave, or a combination thereof. The signal provided by rf driver 18 may be configured to have a base (or "carrier") frequency between ~10 kHz and ~10 MHz and it may be further modulated to comprise bursts of pulses at frequency of between ~100 Hz and ~3 MHz to create a duty cycle. The duty cycle may be between ~0.01% and ~100%. In alternate embodiments, the duty cycle may be between ~60% and ~80%. The peak-to-peak voltage provided by rf driver 18 may be between ~500V and ~2000V. In alternate embodiments, the peak-to-peak voltage provided by rf driver 18 may be between ~400V and ~800V. In one embodiment the signal of rf driver 18 may be configured to have a peak-to-peak bipolar voltage of ~800V (comprising both ~+400V and ~−400V amplitudes) with a carrier frequency of ~1 MHz and a modulation frequency of ~10 kHz, such as may be useful when electrode 4 is comprised of a ~Ø100 μm diameter tungsten wire in region 300.

Figure 23:
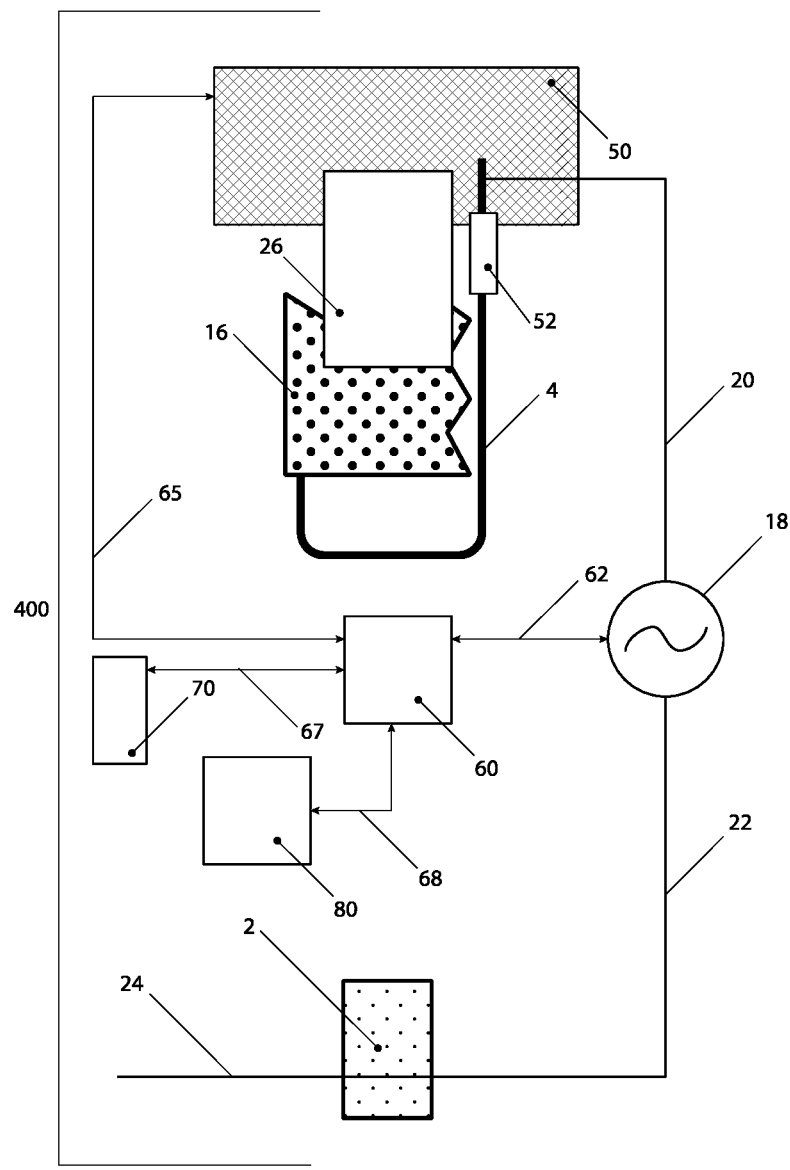
FIG. 23 depicts aspects of a system, in accordance with embodiments of the present disclosure.

FIG. 23 is directed at system 400, which is configured in accordance with embodiments of the present disclosure. In addition to the elements related to previous figures, system 400 further comprises controller 60, power supply 70, user interface 80, and coupler 52. Connection 62 connects controller 60 with RF driver 18 and is at least a unidirectional connection. Connection 62 may also be a bidirectional connection wherein controller 60 is able to sense and/or respond to at least a signal from rf driver 18. Such a signal may be a safety signal related to a sensed voltage or current. In a further alternate embodiment, rf driver 18 may provide feedback to controller 60 or use such feedback internally and may share such feedback as signals with controller 60. Such feedback may be, for example, EMF or current feedback and may be useful in determining when electrode 4 contacts tissue and/or the status of the plasma. Such status may be, for example, whether or not the plasma in the glow discharge regime or not. Likewise, connection 65 connects controller 60 with actuator 50 and is at least a unidirectional connection. Actuator 50 may be comprised of at least one electrical motor and may further comprise a positional encoder. Connection 65 may alternately be a bidirectional connection wherein signals are shared between controller 60 and actuator 50, such as position, velocity, acceleration, out of bounds errors, etc. In a further alternate embodiment, actuator 50 may provide feedback to controller 60 or use such feedback internally and may share such feedback as signals with controller 60. Such feedback may be, for example, force feedback and may be useful in determining when electrode 4 contacts tissue or when it imparts excessive force on the tissue to be incised. Likewise, connection 67 connects controller 60 with power supply 70 and is at least a unidirectional connection. In a further alternate embodiment, power supply 70 may provide feedback to controller 60 or use such feedback internally and may share such feedback as signals with controller 60. Such feedback may be, for example, an error signal. Such error signals may be temperature errors, input voltage errors, output voltage errors, input current errors, output current errors, etc. Likewise, connection 68 connects controller 60 with user interface 80 and is at least a unidirectional connection. In a further alternate embodiment, interface 80 may provide feedback to controller 60 or use such feedback internally and may share such feedback as signals with controller 60. For example, user interface 80 may be a graphical user interface or a button used to signal actuator 50 to move electrode 4 and incise tissue. This exemplary embodiment of system 400 also includes coupler 52, which may couple electrode 4 to actuator 50 such that electrode 4 may be moved, as described with respect to earlier figures. Coupler 52 may be constructed from an electrically insulating material and be configured to electrically isolate electrode 4 from at least one other element of system 400. Coupler 52, and/or sheath 16, as well as electrode 4 may be joined into a subsystem that may be disposed of after use. An alternate embodiment is a configuration for coupler 52 that may be made to connect both sides of the (exemplary) U-shaped electrode 4 to actuator 50. Electrode 4 may be translated by actuator 50 at a rate of ~200 mm·s$^{-1}$.

Figure 24A:
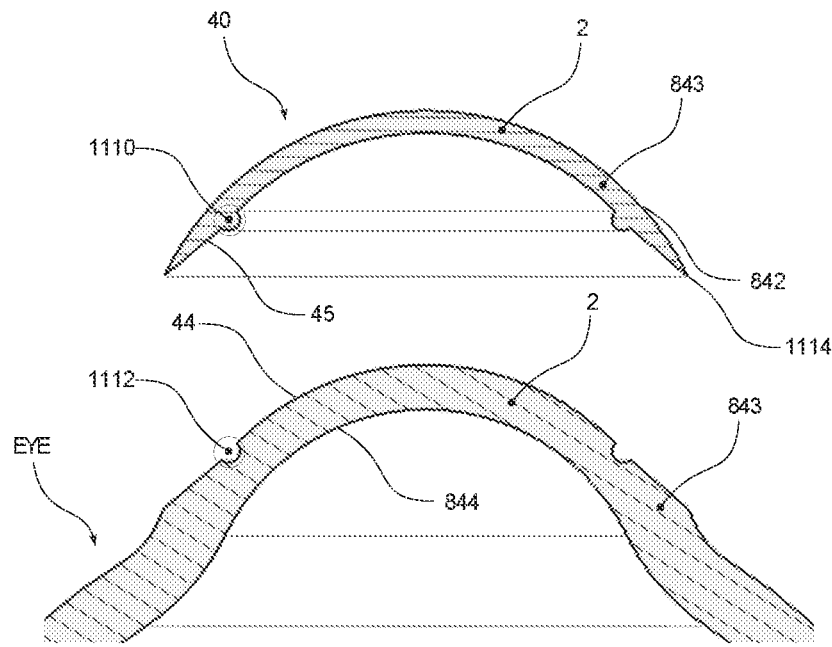
FIGS. 24A and 24B depict aspects of a corneal incision comprising complementary features in accordance with embodiments of the present disclosure.
Figure 24B:
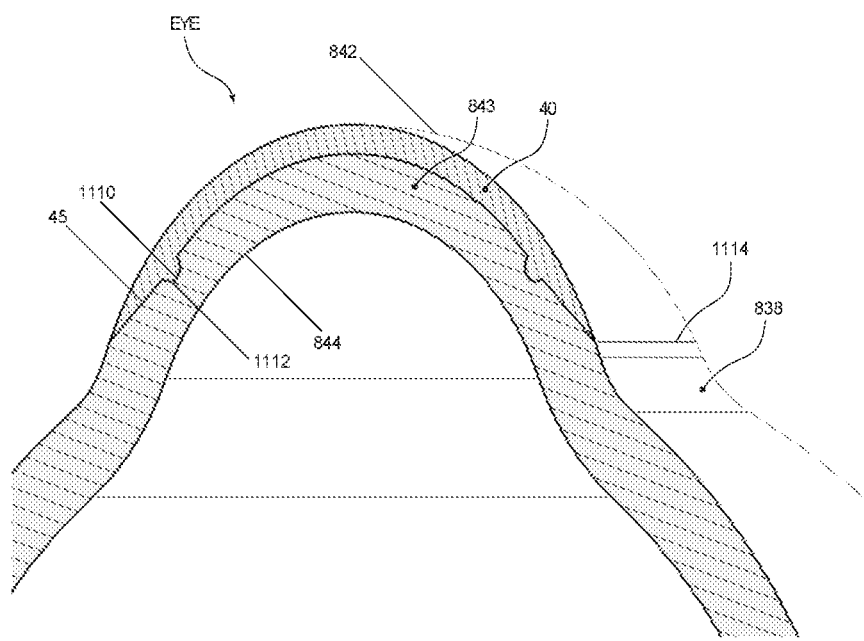

FIGS. 24A and 24B are directed at details involved in the creation and use of complementary features within a tissue 2 that may provide improved mechanical stability and better maintain a fixed relationship between elements of tissue 2 that may be at least partially separated from each other by an incision 45 using the systems and methods described herein, including when creating a lenticule or other surgical refractive correction. Thus, an incision 45 may comprise a correction portion, as is described elsewhere herein, and an additional stability portion 1108 that may comprise complementary features. A target tissue 2 may be incised along incision 45 to create a flap 40 and a bed 44 within a cornea 843, which in turn may contain an anterior surface 842 and a posterior surface 844. In the instant example, incision 45 may be configured to create nominally complementary features protrusion 1110 and indentation 1112 in flap 40 and on bed 44, respectively. Such complementary features may be configured to be at least partially interlocking and to provide stability between interface between the first side and the second side of the tissue incision profile to at least partially decrease the occurrence of a flap 40, or any other adjacent incisional element(s), from dislocating from cornea 843 ("dehiscence") during healing and may further serve to at least partially inhibit epithelial cells from invading the wound along incision edge 1114. As shown, the angle between corneal surface 842 and incision 45, whose vertex is along edge 1114, may be a fairly shallow angle, such as those that may be created when using a traditional microkeratome. In the present example, a cornea 843 of an eye EYE contains target tissue 2, although other anatomical locations and configurations are considered within the scope of the present disclosure. Although shown as such in the instant figure, flap 40 need not be completely separated from target tissue 2 and may comprise a pocket, or a hinge portion, as described elsewhere herein. When completely separated from cornea 843, flap 40 may be deemed to be a "cap." A cap may be particularly well suited for use in corneal transplantation procedures. A pocket incision may also be configured to utilize such complementary features for similar purposes. As is described elsewhere herein, an incisional system may be configured to create nominally complementary features protrusion 1110 and indentation 1112 via a surface profile of a contact plate. Alternately, such features may be created using a suction element 810 to deform the target tissue prior to and/or during the creating of an incision. Alternatively, creating an incision with an edge (equivalently, a "boundary", a "circumference", a "perimeter") that comprises an edge 1114 whose angle relative to the surface of the incised tissue is as steep (or "orthogonal", "normal") as possible may provide improved stability. This may be achieved by limiting the distance between stability portion 1108 and incision boundary 1114. This may be optimized by overlapping stability portion 1108 and incision boundary 1114. An incision depth may be chosen so that the incision will not disrupt a Bowman's membrane anteriorly or a Descemet's membrane posteriorly. An incision depth between 20% and 80% of the corneal thickness may generally suffice to provide a margin of safety. An incision profile may be considered to be the resultant surface profile of a tissue in its relaxed state after an incision. An incision profile that separates (or "excises" or "resects") a volume of tissue may correspond to a "resection" profile, as is described elsewhere herein. Complementary features may be configured such that a feature on one surface is at least partially received into a feature on an opposing surface. Alternately, a complementary feature may be intended to receive an implant such as, but not limited to, a prosthetic, an intracorneal lens, or a drug delivery device.

Figure 25:
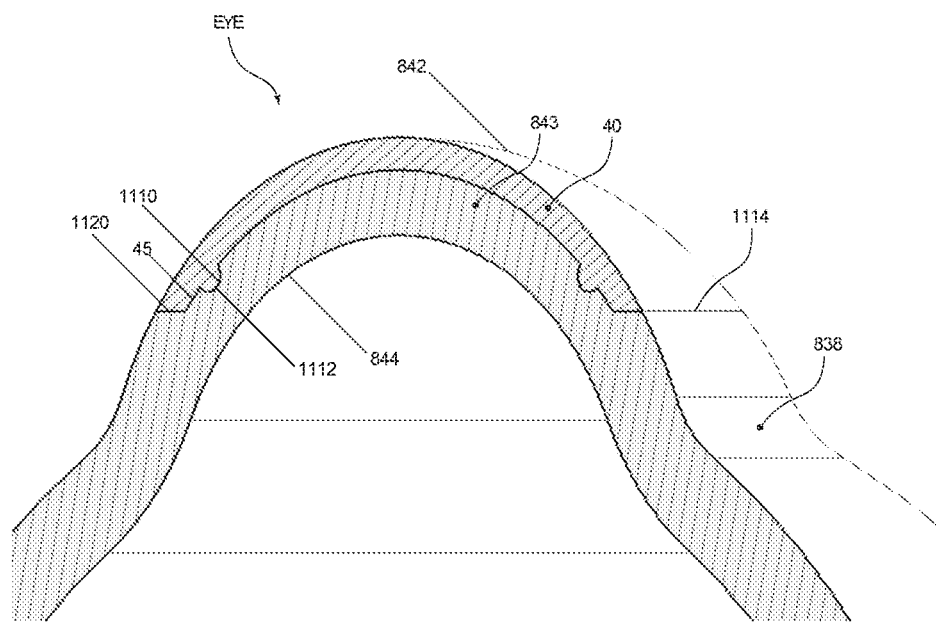
FIG. 25 depicts aspects of a corneal incision comprising complementary features in accordance with embodiments of the present disclosure.

FIG. 25 is directed at a further embodiment of the present disclosure to create and use complementary features within a tissue 2 that is similar to that of FIGS. 24A and 24B, modified to include the addition of incisional element 1120 of incision 45 to provide a steeper angle between corneal surface 842 and incision 45. Incisional element 1120 may serve to further decrease epithelial wound invasion and improve the mechanical stability of an incision 45 and at least partially maintain the relative positions of the incised target tissue(s).

Figure 26:
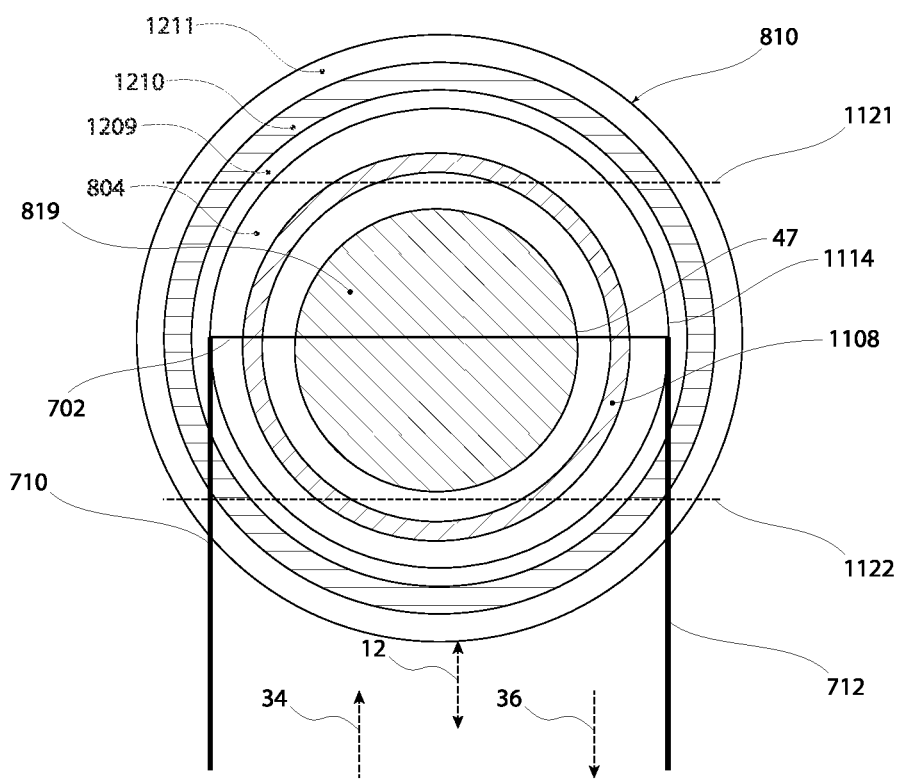
FIG. 26 depicts aspects of a system configured to create complementary features and an incision comprising complementary features in accordance with embodiments of the present disclosure.

FIG. 26 is directed at an embodiment wherein either suction element 810 and/or contact element 804 may be further configured to comprise a correction portion 819, as is described elsewhere herein, and an additional stability portion 1108. In the case of corneal incisions, said correction portion 819 may be a refractive correction, as described elsewhere herein. In the case of corneal incisions, said stability portion 1108 may be further configured to lie outside of a visual aperture 1150 (shown in subsequent figures) and may be configured to create nominally complementary features protrusion 1110 and indentation 1112 and may be created by at least a portion (or a "region") of a contact element 804 and/or by at least a portion (or a "region") of a suction element 810. Said corrective portion 819 may lie within said visual aperture 1150. Said refractive corrective portion 819 may be configured to produce a lenticule 820, by way of nonlimiting example. A tensioned electrode 702 may be supported by arms 710 & 712 to create at least an incision 45 that contains a corrective portion 819, shown as lenticule 820 bounded by incision 47 and extending beyond the visual aperture 1150 (aka an "optical clear aperture", or optical zone for refractive correction), and a stability portion 1108. The electrode may be translated along axis of motion 12 in direction 34 up to location 1121 to create an incision boundary 1114, including hinge 1020, and then translated in direction 36 to at least location 1122 to incise corrective portion 819 and at least portion of stability portion 1108. Translation along direction 36 or power to the electrode may be discontinued at location 1122 to preclude recutting redundant portions of an incision, such as the corneal incision shown. Suction channel 1210 may be utilized to secure target tissue, as has been described elsewhere herein. Regions 1209 & 1211 that may form at least a portion of surface 1200 may be configured to form a nominally flat surface 1200 or be of differing heights. For example, region 1211 may be made to stand proud of contact surface 1200.

The tissue shaping with the contact element can be performed in many ways and the contact element can be configured in many ways, for example with protrusions or channels, and combinations thereof as described herein. The tissue shaping while the incision is made allows the incision to be substantially linear while the tissue is shaped with a constrained configuration. When the contact element has been removed, the tissue can relax into a free-standing configuration such that the tissue structures imparted into the tissue with the contact element when the incision is made appear along the incision profile 45 in the free-standing configuration. This tissue shaping with the contact element allows any suitable shape, e.g. a three dimensional shape, to be formed with a substantially linear incision profile when the tissue is incised with the electrode. In some embodiments, the incision profile 45 comprises a two-dimensional linear incision profile when the tissue is engaged with the contact element, and the one or more complimentary features comprises a three-dimensional complimentary surface profile when the tissue has relaxed to the free-standing configuration, e.g. protrusion 1110 and complimentary indentation 1112.

Figure 27A:
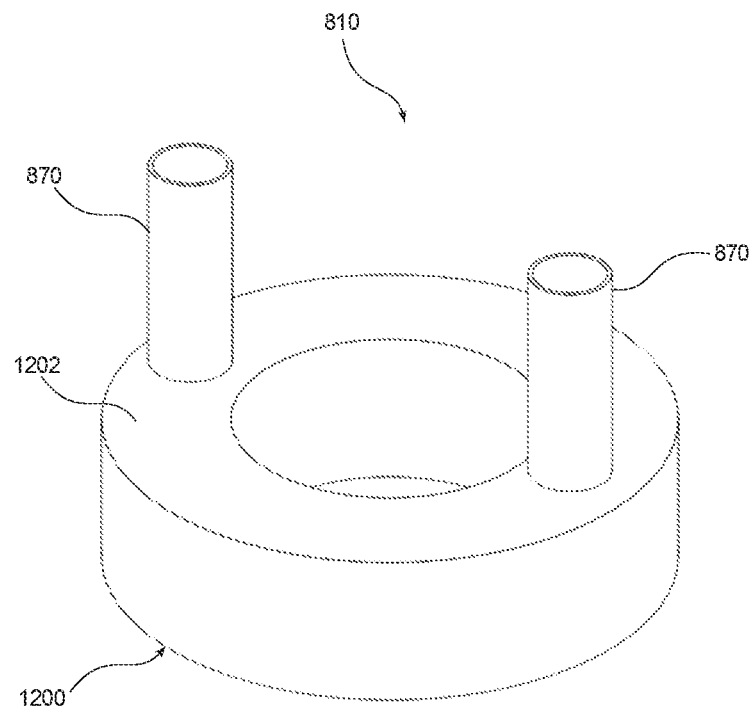
FIGS. 27A through 27C depict aspects of a suction element of a system configured to create complementary features in accordance with embodiments of the present disclosure.
Figure 27B:
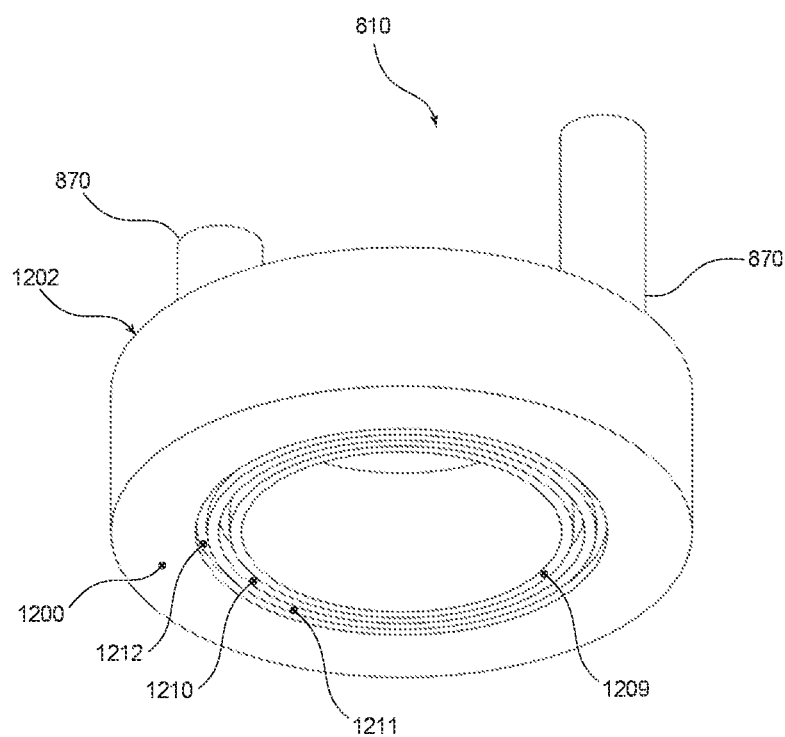
Figure 27C:
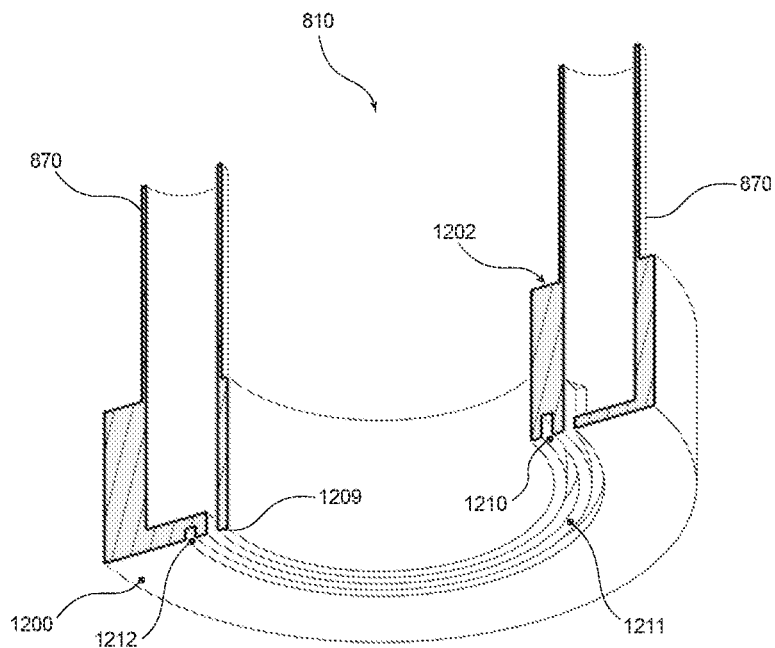

FIGS. 27A through 27C are directed at embodiments of suction element 810, that may be used to both stabilize a tissue 2 relative to a contact plate 804 (as described with respect to FIGS. 6 through 11) and/or an electrode 4 (as described with respect to FIGS. 6 through 11) and to impart complementary features to an incision 45 by drawing at least some of a tissue 2 into at least a portion of a channel 1210 (shown here as an annular ring) on suction contact surface 1200. Suction element 810 may be configured to support a nominally open annular ring for channel 1210, as shown, or alternately by any other applicable construction to achieve fixation to the eye, such as a single open pocket, or a plurality of open pockets, or a plurality of such channels 1210, and combinations thereof. Suction element 810 may be operatively coupled to vacuum pump 850 (as described with respect to FIG. 6) via vacuum line(s) 870, shown here as protruding from proximal surface 1202, to provide a negative pressure within suction element 810 and cause elements of target tissue 2 to be at least partially drawn into the open space(s) of a channel 1210 prior to and/or during the creation of an incision. A second such channel, channel 1212 has been included in this exemplary embodiment and may be utilized to evacuate fluids from target tissue 2 but is not required to practice the present disclosure. Suction lines 870 may be configured to provide the same vacuum circuit to channels 1210 & 1212, or to address them individually, as is shown in the cross-sectional view of FIG. 27C. The instant example may be configured to engage a tissue 2 immediately adjacent to or nearby a location of an incision 45 using only channel 1210 to produce the result shown in FIGS. 24A through 25 wherein protrusion 1110 and indentation 1112 are shown as nominally contiguous. In the case of a corneal incision, channel 1210 may engage the corneal surface inside of an electrode path, as opposed to outside of an electrode path on a sclera and/or a corneoscleral limbus as was previously described. As such, the tissue captured by the channel 1210 may be incised by electrode 4 as part of an incision 45 and said incision 45 may comprise a correction portion 819 and a stability portion 1108. Region 1209 may reside between the central aperture of suction element 810 and channel 1210. Region 1211 may reside between channels 1210 & 1212. The width (radial in the instant example) of a channel 1210 may be configured to be between ~50 μm and ~500 μm, such that the correlated resultant widths of complementary features protrusion 1110 and indentation 1112 may be between ~30 μm and ~500 μm. Similarly, the depths of a channel 1210 may be configured to be between ~50 μm and ~500 μm, such that the correlated resultant height of protrusion 1110 and the depth of indentation 1112 may be between ~30 μm and ~450 μm. Regions 1209 & 1211 may be configured to deviate from the height of each other and/or that of surface 1200 by between ~+30 μm and ~+200 μm. The vacuum pressure used to achieve such results may be between ~−100 mmHg and ~−600 mmHg.

Figure 28A:
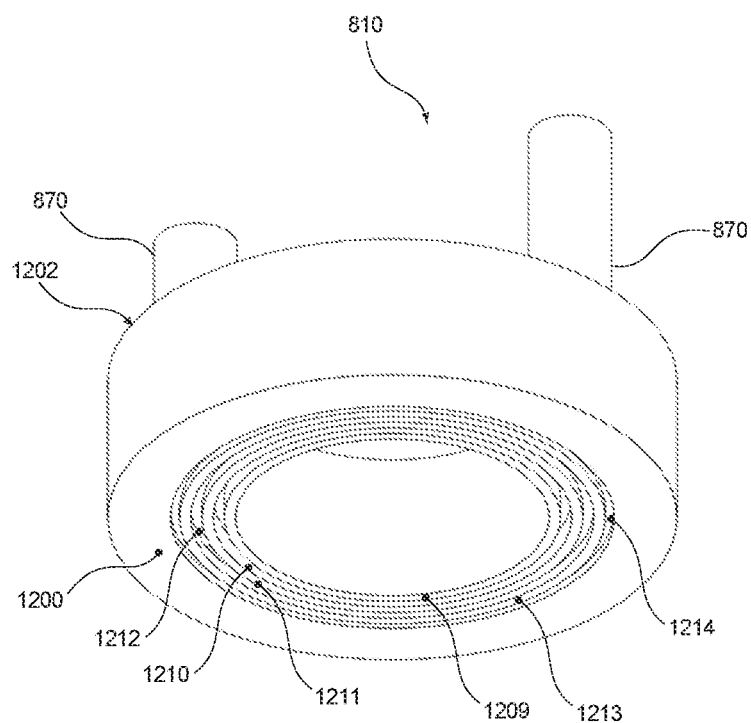
FIGS. 28A and 28B depict aspects of a suction element of a system configured to create complementary features in accordance with embodiments of the present disclosure.
Figure 28B:
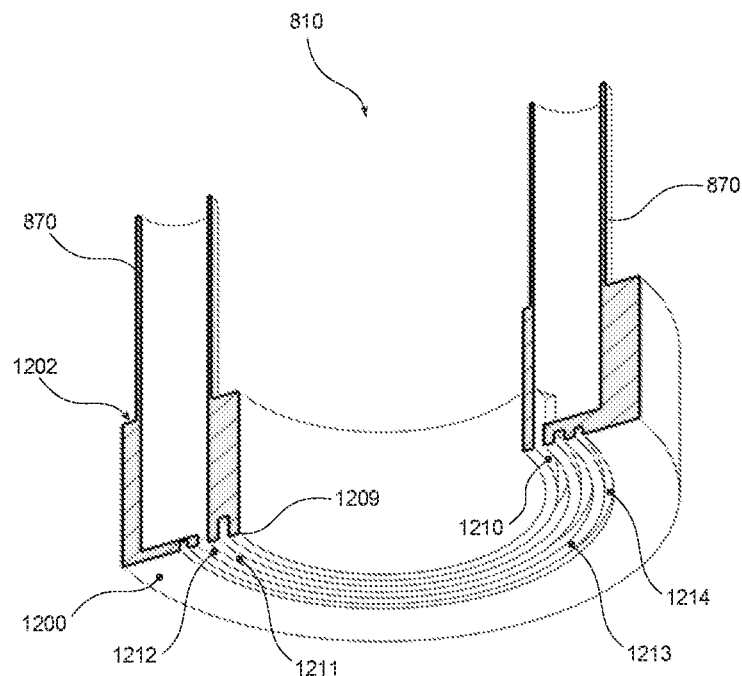

FIGS. 28A-28B are directed at further embodiments of suction element 810, similar to those of FIGS. 27A-27C, with the addition of a channel 1214 that is not configured to provide suction to tissue 2. Instead, a channel 1214 may be located adjacent to or nearby a channel 1210. Although shown in the instant exemplary embodiment as being located radially beyond channels 1210 and 1212, a channel 1214 may be alternately located between channels 1210 and 1212. A width and/or a depth of a channel 1214 may be configured to be between ~50 μm and ~500 μm, such that the correlated resultant width and/or a depth/height of protrusions 1110 and indentations 1112 may be between ~30 μm and ~450 μm when a vacuum gauge pressure of between ~-100 mmHg and ~-600 mmHg is used to provide suction to at least one of channels 1210 and 1212. Channels 1210 and 1212, and 1214 may be (radially, in this example) separated by between ~200 μm and ~1000 μm. Regions 1209, 1211, and 1213 may be configured to deviate from each other and/or that of an otherwise flat surface 1200 by between ~+30 μm and ~+200 μm. Although shown as nominally regular annular channels 1210, 1212, and 1214 need not be regular and configured with varying widths and/or depths.

Figure 29:
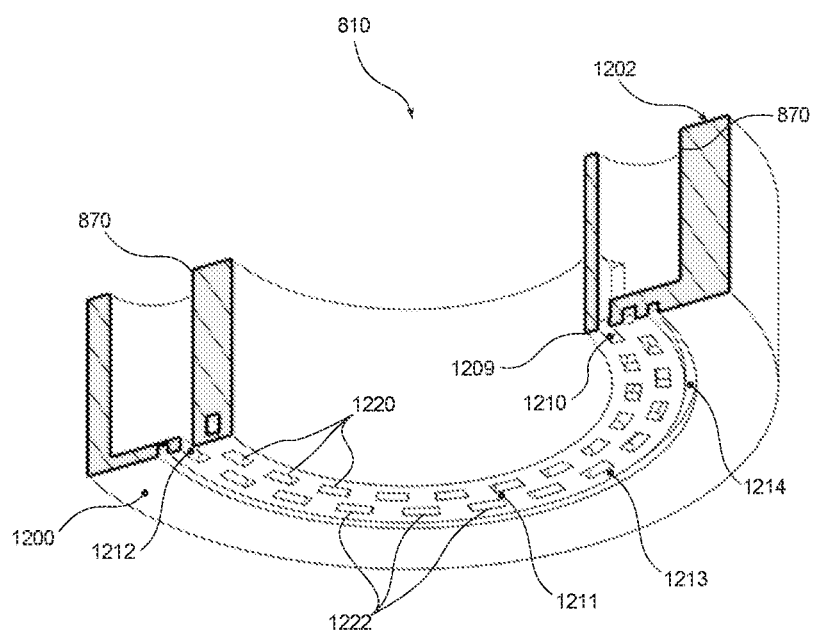
FIG. 29 depicts aspects of a suction element of a system configured to create complementary features in accordance with embodiments of the present disclosure.

FIG. 29 is directed at a further embodiment similar to that of FIGS. 27A through 28B, with the modification that channels 1210 and 1214 are not configured as regular annular channels. In the instant example, channels 1210 & 1212 comprise a plurality of openings 1220 & 1222, respectively. Such a configuration may yield a plurality of corresponding protrusions 1110 and indentations 1112 for channels 1210 & 1212, and a nominally contiguous protrusion 1110 and indentation 1112 corresponding to channel 1214. Openings 1220 & 1222 may be configured to utilize widths between ~50 μm and ~500 μm, lengths between ~50 μm and ~3000 μm, and with a (radial, in this example) separation of between ~200 μm and ~1000 μm. Additionally, suction lines 870 are shown as not protruding beyond proximal surface 1202.

Figure 30:
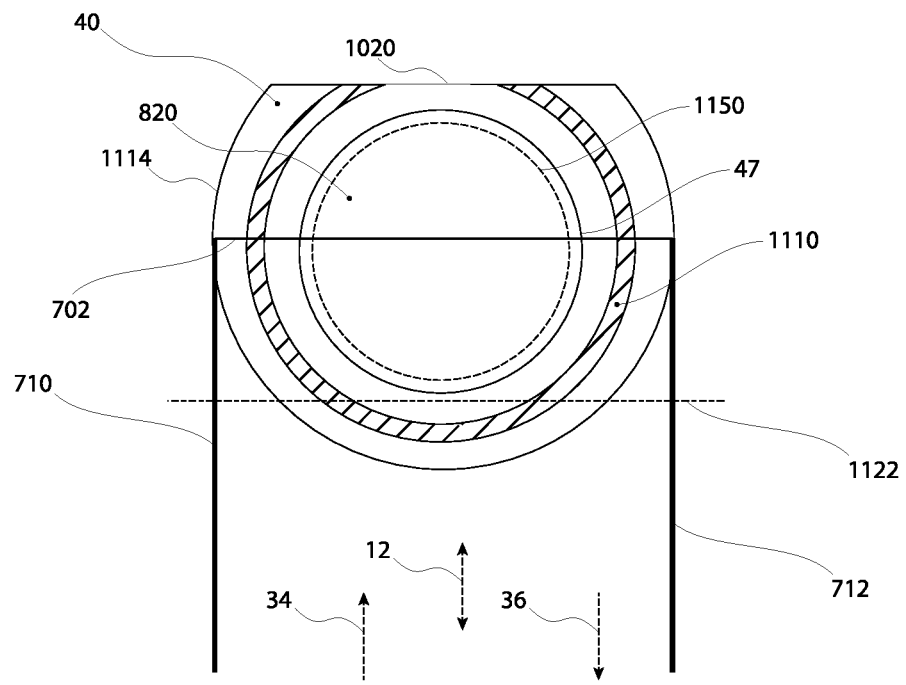
FIG. 30 depicts aspects of a system configured to create complementary features and an incision comprising complementary features in accordance with embodiments of the present disclosure.

FIG. 30 shows an embodiment wherein a target tissue 2 may be incised along axis of motion 12 by tensioned electrode 702 that may be supported by arms 710 & 712 to create via incisions 45 & 46 (as described with respect to FIG. 19A) a flap 40 that contains a corrective portion. Shown as lenticule 820 bounded by incision 47 and extending beyond the visual aperture 1150 (aka an "optical clear aperture"), and a stability portion 1108, shown as comprising a protrusion 1110. Flap 40 is configured to comprise boundary 1114, which includes hinge 1020, and may be incised along axis of motion 12, comprising directions 34&36, as described elsewhere herein. Although not shown for the sake of clarity, it should be understood that complementary features for the stability portion 1108 of the incision may be present beneath a flap incision as described herein.

Figure 31A:
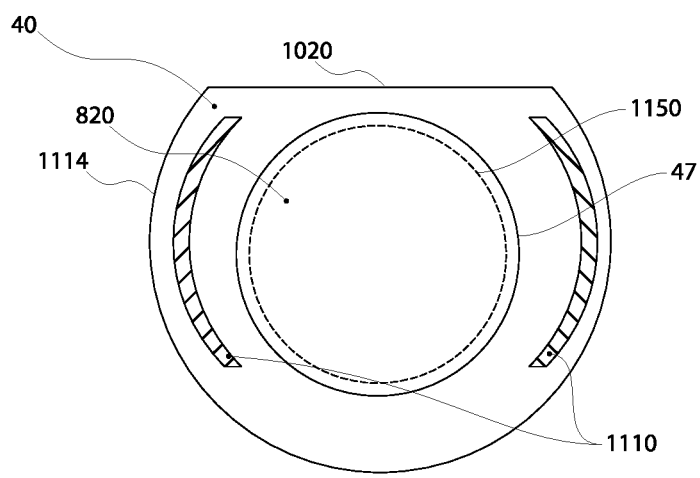
FIGS. 31A through 31C depict aspects of an incision comprising complementary features in accordance with embodiments of the present disclosure.
Figure 31B:
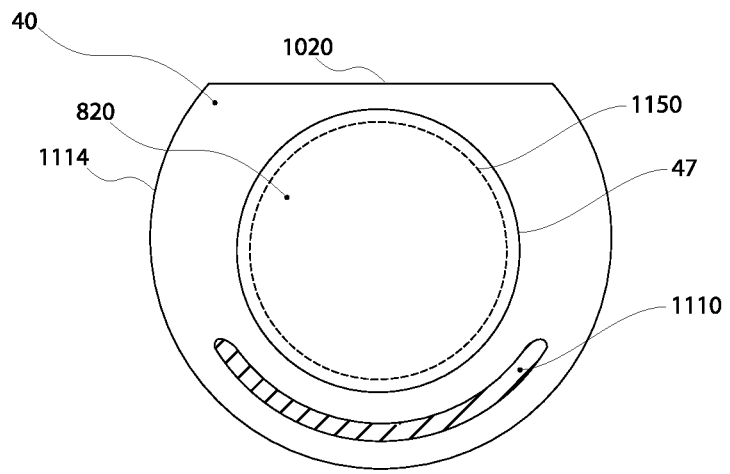
Figure 31C:
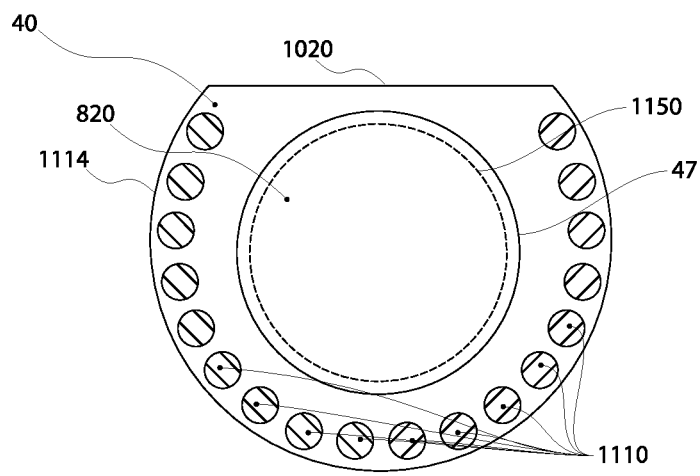

FIGS. 31A through 31C are directed at alternative embodiments of the present disclosure that are similar to that of FIG. 30, but further comprising a variety of configurations for creating a stability portion 1108 of an incision. FIG. 31A is directed at a stability portion 1108 comprising protrusions 1110 that may be configured to be constrained to be outside of the corrective portion of the incision (as may be defined by the boundary 1150 and/or incision 47) with respect to an axis of motion 12. Alternatively, FIG. 31B is directed at a configuration for a protrusion 1110 that may be configured to be located nominally opposite from hinge 1020, as hinge 1020 itself inherently provides a certain amount of stability against dislocation of flap 40. Said inherent stability may be a function of the size and/or length of hinge 1020. Alternatively, FIG. 31C is directed at configuration for a stability portion 1108 that may be configured to comprise a plurality of protrusions 1110.

Figure 32A:
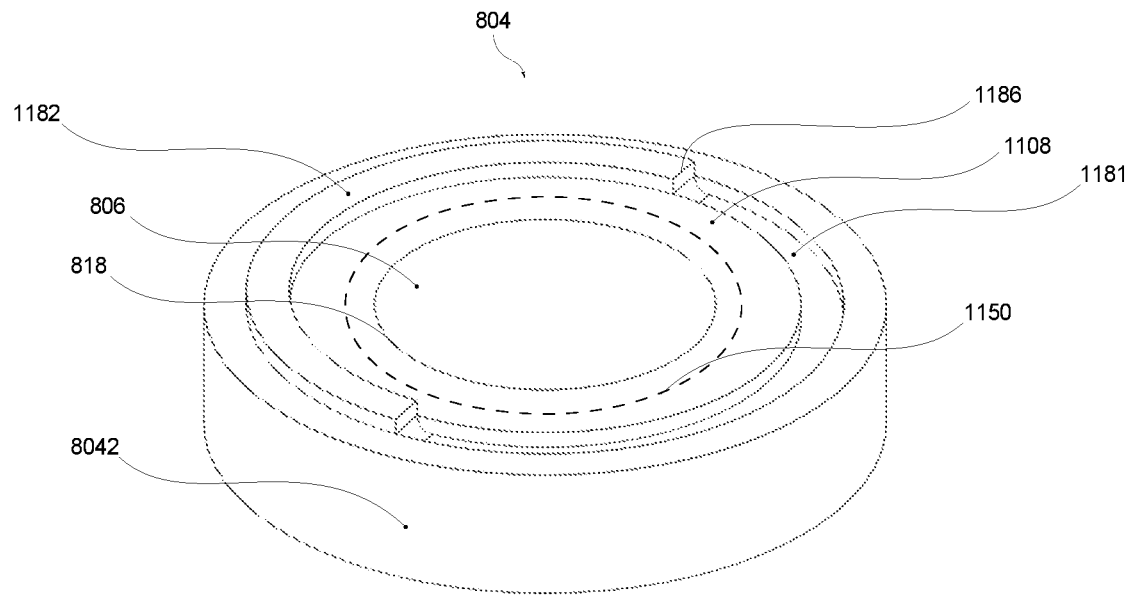
FIGS. 32A and 32B depict aspects of a contact element of a system configured to create complementary features in accordance with embodiments of the present disclosure.
Figure 32B:
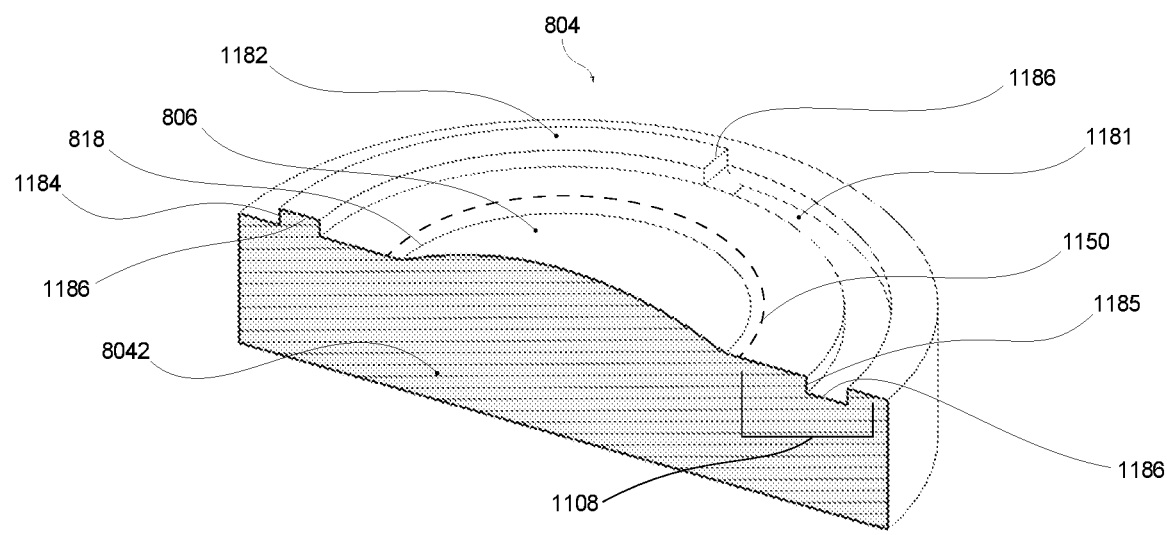

FIGS. 32A and 32B are directed at an exemplary embodiment wherein a contact element 804 further comprises a variety of configurations for creating one or more stability portions 1108, of an incision. As shown in FIG. 32A, a contact element 804 may be configured to provide a correction portion 819 to an incision, as is described elsewhere herein, via at least a portion of contact surface 806, which may be considered as a "corrective portion" and bounded by boundary 818 and lies inside of a visual aperture 1150. Contact element 804 may be further configured to comprise a stability portion 1108, or stability portions 1108, that lie(s) outside of a visual aperture 1150. Stability portion 1108 may be further configured to create nominally complementary features such as a protrusion 1110 by deforming (or, equivalently, "shaping") tissue with recess 1181 and/or an indentation 1112 by shaping tissue using protuberance 1182, respectively. Recess 1181 may be configured to have a width 1186 and a depth 1185, as shown in FIG. 32B. Likewise, protuberance 1182 may be configured to have a width 1186 and a height 1185. Recesses 1181 and protuberances 1182 may be configured to utilize widths between ~50 μm and ~1500 μm, heights between ~50 μm and ~700 μm, and depths of between ~50 μm and ~700 μm. Recesses 1181 and protuberances 1182 may be further configured to utilize widths between ~200 µm and ~600 µm, heights between ~100 µm and ~300 µm, and depths of between ~100 µm and ~300 µm.

FIG. 32B shows a cross-sectional view of the embodiment of FIG. 32A, in which surface 806 may be seen to be hemispherical, as may be used to correct for simple myopia when the present disclosure is deployed to create a corneal lenticule, for example. Stability portion (or, equivalently, "stability region") 1108 may be seen to comprise the region beyond about optical clear aperture 1150 and about the edge of contact element 804 bounded by housing 8042. It is to be understood that various combinations of such recesses 1181 and protuberances 1182 may be combined to form a more complex stability portion 1108.

Figure 33:
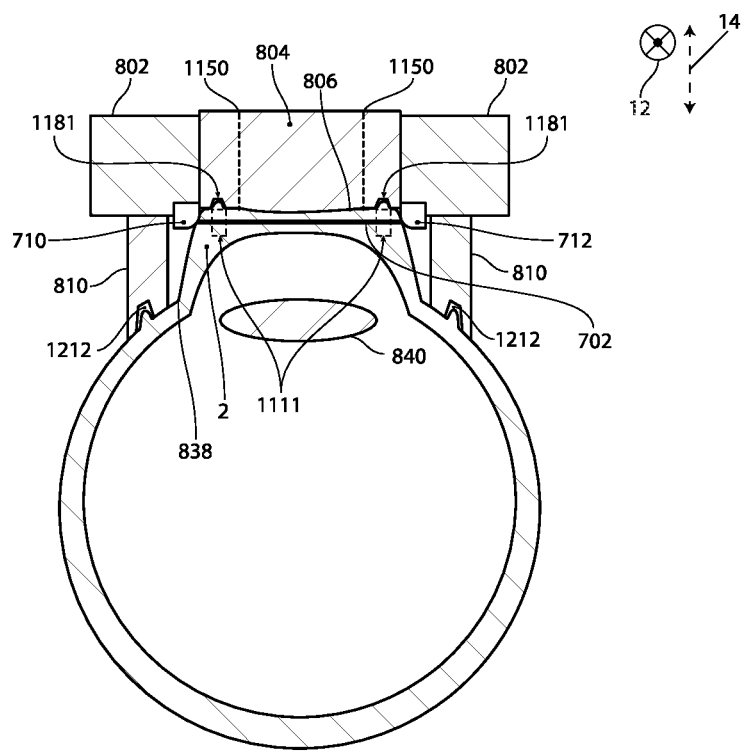
FIG. 33 depicts aspects of a system comprising a contact element configured to create complementary features in accordance with embodiments of the present disclosure.

FIG. 33 is directed at an embodiment comprising aspects of those shown in FIGS. 10A through 10F and FIGS. 26 through 30, configured to create an incision comprising both a corrective portion 1108 and a stability portion 819, which may further comprise complementary features protrusion 1110 and indentation 1112, as is shown in FIGS. 24A through 26. Contact plate 804 may comprise an indentation 1181 (or, equivalently as used herein, a "channel") that may be made to contact the tissue surface, reshaping the tissue surface from that of its free-standing state and affect at least a portion of an underlying volume of tissue 1111 (nominally in and around the region enclosed by the dashed lines as shown) to create a protrusion 1110 and a complementary indentation 1112 in different aspects of an incision, such as a flap and a bed, respectively, in the case of the exemplary corneal incision. More broadly, an incision created through at least a portion of underlying tissue volume 1111 along an incision profile may create a first incisional surface that is proximal to the tissue surface, and a second incisional surface that is distal to the tissue surface. Said incisional profile may planar when the tissue has been shaped with the contact element, such as when an elongate electrode is advanced and/or retracted along a nominally linear path as has been elsewhere herein. The subsequent resultant free-standing (or "relaxed") tissue shape may be considered to be an opposite to the shape imparted to the tissue during the incision. Shaping a tissue into a configuration that is more concave than that of its normal relaxed state during an incision, such as a nominally planar incision, may result in less concave (or, equivalently, a more convex) tissue shape when that tissue is later returned to a relaxed tissue shape. Shaping a tissue into a configuration that is more convex than that of its normal relaxed state during an incision, such as a nominally planar incision, may result in less convex (or, equivalently, a more concave) tissue shape when that tissue is later returned to a relaxed tissue shape. A resultant shape may be imparted to the tissue, particularly during an incision while a contact element is engaged and shapes a tissue surface, and/or a volume of tissue that underlies the tissue surface differently than that of its (their) relaxed state(s). A tissue contact element 804 may shape the tissue sufficiently to allow that tissue to form one or more complimentary features along the incision profile when the tissue relaxes to its altered free-standing configuration with removal of the tissue contact element and/or the pressure thereon. Optical clear aperture 1150 may be defined as a region that lies between the dashed lines 1150 shown this cross-sectional view, and the resulting incision may have both a corrective portion 819 and a stability portion 1108. In some embodiments, the optical clear aperture 1150 comprises an optical zone of refractive correction, the outer boundary of which corresponds to a perimeter of the incised lenticule. Said stability portion may be defined as a region outside of the corrective portion, which may also be outside of the optical clear aperture. A tissue 2 may be drawn into channel 1212 of suction element 810 by suction to affix and/or stabilize the tissue 2. Channel 1212 may lie outside of the incision boundary 1114 (not shown for clarity but may be considered as the region defined by the intersection of electrode 702 and tissue 2) and thus not contribute to the creation of a stability portion 1108 of an incision.

Figure 34:
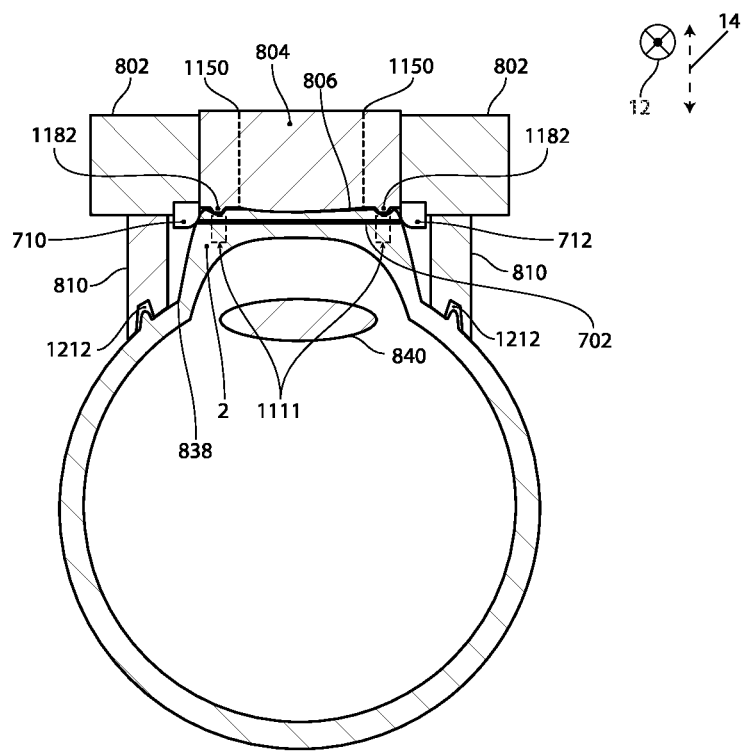
FIG. 34 depicts aspects of a system comprising a contact element configured to create complementary features in accordance with embodiments of the present disclosure.

FIG. 34 is directed at an embodiment similar to that of FIG. 33, with contact plate 804 modified to include protrusion 1182 that may be made to contact the tissue surface, reshaping the tissue surface and affect at least a portion of an underlying volume of tissue 1111 to create a indentation 1112 and a complementary protrusion 1110 in different aspects of an incision, such as a flap and a bed, respectively, in the case of the exemplary corneal incision.

Figure 35:
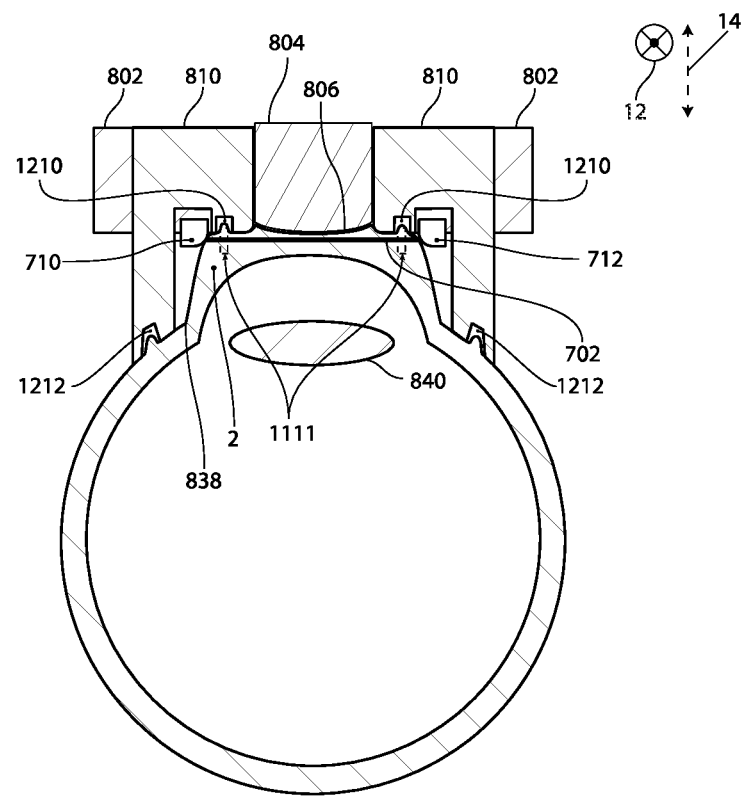
FIG. 35 depicts aspects of a system comprising a suction element configured to create complementary features in accordance with embodiments of the present disclosure.

FIG. 35 is directed at an embodiment similar to that of FIG. 33. As described previously herein, a tissue 2 may be drawn into channel 1210 by suction supplied by suction element 810 to create complementary features 1110 and 1112 within stability region 1108. Channel 1212 may lie outside of the incision boundary 1114 (not shown for clarity but may be considered to be outside of the region defined by the intersection of electrode 702 and tissue 2 and being disposed between channels 1210 and 1212 in the instant exemplary embodiment). Tissue 2 may be drawn into channel 1210 and disposed within a cutting region, shown in the instant exemplary embodiment as being "above" electrode 702 to constitute protrusion 1110 and indentation 1112, whereas the tissue 2 drawn into channel 1212 may be disposed "below" said electrode and outside of a cutting region and thereby not incised. The optical clear aperture 1150 (as described with respect to FIG. 26 and FIGS. 30 through 33) may be considered to be about the width of contact plate 804 in the instant exemplary embodiment.

Figure 36:
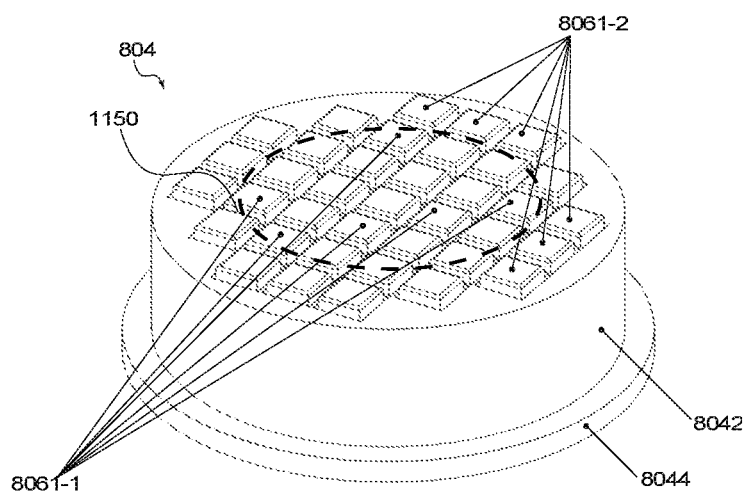
FIG. 36 depicts aspects of an adjustable contact element configured to create complementary features in accordance with embodiments of the present disclosure.

FIG. 36 is directed at an embodiment similar to that of FIGS. 11A and 11B, with the addition of optical clear aperture 1150 which may divide elements 8061 into two regions: region 1 being within (or "inside of") the optical aperture intended for providing a refractive surface to create a lenticule, elements 8061-1, and region 2, those without (or "outside of") the optical clear aperture, elements 8061-2. Elements 8061-2 may be configured to provide complementary features for producing a stability portion 819 of an incision.

Because a typical cornea may be on average ~500 µm thick and may require that at least ~250 µm of the corneal stroma remain to prevent causing instability or out-bulging ("eklasisa") at common IOPs, creating a protrusion in/on a corneal bed may be preferred over creating a protrusion in/on a flap. Alternately, configuring the system to create an indentation in/on a corneal bed that results in a stromal thickness of ~≥250 µm may be preferred.

Creating a stability portion of an incision that is located opposite to a hinge portion may provide more stability than those more closely adjacent to said hinge portion.

While the shape of the complementary features shown herein are predominantly rectangular in depth-cross-section, other shapes are considered within the scope of the present disclosure. By way of non-limiting example, the depth-cross-sectional shape of a complementary features may be selected from the group consisting of a protrusion, a recess, an indentation, a rectangle, a rounded-rectangle, a circle, an ellipse, a quadrilateral, a rhombus, a parallelogram, a trapezoid, a trapezium, a closed curve, and a combination thereof.

Any incisional instrument, such as a conventional microkeratome (or a device of equivalent function) may also be used to create an incision comprising a stability portion. For example, a conventional microkeratome may be modified to create a corneal flap that further comprises a stability portion by providing at least one of channels 1210 and/or 1212 to the device's suction element and/or at least one of recesses 1181 and protuberances 1182 to the device's applanation plate such that they are impinged by the cutting element of the incision device to create complementary features of an incision.

Referring again to FIGS. 24A to 26 and 33 to 36, the system can be configured in many ways to incise tissue. In some embodiments, the processor is configured to perform one or more steps of a method. In some embodiments, a processor such as a controller is configured to advance and retract the electrode in response to processor-controlled movements. In some embodiments, the tissue contact element is configured to shape tissue with suction element 810 and channels 1210, and the tissue is incised with advancement and retraction of the electrode. In some embodiments, the tissue surface comprises a first surface profile corresponding to a first tissue resection profile while the electrode is advanced and a second surface profile while the electrode is retracted to define a volume of resected tissue corresponding to a difference between the first surface profile and the second surface profile as described herein. In some embodiments, the volume of resected tissue corresponds to corrective portion 819 within stability portion 1108 of the profile of incision 45 as described herein.

In some embodiments, the tissue contact element comprises an adjustable contact element configured to shape the tissue to a first surface profile to incise the tissue along a first tissue incision profile and to a second surface profile to incise the tissue along a second incision profile. In some embodiments, the adjustable contact element comprises elements 8061 as described herein. In some embodiments, elements 8061 comprise first elements 8061-1 to define a first surface profile and a second surface profile of corrective portion 819, e.g. when the electrode is advanced and retracted, and second elements 8061-2 remain substantially fixed while the electrode is advanced and retracted to define the complementary features of a stability portion 1108 with incision 45.

This tissue shaping with the contact element allows any suitable shape, e.g. a three dimensional shape, to be formed with a substantially linear incision profile when the tissue is incised with the electrode. In some embodiments, the incision profile 45 comprises a two-dimensional linear incision profile when the tissue is engaged with the contact element, and the one or more complimentary features comprises a three-dimensional complimentary surface profile when the tissue has relaxed to the free-standing configuration, e.g. protrusion 1110 and complimentary indentation 1112.

Combinations of the above configurations are also considered within the scope of the present disclosure.

As used herein, the terms "flex", "deform", "vibrate", "stretch", and "bend" may be used interchangeably.

As used herein in reference to tissue interactions, the terms "disrupt", "breakdown", and "ablate" may be used interchangeably.

The symbol "~" is used herein as equivalent to "about". For example, a statement such as "~100 ms" is equivalent to a statement of "about 100 ms" and a statement such as "$V_t$=~5 mm·s$^{-1}$" is equivalent to a statement of "$V_t$ is about 5 mm·s$^{-1}$."

The symbol "Ø" is used herein to indicate the following value is a diameter. For example, a statement such as "Ø10 µm" is equivalent to a statement of "a diameter of 10 µm." Furthermore, a statement such as "~Ø12 µm" is equivalent to a statement of "a diameter of about 12 µm."

The symbol "∝" is used herein to indicate proportionality. For example, a statement such as "∝r$^{-2}$" is equivalent to the statement "proportional to r$^{-2}$."

Dot notation is used herein to represent compound units for the sake of clarity and brevity. For example, the statement k=~40N·m$^{-1}$ is equivalent to the statement "k=~40 N per meter."

As used herein "mN" refers to "milli Newtons", which is 10$^{-3}$ Newtons.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally, or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively, or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection.

Unless otherwise noted, the terms "operatively connected to" and "operatively coupled to" (and their derivatives), as used in the specification and claims, are to be construed as permitting both direct and indirect (i.e., via other elements or components) connection to perform a function.

In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising."

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

Drawings are not necessarily drawn to scale and some dimensions may be disproportionately represented for purposes of illustration.

The present disclosure includes the following numbered clauses.

Clause 1. A method of incising tissue, the method comprising: shaping a tissue surface with a tissue contact element comprising one or more of a channel or a protrusion to form one or more of a corresponding protrusion or indentation in the tissue surface; incising the tissue along a tissue incision profile; and removing the contact element to allow the tissue to relax to a free-standing configuration and form one or more complimentary features along the tissue incision profile.

Clause 2. The method of clause 1, wherein the one or more complimentary features comprises a protrusion on a first side of the tissue incision profile and an indentation on a second side of the incision profile to stabilize the tissue in the free-standing configuration at an interface between the first side and the second of the tissue incision profile.

Clause 3. The method of clause 2, wherein the tissue incision profile defines a first portion of tissue on a first side of the incision profile and a second portion on a second side of the incision profile and wherein the first portion comprises one or more protrusions and the second portion comprises one or more corresponding indentations sized and shaped to receive the one or more protrusions in the free-standing configuration.

Clause 4. The method of clause 3, wherein the one or more protrusions comprises a plurality of protrusions on the first side of the incision profile and the one or more corresponding indentations comprises a plurality of corresponding indentations on the second side of the incision profile in the freestanding configuration.

Clause 5. The method of clause 4, wherein the plurality of protrusions and the plurality of indentations comprise a plurality of interlocking features.

Clause 6. The method of clause 3, wherein the first portion comprises the tissue surface and the second portion comprises a bed of tissue.

Clause 7. The method of clause 3, wherein the second portion comprises the tissue surface and the first portion comprises a bed of tissue.

Clause 8. The method of clause 1, wherein the one or more of the channel or the protrusion of the contact element comprises a channel and wherein the channel is sized to receive the tissue surface to form a corresponding protrusion along the tissue incision profile in the free-standing configuration.

Clause 9. The method of clause 8, wherein the tissue incision profile defines a first portion of tissue on a first side of the incision profile and a second portion on a second side of the incision profile and wherein the first portion comprises the protrusion and the second portion comprises a corresponding indentation sized and shaped to receive the protrusion.

Clause 10. The method of clause 9, wherein the protrusion on the first portion and the indentation on the second portion comprise an interlocking configuration.

Clause 11. The method of clause 1, wherein the one or more of the channel or the protrusion of the contact element comprises a protrusion and wherein the protrusion is sized to indent the tissue surface to form a corresponding indentation along the tissue incision profile in the free-standing configuration.

Clause 12. The method of clause 11, wherein the tissue incision profile defines a first portion of tissue on a first side of the incision profile and a second portion on a second side of the incision profile and wherein the first portion comprises the indentation and the second portion comprises a corresponding protrusion sized and shaped to fit into the indentation.

Clause 13. The method of clause 12, wherein the indentation on the first portion and the protrusion on the second portion comprise an interlocking configuration.

Clause 14. The method of clause 1, wherein the incision profile comprises a linear incision profile when the tissue is incised with the electrode.

Clause 15. The method of clause 14, wherein the incision profile comprises a two-dimensional linear incision profile when the tissue is engaged with the contact element and wherein the one or more complimentary features comprises a three-dimensional complimentary surface profile when the tissue has relaxed to the free-standing configuration.

Clause 16. The method of clause 1, wherein the one or more complimentary features comprise one or more of interlocking features or mating features.

Clause 17. The method of clause 1, wherein the one or more complimentary features extends along an outer region of the tissue incision profile and at least partially around an in inner region of the tissue incision profile.

Clause 18. The method of clause 17, wherein the one or more complimentary features extend semi circumferentially around the inner region of the incision profile.

Clause 19. The method of clause 1, wherein the one or more complimentary features extends along an outer region of the tissue incision profile to define a central optical zone of a cornea of an eye.

Clause 20. The method of clause 1, tissue is incised with advancement and retraction of the electrode and wherein the tissue surface comprises a first surface profile corresponding to a first tissue resection profile while the electrode is advanced and a second surface profile while the electrode is retracted to define a volume of resected tissue corresponding to a difference between the first surface profile and the second surface profile.

Clause 21. The method of clause 20, wherein the tissue contact element comprises an adjustable contact element and the tissue surface is shaped to the first surface profile and the second surface profile with the adjustable contact element.

Clause 22. The method of clause 21, wherein the adjustable contact element comprises inner elements to define the first surface profile and the second surface profile and outer elements to define the one or more complimentary features.

Clause 23. The method of clause 20, wherein a first portion of the tissue surface corresponding to the one or more complimentary features remains substantially fixed while the tissue is incised with advancement of the electrode and retraction of the electrode and a second portion of the tissue surface comprises the first surface profile while the electrode is advanced and the second surface profile while the electrode is retracted.

Clause 24. The method of clause 23, wherein the second portion of the tissue surface corresponds to an optical zone to correct refractive error of an eye.

Clause 25. The method of clause 24, wherein a difference between the first surface profile and the second surface profile corresponds to a change in optical power of an optical zone.

Clause 26. The method of clause 23, wherein resected tissue is removed from the volume of resected tissue.

Clause 27. The method of clause 26, wherein the resected tissue comprises corneal tissue and the tissue removed from the volume comprises a lenticule.

Clause 28. The method of clause 26, wherein the volume corresponds to a volume of an implant to be placed in the tissue.

Clause 29. The method of clause 1, wherein the one or more complimentary features comprise a width within a range from about 30 µm to about 500 µm and a depth within a range from about 30 µm to about 450 µm.

Clause 30. The method of clause 29, wherein the one or more complimentary features comprise a length within a range from about 50 µm to about 3000 µm.

Clause 31. The method of clause 29, wherein the one or more complimentary features comprises a plurality of complimentary features separated by a distance within a range from about 200 µm to about 1000 µm.

Clause 32. The method of clause 1, wherein the one or more complimentary features comprises a protrusion on a first side of the incision profile and an indentation on a second side of the incision profile shaped to receive the protrusion.

Clause 33. The method of clause 32, wherein the one or more of the channel or the protrusion of the contact element comprises a width within a range from about 50 µm to about 500 µm and the protrusion on the first side of the incision profile and the indentation on the second side of the incision profile each comprises a width within a range from about 30 µm to about 500 µm.

Clause 34. The method of clause 32, wherein the one or more of the channel or the protrusion of the contact element comprises a depth within a range from about 50 µm to about 500 µm and the protrusion on the first side of the incision profile and the indentation on the second side of the incision profile each comprises a depth within a range from about 30 µm to about 450 µm.

Clause 35. The method of clause 32, wherein the one or more of the protrusion or the channel of the contact element comprises a plurality of channels or protrusions separated by a distance within a range from about 200 µm to about 1000 µm and wherein the protrusion on the first side of the incision comprises a plurality of protrusions separated by a distance within a range from about 200 µm to about 500 µm and the indentation on the second side of the incision comprises a plurality of indentations separated by a corresponding distance within a range from about 200 µm to about 1000 µm.

Clause 36. The method of clause 1, wherein the one or more of the protrusion or the channel comprises a plurality of channels shaped to engage the tissue, each of the plurality of channels comprising a width within a range from about 50 µm to about 500 µm, a length within a range from about 50 µm to about 3000 µm, and wherein the plurality of channels is separated by a distance within a range from about 200 µm about to 1000 µm.

Clause 37. The method of clause 1, wherein the one or more of the protrusion or the channel comprises a plurality of protrusions shaped to engage the tissue, each of the plurality of protrusions comprising a width within a range from about 50 µm to about 500 µm, a length within a range from about 50 µm to about 3000 µm, and wherein the plurality of protrusions is separated by a distance within a range from about 200 µm about to 1000 µm.

Clause 38. The method of clause 1, wherein the contact element is coupled to a vacuum source to engage the tissue with the contact element.

Clause 39. The method of clause 38, wherein the one or more of the channel or the protrusion comprises a channel coupled to the vacuum source to draw tissue into the channel to shape the tissue surface with a corresponding protrusion of the tissue surface.

Clause 40. The method of clause 38, wherein the one or more of the channel or the protrusion comprises the protrusion, the protrusion coupled to a channel coupled to the vacuum source in proximity to the protrusion to form a corresponding indentation in the tissue surface.

Clause 41. The method of clause 38, wherein the vacuum source provides a vacuum pressure within a range from about 100 mm Hg to about 600 mm Hg.

Clause 42. The method of clause 1, wherein the electrode comprises an elongate electrode configured to flex and generate the plasma to incise the tissue, an electrical energy source is operatively coupled to the elongate electrode and provides electrical energy to the electrode to generate the plasma, and a tensioning element is operatively coupled to the elongate electrode and provides tension to the elongate electrode to allow the elongate electrode to flex in response to the elongate electrode engaging the tissue and generating the plasma.

Clause 43. The method of clause 42, wherein a plurality of arms is operatively coupled to the electrode and the tensioning element.

Clause 44. The method of clause 43, wherein the electrode is unsupported between the two arms.

Clause 45. A system for incising tissue with a plasma, comprising: an elongate electrode configured to incise the tissue along a tissue incision profile; and a tissue contact element configured to shape the tissue, the tissue contact element comprising one or more of a channel or a protrusion to form one or more of a corresponding protrusion or indentation in a tissue surface while the tissue is incised with the electrode along the incision profile, wherein the tissue contact element shapes the tissue sufficiently to allow the tissue to form one or more complimentary features along the incision profile when the tissue relaxes to a free-standing configuration with removal of the tissue contact element.

Clause 46. The system of clause 45, wherein the one or more complimentary features comprises a protrusion on a first side of the tissue incision profile and an indentation on a second side of the incision profile to stabilize the tissue in the free-standing configuration at an interface between the first side and the second of the tissue incision profile.

Clause 47. The system of clause 46, wherein the tissue incision profile defines a first portion of tissue on a first side of the incision profile and a second portion on a second side of the tissue incision profile and wherein the first portion comprises the protrusion and the second portion comprises a corresponding indentation sized and shaped to receive the protrusion.

Clause 48. The system of clause 47, wherein the first portion comprises the tissue surface and the second portion comprises a bed of tissue.

Clause 49. The system of clause 47, wherein the second portion comprises the tissue surface and the first portion comprises a bed of tissue.

Clause 50. The system of clause 45, wherein the one or more of the channel or the protrusion of the contact element comprises a channel and wherein the channel is sized to receive the tissue surface to form a corresponding protrusion and indentation along the tissue incision profile in the free-standing configuration.

Clause 51. The system of clause 45, wherein the one or more of the channel or the protrusion of the contact element comprises the protrusion and wherein the protrusion is sized to indent the tissue surface to form a corresponding protrusion and indentation along the tissue incision profile in the free-standing configuration.

Clause 52. The system of clause 45, further comprising: an actuator to translate the electrode.

Clause 53. The system of clause 52, wherein the tissue incision profile comprises a linear incision profile when the tissue is incised with translation of the electrode.

Clause 54. The system of clause 53, wherein the tissue incision profile comprises a two-dimensional linear incision profile when the tissue is engaged with the contact element and wherein the one or more complimentary features comprises a three-dimensional complimentary surface profile when the tissue has relaxed to the free-standing configuration.

Clause 55. The system of clause 45, wherein the tissue contact element comprises an adjustable contact element configured to shape the tissue to a first surface profile to resect the tissue along a first tissue resection profile and to a second surface profile to resect the tissue along a second incision profile.

Clause 56. The system of clause 55 wherein a difference between the first tissue resection profile and the second incision profile defines a volume of resected tissue.

Clause 57. The system of clause 55 wherein the adjustable contact element comprises a first surface profile configuration to shape the tissue to the first surface profile and a second surface profile configuration to shape the tissue to the second surface profile.

Clause 58. The system of clause 55, the adjustable contact element comprises inner elements to define the first surface profile and the second surface profile and outer elements to define the one or more complimentary features.

Clause 59. The system of clause 58, wherein the outer elements are configured to remain substantially fixed while the tissue is incised with advancement of the electrode and retraction of the electrode and inner elements are configured to shape the tissue to the first surface profile with a first configuration while the electrode is advanced and to the second surface profile with a second configuration while the electrode is retracted.

Clause 60. The system of clause 45, wherein the one or more of the channel or the protrusion comprises a plurality of channels to form a plurality of protrusions in the tissue surface and a plurality of corresponding complimentary features.

Clause 61. The system of clause 60, wherein the plurality of channels of the contact element are separated from each other by a distance within a range from about 200 μm to about 1000 μm.

Clause 62. The system of clause 45, wherein the one or more of the channel or the protrusion comprises a plurality of protrusions to form a plurality of indentations in the tissue surface and a plurality of corresponding complimentary features.

Clause 63. The system of clause 62, wherein the plurality of protrusions of the contact element are separated from each other by a distance within a range from about 200 μm to about 1000 μm.

Clause 64. The system of clause 45, wherein the one or more of the channel or the protrusion of the contact element comprises a width within a range from about 50 μm to about 500 μm.

Clause 65. The system of clause 45, wherein the one or more of the channel or the protrusion of the contact element comprises a depth within a range from about 50 μm to about 500 μm.

Clause 66. The system of clause 45, further comprising a vacuum source coupled to the contact element to shape the tissue with the contact element.

Clause 67. The system of clause 66, wherein the one or more of the channel or the protrusion comprises a channel coupled to the vacuum source to draw tissue into the channel to shape the tissue surface with a corresponding protrusion of the tissue surface.

Clause 68. The system of clause 66, wherein the one or more of the channel or the protrusion comprises the protrusion, the protrusion coupled to a channel coupled to the vacuum source in proximity to the protrusion to form a corresponding indentation in the tissue surface.

Clause 69. The system of clause 66, wherein the vacuum source provides a vacuum pressure within a range from about 100 mm Hg to about 600 mm Hg.

Clause 70. The system of clause 45, further comprising: an electrical energy source operatively coupled to the elongate electrode and configured to provide electrical energy to the electrode to generate the plasma; and a tensioning element operatively coupled to the elongate electrode, the tensioning element configured to provide tension to the elongate electrode to allow the elongate electrode to flex in response to the elongate electrode engaging the tissue and generating the plasma.

Clause 71. The system of clause 70, further comprising a plurality of arms operatively coupled to the electrode and the tensioning element.

Clause 72. The system of clause 71, wherein the electrode is unsupported between the two arms.

Clause 73. The system of clause 45, further comprising a processor configured to perform the method of any one of the preceding method clauses.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein.

What is claimed is:

1. A method of incising tissue, the method comprising: shaping a tissue surface with a tissue contact plate comprising a plurality of channels or a plurality of protrusions to form a plurality of complementary features in the tissue surface; incising the tissue along a tissue incision profile with an electrode while the tissue has been shaped with the tissue contact plate; and removing the tissue contact plate to allow the tissue to relax to a free-standing configuration and form the plurality of complimentary features corresponding to the plurality of channels or the plurality of protrusions of the tissue contact plate along the tissue incision profile.

2. The method of claim 1, wherein the plurality of complimentary features comprises one or more protrusions on a first side of the tissue incision profile and one or more corresponding indentations on a second side of the tissue incision profile to stabilize the tissue in the free-standing configuration at an interface between the first side and the second of the tissue incision profile.

3. The method of claim 2, wherein the tissue incision profile defines a first portion of tissue on the first side of the tissue incision profile and a second portion of tissue on the second side of the tissue incision profile and wherein the first portion comprises the one or more protrusions and the second portion comprises the one or more corresponding indentations sized and shaped to receive the one or more protrusions in the free-standing configuration.

4. The method of claim 3, wherein the one or more protrusions and the one or more corresponding indentations comprise a plurality of interlocking features.

5. The method of claim 3, wherein the first portion comprises the tissue surface and the second portion comprises a bed of tissue.

6. The method of claim 3, wherein the second portion comprises the tissue surface and the first portion comprises a bed of tissue.

7. The method of claim 1, wherein the plurality of channels or the plurality of protrusions of the tissue contact plate comprises the plurality of channels and wherein the plurality of channels is sized to receive the tissue surface to form one or more corresponding protrusions along the tissue incision profile in the free-standing configuration.

8. The method of claim 7, wherein the tissue incision profile defines a first portion of tissue on a first side of the tissue incision profile and a second portion of tissue on a second side of the tissue incision profile and wherein the first portion comprises one or more protrusions and the second portion comprises one or more corresponding indentations sized and shaped to receive the one or more protrusions.

9. The method of claim 8, wherein the one or more protrusions on the first portion and the one or more corresponding indentations on the second portion comprise an interlocking configuration.

10. The method of claim 1, wherein the plurality of channels or the plurality of protrusions of the tissue contact plate comprises the plurality of protrusions and wherein the plurality of protrusions is sized to indent the tissue surface to form one or more corresponding indentations along the tissue incision profile in the free-standing configuration.

11. The method of claim 10, wherein the tissue incision profile defines a first portion of tissue on a first side of the tissue incision profile and a second portion of tissue on a second side of the tissue incision profile and wherein the first portion comprises one or more indentations and the second portion comprises one or more corresponding protrusions sized and shaped to fit into the one or more indentations.

12. The method of claim 11, wherein the one or more indentations on the first portion and the one or more corresponding protrusions on the second portion comprise an interlocking configuration.

13. The method of claim 1, wherein the tissue incision profile comprises a linear incision profile when the tissue is incised with the electrode.

14. The method of claim 13, wherein the tissue incision profile comprises a two-dimensional linear incision profile when the tissue is engaged with the tissue contact plate and wherein the plurality of complimentary features comprises a three-dimensional complimentary surface profile when the tissue has relaxed to the free-standing configuration.

15. The method of claim 1, wherein the plurality of complimentary features comprise one or more of interlocking features or mating features.

16. The method of claim 1, wherein the plurality of complimentary features extends along an outer region of the tissue incision profile and at least partially around an inner region of the tissue incision profile.

17. The method of claim 16, wherein the plurality of complimentary features extend semi circumferentially around the inner region of the incision profile.

18. The method of claim 1, wherein the plurality of complimentary features extends along an outer region of the tissue incision profile to define a central optical zone of a cornea of an eye.

19. The method of claim 1, wherein tissue is incised with advancement and retraction of the electrode and wherein the tissue surface comprises a first surface profile corresponding to a first tissue resection profile while the electrode is advanced and a second surface profile while the electrode is retracted to define a volume of resected tissue corresponding to a difference between the first surface profile and the second surface profile.

* * * * *